(12) United States Patent
McDonald et al.

(10) Patent No.: US 10,869,934 B2
(45) Date of Patent: *Dec. 22, 2020

(54) ANTIPROLIFERATIVE COMPOUNDS AND CONJUGATES MADE THEREFROM

(71) Applicant: BRISTOL-MYERS SQUIBB COMPANY, Princeton, NJ (US)

(72) Inventors: Ivar M. McDonald, Woodstock, CT (US); Prasanna Sivaprakasam, Lawrenceville, NJ (US); Christiana I. Iwuagwu, Hamden, CT (US); Kevin M. Peese, Haddam, CT (US); Heng Cheng, Fremont, CA (US); Naidu S. Chowdari, Sunnyvale, CA (US); Sanjeev Gangwar, Foster City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/533,226

(22) Filed: Aug. 6, 2019

(65) Prior Publication Data

US 2019/0358339 A1 Nov. 28, 2019

Related U.S. Application Data

(63) Continuation of application No. 15/789,027, filed on Oct. 20, 2017, now Pat. No. 10,398,783.

(60) Provisional application No. 62/410,624, filed on Oct. 20, 2016.

(51) Int. Cl.
| | | |
|---|---|---|
| *A61K 47/68* | (2017.01) | |
| *C07D 471/04* | (2006.01) | |
| *C07D 519/00* | (2006.01) | |
| *C07F 7/08* | (2006.01) | |
| *C07K 5/062* | (2006.01) | |

(52) U.S. Cl.
CPC ........ *A61K 47/6803* (2017.08); *C07D 471/04* (2013.01); *C07D 519/00* (2013.01); *C07F 7/0814* (2013.01); *C07K 5/06026* (2013.01)

(58) Field of Classification Search
CPC ............................ C07D 471/04; A61K 47/6803
See application file for complete search history.

(56) References Cited

U.S. PATENT DOCUMENTS

| | | |
|---|---|---|
| 2012/0095213 A1 | 4/2012 | Ahmed et al. |
| 2016/0199510 A1 | 7/2016 | Mcdonald et al. |
| 2016/0200742 A1 | 7/2016 | Zhang et al. |
| 2016/0271142 A1 | 9/2016 | Junutula et al. |

FOREIGN PATENT DOCUMENTS

| | | |
|---|---|---|
| WO | WO 1993/18045 | 9/1993 |
| WO | WO 2005/082023 A2 | 9/2005 |
| WO | WO 2016/198869 A1 | 12/2016 |

OTHER PUBLICATIONS

Baraldi, et al., "Design, Synthesis and Biological Activity of a Pyrrolo . . . ," *Bioorganic Medicinal Chem Letters*, vol. 08, pp. 3019-3024, 1998.
Baraldi, et al., "Synthesis, In Vitro Antiproliferative Activity, and DNS-Binding Properties of Hybrid Molecules . . . ," *J. Med. Chem*, vol. 42, pp. 5131-5141, 1999.
Bose, et al., "Rational Design of Highly Efficient Irreversible DNA Interstrand Cross-Linking Agent Based on the Pyrrolobenzodiazepine Ring System," *J. Am Chem Soc.* vol. 114, pp. 4939-4941, 1992.
Damayanthi, et al., "Design and Synthesis of Novel Pyrrolo[2,1-c] Benzodiazepine-Lexitropsin Conjugates,"*J. Organic Chem.*, vol. 64, pp. 290-292, 1999.
Kothakonda, et al., "Synthesis of a Novel Tetrahydroisoquinolino [2,1-c][1,4] Benzodiazepine Ring System with DNA Recognition Potential," *Bioorganic & Medicinal Chemistry Letters*, vol. 14, pp. 4371-4373, 2004.
Kumar, et al., "Design, synthesis and in vitro cytotoxic studies of novel bis-pyrrolo[2,1][1,4] Benzodiazepine-Pyrrole and ImidazoleP-polyamide Conjugates", *Eur. J. Medicinal Chem.*, vol. 40, pp. 641-654, 2005.
Kumar, et al., "Design and Synthesis of Novel Pyrrolo[2,1-c][1,4] Benzodiazepine-Imidazole Containing Polyamide Conjugates" *Heterocyclic Communications.*, vol. 8, pp. 19-26, 2002.
Kumar, et al.,"Synthesis and Antitumor Cytotoxicity Evaluation of Novel . . . ," *Oncology Research*, vol. 13, pp. 221-233, 2002.
Kumar, et al., "Design, Synthesis and In Vitro Cytotoxicity Studies of Novel Pyrrolo . . . " *Org. Biomol.Chem.*, vol. 1, pp. 3327-3342, 2003.
Rahman, et al., "GC-Targeted C8-Linked Pyrrolobenzodiazepine-Biaryl Conjugates with Femtomolar . . . ," *J Medicinal Chemistry*, vol. 56, pp. 52911-2935, 2013.
Reddy, et al., "Design, Synthesis and In Vitro Cytotoxicity Studies of Novel . . . ," *Anti-Cancer Drug Design*, vol. 15, pp. 225238, 2000.
Schrama, et al., "Antibody Targeted Drugs as Cancer Therapeutics," *Nature Reviews Drug Disc.*, vol. 5, pp. 147-159, 2006.

(Continued)

*Primary Examiner* — Timothy P Thomas
(74) *Attorney, Agent, or Firm* — Yuan Chao

(57) ABSTRACT

A compound capable of inhibiting cell proliferation, having a structure according to formula (I)

(I)

wherein the variables in formula (I) are as defined in the specification. Such compounds are useful as anti-cancer agents, especially in antibody-drug conjugates.

1 Claim, 9 Drawing Sheets

(56) References Cited

OTHER PUBLICATIONS

Tercel, et al., "Unsymmetrical DNA Cross-Linking Agents: Combination of the CBI and PBD Pharmacophores," *J. Medicinal Chem.*, vol. 46, No. 11, pp. 2132-2151, 2003.

Wells, et al., "Design, Synthesis, and Biophysical and Biological Evaluation of a Series of Pyrrolobenzodiazepine-Poly(N-Methylpyrrole) Conjugates," *J. Medicinal Chem..*, vol. 49, pp. 5442-5461, 2006.

International Search Report and Written Opinion, for PCT Application No. PCT/US2017/057508, dated Dec. 8, 2017.

ANTIPROLIFERATIVE COMPOUNDS AND CONJUGATES MADE THEREFROM

CROSS-REFERENCE TO RELATED APPLICATIONS

This application is a continuation of application Ser. No. 15/789,027, now allowed and issue fee therefor paid; which claims the benefit under 35 U.S.C. § 119(e) of U.S. Provisional Application Ser. No. 62/410,624, filed Oct. 20, 2016; the disclosures of which are incorporated herein by reference.

BACKGROUND OF THE INVENTION

This specification discloses, inter alia, drug compounds that inhibit cell proliferation, antibody-drug conjugates made therefrom, drug-linker compounds for making such conjugates, uses of such compounds and their antibody-drug conjugates, and methods and intermediates for their making.

Double helical DNA has two longitudinal spiral grooves running along its exterior, much like the stripes on a barbershop pole. The two grooves are not identical: one, called the major groove, is much wider than the other, called the minor groove.

The width of the minor groove is approximately equal to the thickness of a benzene ring. Many biologically active DNA-binding molecules—whether synthetic or naturally occurring—are substantially planar polyaromatic molecules having an arcuate footprint, such shape enabling them to fit snugly into the minor groove. For short, a DNA minor groove binding molecule is referred to herein as an MGB, or minor groove binder.

One type of MGB is a dimer of two polyaromatic units, each comprising a benzodiazepine and a tetrahydroisoquinoline ("THIQ") ring system, as shown by the representative structure below. Such MGBs are disclosed in Zhang et al. 2016, McDonald et al. 2016, and Junutula et al. 2016.

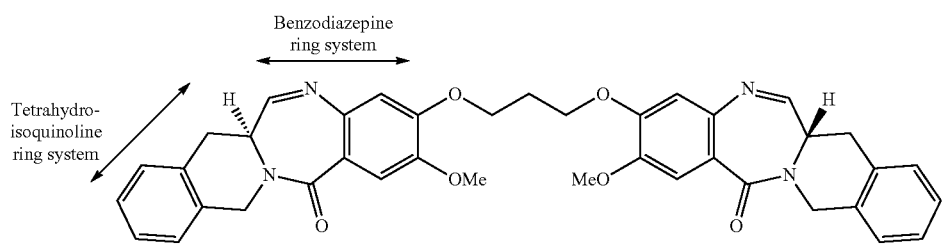 [SMILES: COc1cc2c(cc1OCCCOc1cc3c(cc1OC)C(=O)N1Cc4ccccc4C[C@H]1C=N3)N=C[C@@H]1Cc3ccccc3CN1C2=O]

Another type of MGB is also a dimer of two polyaromatic units, but in this instance comprising a pyrrolobenzodiazepine ("PBD") ring system, as illustrated by the structure below. Bose et al. 1992 and Thurston et al. 1993 are exemplary publications disclosing such MGBs.

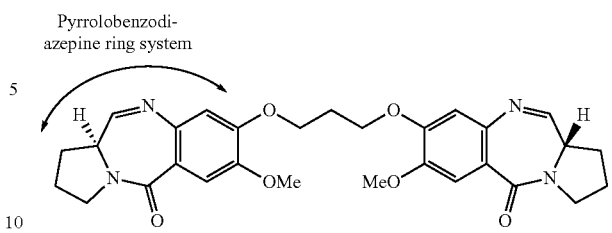

Yet another type of MGB is represented by the natural products distamycin and netropsin, comprising aminopyrrolecarboxylic acid moieties linked by amide bonds:

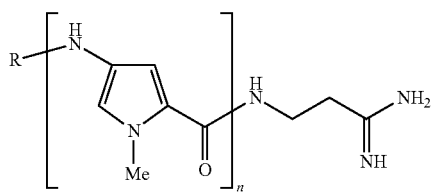

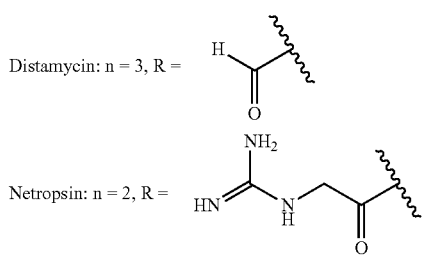

Still yet another type of MGB is represented by the natural products duocarmycin SA and yatakemycin, which have a characteristic cyclopropapyrroloindole ("CPI") subunit and are therefore often referred to as CPI compounds. Members in this class include their seco (ring-opened) counterparts.

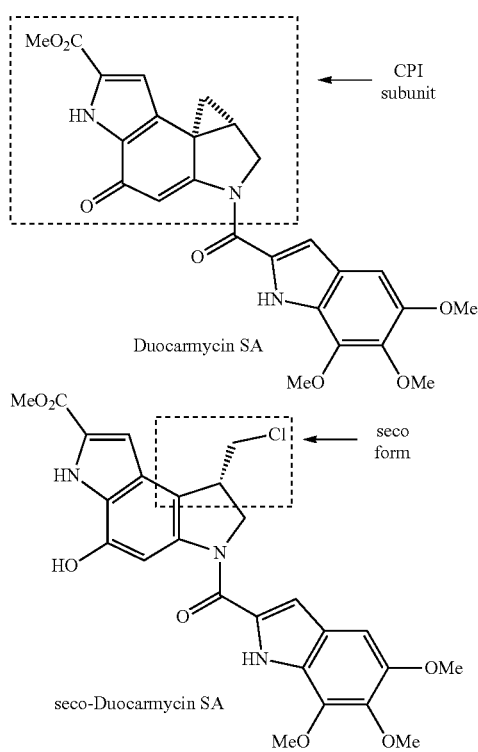

Duocarmycin SA seco-Duocarmycin SA

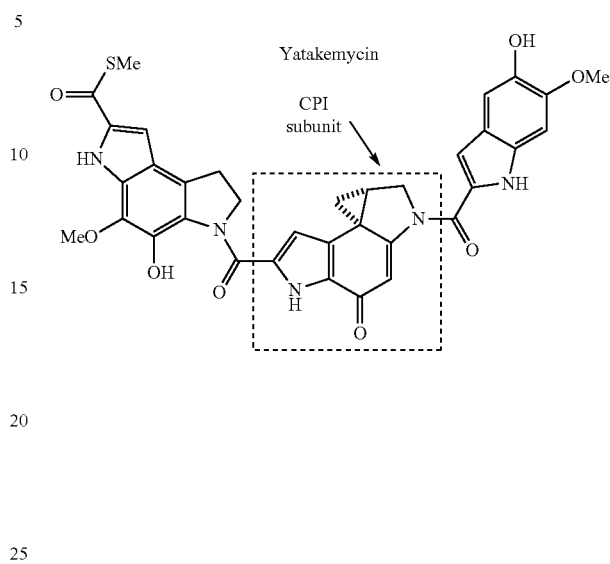

Yatakemycin

There exist a number of disclosures of synthetic compounds combining structural features from different types of MGBs. Rahman et al. 2013 disclose compounds combining a PBD moiety and a distamycin-like moiety, such as:

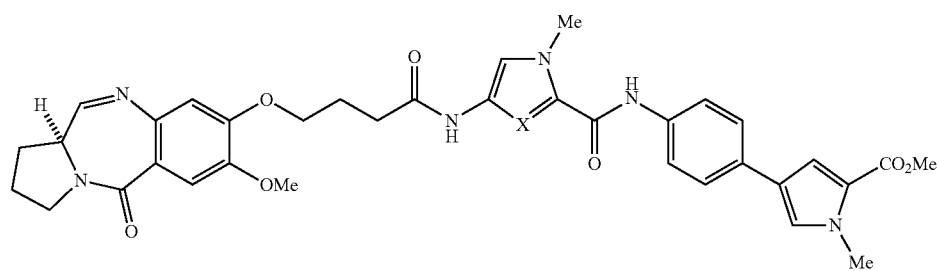

(X = N or CH)

Zhang et al. 2016 and Junutula et al. 2016 disclose MGB heterodimers comprising one THIQ containing unit and one PBD unit. An illustrative structure is shown below.

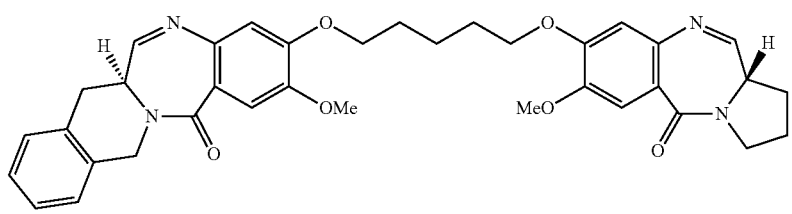 [SMILES: COc1cc2c(cc1OCCCCCOc1cc3c(cc1OC)C(=O)N1Cc4ccccc4C[C@H]1C=N3)N=C[C@@H]1CCCN1C2=O]

Yet other disclosures of compounds combining different MGB moieties include: Ahmed et al. 2012; Baraldi et al. 1998 and 1999; Demayanthi et al. 1999; Kumar and Lown 2002 and 2003; Kumar et al. 2002 and 2005; Reddy et al. 2000; Tercel et al. 2003; Thurston et al. 2016; and Wells et al. 2006.

The biological activity of MGBs derives from their ability to bind to DNA and disrupt its transcription and, in some instances, chemically react with DNA and damage it. Consequently, many MGBs are highly cytotoxic. There is interest in the use of MGBs for the treatment of cancer, as their cytotoxicity can make them effective in killing cancer cells.

A type of anticancer agent that is generating strong interest is a conjugate, in which a drug is attached to a targeting agent that binds to a ligand on the cancer cell. The targeting agent, by binding to its ligand, directs the drug to the cancer cell, where it is released by one of several mechanisms, to act on the cancer cell.

A common type of conjugate is an antibody-drug conjugate ("ADC," also referred to as an immunoconjugate). In an ADC, a drug (synonymously therapeutic agent, cytotoxin, payload, or warhead) is covalently linked to an antibody whose antigen is a tumor associated antigen—i.e., an antigen expressed by a cancer cell. MGBs have potential as the drug in an ADC.

The moiety covalently linking the antibody and the drug is referred to as the linker. Where each antibody has one drug attached to it, the structure of an ADC can be represented generically as:

[Antibody]-[Linker]-[Drug]

The antibody, upon binding to its antigen, delivers the ADC to the cancer site. There, cleavage of the linker or degradation of the antibody releases the drug. Frequently, the ADC is internalized by endocytosis into the target cell and release of the drug takes place inside it. While the ADC is circulating in the blood, the drug is held inactive because of its linkage to the antibody. Consequently, the drug in an ADC can be much more potent (cytotoxic) than an ordinary chemotherapy agent because its localized release reduces systemic toxicity. For a review on ADCs, see Schrama et al. 2006.

Full citations for the documents cited herein by first author or inventor and year are listed at the end of this specification.

BRIEF SUMMARY OF THE INVENTION

There is provided a heterodimeric compounds comprising a benzodiazepine-containing moiety in one half and an aromatic polyamide moiety in the other half. Such compounds are biologically active, inhibiting the proliferation of cells (especially cancer cells), and can be used as anticancer agents, particularly as the drug component in an ADC. Without being bound by theory, it is believed that such heterodimeric compounds function like MGBs and derive their biological activity from an ability to bind to DNA and/or damage it chemically.

In one aspect, there is provided a compound having a structure represented by formula (I)

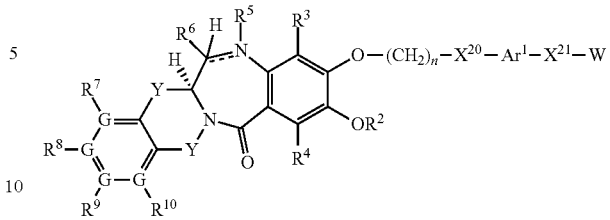

wherein
each G is C or N, with the proviso that no more than two Gs are N (preferably each G is C);
$R^2$ is H or $C_1$-$C_5$ alkyl;
$R^3$ and $R^4$ are independently H, F, Cl, Br, OH, $C_1$-$C_3$ alkyl, $O(C_1$-$C_3$ alkyl), cyano, $(CH_2)_{0-5}NH_2$, or $NO_2$;
the double line ==== in the diazepine ring system represents a single bond or a double bond;
$R^5$ is H if the double line ==== is a single bond and is absent if the double line ==== is a double bond;
$R^6$ is H, OH, $SO_3Na$, or $SO_3K$ if the double line ==== is a single bond and is absent if the double line ==== is a double bond;
$R^7$, $R^8$, $R^9$, and $R^{10}$ are independently H, $C_1$-$C_5$ alkyl, $C\equiv C(CH_2)_{1-5}X^2$, OH, $O(C_1$-$C_5$ alkyl), cyano, $NO_2$, F, Cl, Br, $O(CH_2CH_2O)_{1-8}(C_{1-3}$ alkyl), $(CH_2)_{0-5}X^2$, O $(CH_2)_{2-5}X^2$, 3- to 7-membered cycloalkyl or heterocycloalkyl unsubstituted or substituted with $(CH_2)_{0-5}X^2$ or O $(CH_2)_{2-5}X^2$, phenyl unsubstituted or substituted with $(CH_2)_{0-5}X^2$ or $O(CH_2)_{2-5}X^2$, 5- to 6-membered heteroaryl unsubstituted or substituted with $(CH_2)_{0-5}X^2$ or O $(CH_2)_{2-5}X^2$,

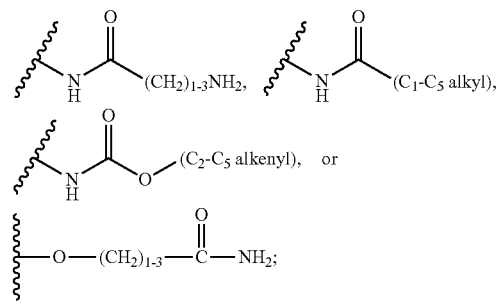

or where a $R^7$, $R^8$, $R^9$, or $R^{10}$ is attached to a G that is N, such $R^7$, $R^8$, $R^9$, or $R^{10}$ is absent;
each $X^2$ is independently H, F, Cl, Br, OH, $O(C_1$-$C_3$ alkyl), $O(C_1$-$C_3$ alkylene), $CO_2H$, $N_3$, CN, $NO_2$, $CO_2(C_1$-$C_3$ alkyl), $NH_2$, $NH(C_1$-$C_5$ alkyl), $N(C_1$-$C_5$ alkyl)$_2$, SH, CHO, $N(CH_2CH_2)_2N(C_1$-$C_3$ alkyl), $NHNH_2$, or $C(=O)$ $NHNH_2$;
each Y is independently $CH_2$, $C=O$, or $CHR^{12}$; wherein each $R^{12}$ is independently F, Cl, Br, or $C_1$-$C_3$ alkyl;
n is 2, 3, 4, 5, or 6;
$X^{20}$ and $X^{21}$ are independently

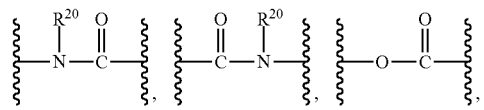

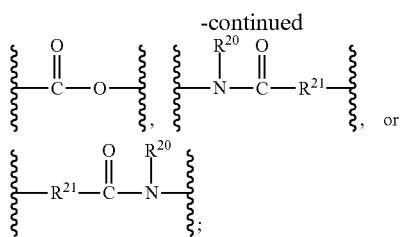
-continued wherein $R^{20}$ is H or $C_1$-$C_3$ alkyl and $R^{21}$ is O, NH, or N($C_1$-$C_3$ alkyl);

$Ar^1$ is (i) a phenyl moiety, (ii) a 5- or 6-membered heteroaromatic moiety, or (iii) a polycyclic aromatic moiety comprising a phenyl or 6-membered heteroaromatic ring fused to a phenyl ring or a 5- or 6-membered heteroaromatic ring; each phenyl, heteroaromatic, or polycyclic aromatic moiety being optionally substituted with one or more of $C_1$-$C_6$ alkyl (especially Me), Cl, or F; and W is (a) $C_1$-$C_6$ alkyl or $C_3$-$C_6$ cycloalkyl or (b) an aromatic moiety comprising one to three (i) phenyl or (ii) 5- or 6-membered heteroaromatic rings, which phenyl or 5- or 6-membered heteroaromatic rings are optionally substituted with one or more of $C_1$-$C_3$ alkyl, OH, Cl, F, $CH_2F$, $CHF_2$, $CF_3$, O($C_1$-$C_3$ alkyl), O($CH_2$)$_{2-4}$OH, O($CH_2$)$_{0-2}$$CHF_2$, C(=O)($C_1$-$C_3$ alkyl), C(=O)O($C_1$-$C_3$ alkyl), C(=O)$NH_2$, C(=O)NH($C_1$-$C_3$ alkyl), C(=O)N($C_1$-$C_3$ alkyl)$_2$, O($C_2$-$C_4$ alkenyl), $NH_2$, NH($C_1$-$C_3$ alkyl), N($C_1$-$C_3$ alkyl)$_2$, O($CH_2$)$_{0-2}$$C_6H_5$, CN, or $NO_2$; wherein, if more than one phenyl or 5- or 6-membered heteroaromatic ring is present, such rings are fused to each other or joined by an aryl-aryl bond;

or a pharmaceutically acceptable salt thereof.

In another aspect, there is provided a compound according to formula (I) having attached to it a linker having a functional group suitable for forming a bond with a targeting moiety, in particular an antibody.

In yet another aspect, there is provided a compound according to formula (I) conjugated to a targeting agent, especially an antibody.

In yet another aspect, there is provided a method of treating a cancer in a subject suffering from such cancer, comprising administering to the subject a therapeutically effective amount of a compound according to formula (I) or a conjugate thereof with a targeting agent, especially an antibody. Especially, the cancer so treated can be colon cancer, stomach cancer, ovarian cancer, or mesothelioma.

BRIEF DESCRIPTION OF THE DRAWING(S)

DETAILED DESCRIPTION OF THE INVENTION

Definitions

Figure 1:
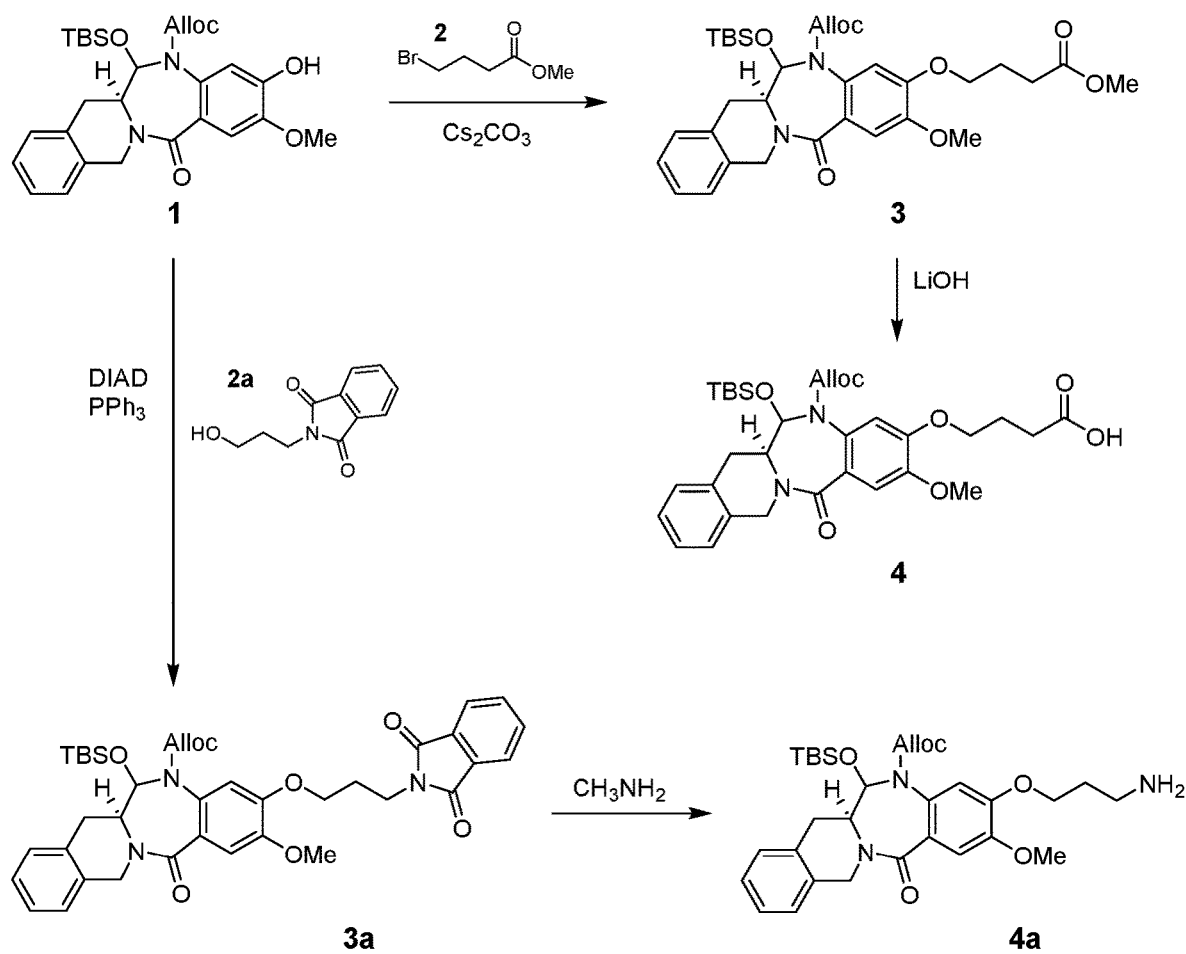
FIG. 1 shows a reaction scheme for the synthesis of intermediates useful for the synthesis of compounds disclosed herein.

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and Cm domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germ-line immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human anti-body" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like.

"Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.+

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene"

means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ( ~~~ ) transverse to a bond or an asterisk (*) at the end of the bond denotes a covalent attachment site. For instance, a statement that R is

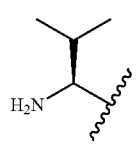

or that R is

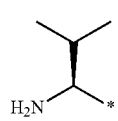

in the formula

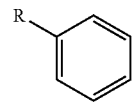

means

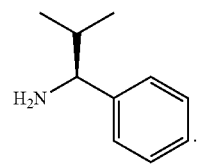

In the formulae of this specification, a bond traversing an aromatic ring between two carbons thereof means that the group attached to the bond may be located at any of the available positions of the aromatic ring. By way of illustration, the formula

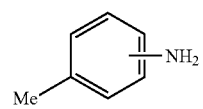

represents

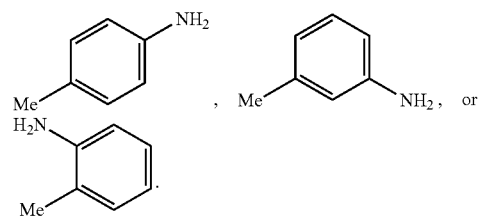

Compounds

In a preferred embodiment, compounds disclosed herein have a structure according to formula (Ia):

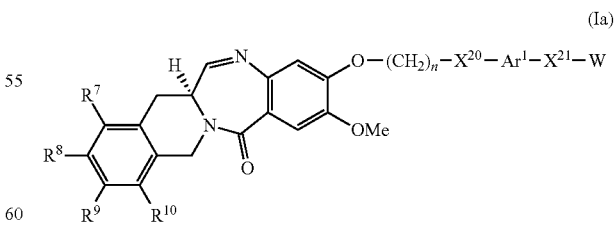

(Ia)

where $R^7$, $R^8$, $R^9$, $R^{10}$, n, $X^{20}$, $Ar^1$, $X^{21}$, and W are as defined in respect of formula (I) in the BRIEF SUMMARY OF THE INVENTION section hereinabove.

A more preferred compound according to formula (I) has a structure represented by formula (Ib)

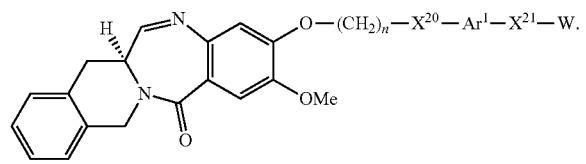
(Ib)
Examples of compounds according to formula (Ib) are shown in Table I below.
TABLE I
| Compound | n | —X²⁰—Ar¹—X²¹— | W |
|---|---|---|---|
| (Ib-01) | 3 | 1,4-phenylene bis-amide linker | phenyl |
| (Ib-02) | 3 | 1,2-phenylene bis-amide linker | phenyl |
| (Ib-03) | 3 | 1,3-phenylene bis-amide linker | phenyl |
| (Ib-04) | 3 | thiazole (2,5) bis-amide linker | phenyl |
| (Ib-05) | 3 | thiazole (2,4) bis-amide linker | phenyl |
| (Ib-06) | 3 | N-methylpyrrole bis-amide linker | 5-(3-methyl-1,2,4-triazol-1-yl)pyridin-2-yl |

TABLE I-continued
| Compound | n | 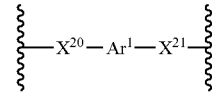 | W |
|---|---|---|---|
| (Ib-07) | 3 | 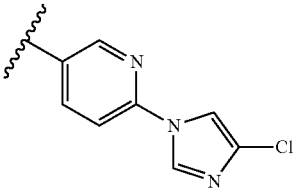 [SMILES: *c1ccc(-n2cnc(Cl)c2)nc1] | 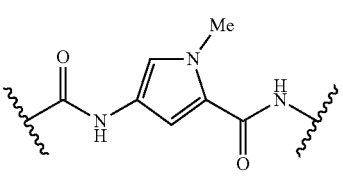 [SMILES: *NC(=O)c1cc(NC(*)=O)cn1C] |
| (Ib-08) | 3 | 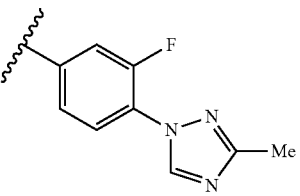 [SMILES: *c1ccc(-n2cnc(C)n2)c(F)c1] | 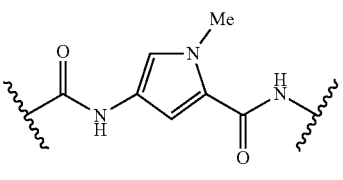 [SMILES: *NC(=O)c1cc(NC(*)=O)cn1C] |
| (Ib-09) | 3 | 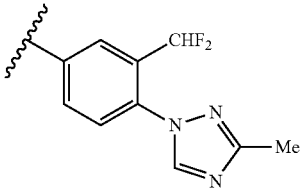 [SMILES: *c1ccc(-n2cnc(C)n2)c(C(F)F)c1] | 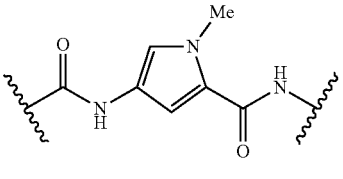 [SMILES: *NC(=O)c1cc(NC(*)=O)cn1C] |
| (Ib-10) | 3 | 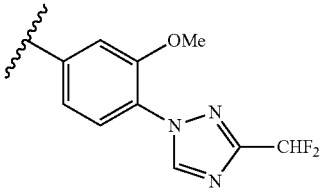 | 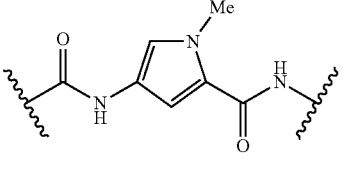 [SMILES: *NC(=O)c1cc(NC(*)=O)cn1C] |
| (Ib-11) | 3 | 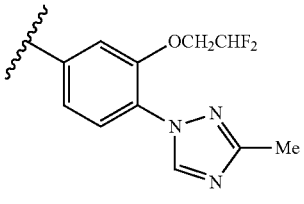 | 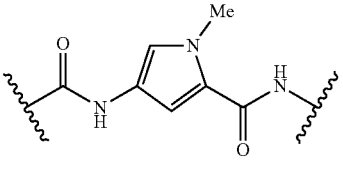 [SMILES: *NC(=O)c1cc(NC(*)=O)cn1C] |
| (Ib-12) | 3 | 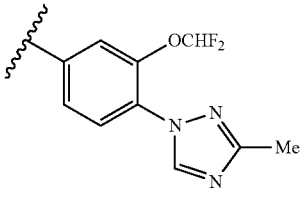 [SMILES: *c1ccc(-n2cnc(C)n2)c(OC(F)F)c1] | 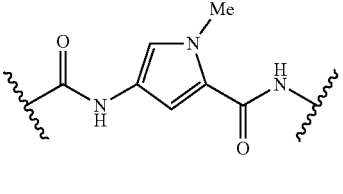 [SMILES: *NC(=O)c1cc(NC(*)=O)cn1C] |
| (Ib-13) | 3 | 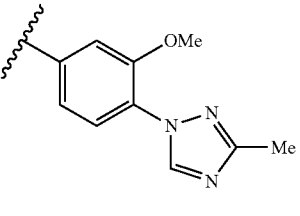 [SMILES: *c1ccc(-n2cnc(C)n2)c(OC)c1] | |

TABLE I-continued

| Compound | n | $-X^{20}-Ar^1-X^{21}-$ | W |
|---|---|---|---|
| (Ib-14) | 3 | 1-methyl-pyrrole-2,4-dicarboxamide linker | 4'-(isopropoxycarbonyl)biphenyl (3-position ester) |
| (Ib-15) | 3 | 1-methyl-pyrrole-2,4-dicarboxamide linker | 4'-methoxybiphenyl |
| (Ib-16) | 3 | 1-methyl-pyrrole-2,4-dicarboxamide linker | 4-(3-methyl-1H-1,2,4-triazol-1-yl)phenyl |
| (Ib-17) | 3 | 1-methyl-pyrrole-2,4-dicarboxamide linker | 4-(1H-1,2,4-triazol-1-yl)phenyl |
| (Ib-18) | 3 | 1-methyl-pyrrole-2,4-dicarboxamide linker | 2-methoxy-4-(4-(difluoromethyl)-1H-imidazol-1-yl)phenyl |
| (Ib-19) | 3 | 1-methyl-pyrrole-2,4-dicarboxamide linker | 2-methoxy-4-(4-chloro-1H-imidazol-1-yl)phenyl |
| (Ib-20) | 3 | 1-methyl-pyrrole-2,4-dicarboxamide linker | 2-fluoro-4-(4-chloro-1H-imidazol-1-yl)phenyl |

TABLE I-continued
| Compound | n | -X²⁰—Ar¹—X²¹- | W |
|---|---|---|---|
| (Ib-21) | 3 | 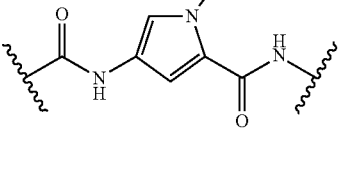 | 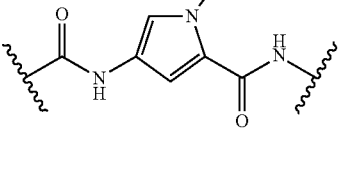 |
| (Ib-22) | 3 | | |
| (Ib-23) | 3 | | |
| (Ib-24) | 3 | | |
| (Ib-25) | 3 | | |
| (Ib-26) | 3 | | |
| (Ib-27) | 3 | | |

TABLE I-continued

| Compound | n | -X²⁰—Ar¹—X²¹- | W |
|---|---|---|---|
| (Ib-28) | 3 | pyrrole-diamide (N-Me) | 3,5-dimethylphenyl-1,2,4-triazol-1-yl |
| (Ib-29) | 3 | pyrrole-diamide (N-Me) | 2-methoxyphenyl-1,2,4-triazol-1-yl |
| (Ib-30) | 3 | pyrrole-diamide (N-Me) | 4-(1H-imidazol-2-yl)phenyl |
| (Ib-31) | 3 | pyrrole-diamide (N-Me) | 4H-benzo[b][1,2,4]triazolo[4,3-d][1,4]oxazine |
| (Ib-32) | 3 | pyrrole-diamide (N-Me) | 4H-benzo[b][1,2,4]triazolo[3,4-d][1,4]oxazine |
| (Ib-33) | 3 | pyrrole-diamide (N-Me) | dibenzofuran-3-yl |
| (Ib-34) | 3 | pyrrole-diamide (N-Me) | 7-amino-9H-fluoren-2-yl |
| (Ib-35) | 3 | pyrrole-diamide (N-Me) | 5-methoxypyridin-2-yl |

TABLE I-continued

| Compound | n | $-X^{20}-Ar^1-X^{21}-$ | W |
|---|---|---|---|
| (Ib-36) | 3 | N-methylpyrrole-2,4-dicarboxamide linker | 6-(benzyloxy)pyridin-2-yl |
| (Ib-37) | 3 | N-methylpyrrole-2,4-dicarboxamide linker | 3-methyl-3H-imidazo[4,5-b]pyridin-6-yl |
| (Ib-38) | 3 | N-methylpyrrole-2,4-dicarboxamide linker | Me |
| (Ib-39) | 3 | N-methylpyrrole-2,4-dicarboxamide linker | 4-(1-methyl-2-(methoxycarbonyl)-1H-pyrrol-4-yl)phenyl |
| (Ib-40) | 3 | N-methylpyrrole-2,4-dicarboxamide linker | 1-methyl-2-(methoxycarbonyl)-1H-pyrrol-4-yl |
| (Ib-41) | 3 | N-methylpyrrole-2,4-dicarboxamide linker | phenyl |
| (Ib-42) | 3 | N-methylpyrrole-2,4-dicarboxamide linker | cyclopropyl |
| (Ib-43) | 3 | N-methylpyrrole-2,4-dicarboxamide linker | biphenyl-4-yl |

TABLE I-continued

| Compound | n | -X²⁰—Ar¹—X²¹- | W |
|---|---|---|---|
| (Ib-44) | 3 | 4-amino-1-methyl-pyrrole-2-carboxamide linker | pyridin-2-yl |
| (Ib-45) | 3 | 4-amino-1-methyl-pyrrole-2-carboxamide linker | 5-chloropyridin-2-yl |
| (Ib-46) | 3 | 4-amino-1-methyl-pyrrole-2-carboxamide linker | pyridin-3-yl |
| (Ib-47) | 3 | 4-amino-1-methyl-pyrrole-2-carboxamide linker | 6-chloropyridin-3-yl |
| (Ib-48) | 3 | 4-amino-1-methyl-pyrrole-2-carboxamide linker | phenyl |
| (Ib-49) | 3 | 4-amino-1-methyl-pyrrole-2-carboxamide linker | 4-[1-methyl-5-(oxazol-2-yl)pyrrol-3-yl]phenyl |
| (Ib-50) | 3 | 4-amino-1-methyl-pyrrole-2-carboxamide linker | 4-[1-methyl-5-(N-methylcarbamoyl)pyrrol-3-yl]phenyl |

TABLE I-continued
| Compound | n | -X²⁰—Ar¹—X²¹- | W |
|---|---|---|---|
| (Ib-51) | 3 | 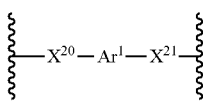 | 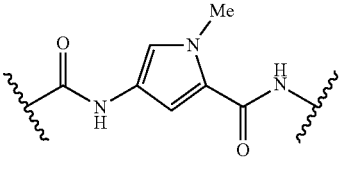 [SMILES: *NC(=O)c1cc(NC(*)=O)cn1C] |
| (Ib-52) | 3 | 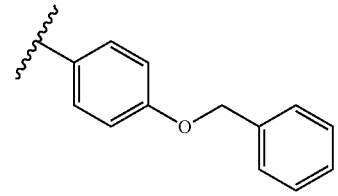 [SMILES: *c1ccc(OCc2ccccc2)cc1] | 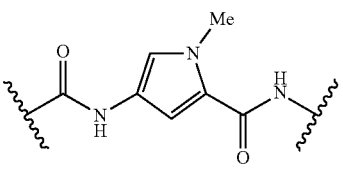 [SMILES: *NC(=O)c1cc(NC(*)=O)cn1C] |
| (Ib-53) | 3 | 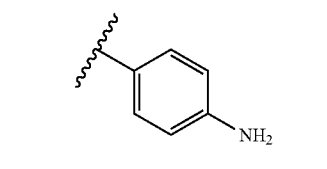 [SMILES: *c1ccc(N)cc1] | 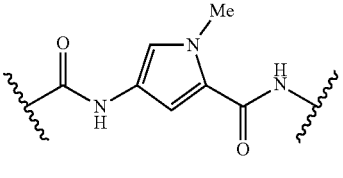 [SMILES: *NC(=O)c1cc(NC(*)=O)cn1C] |
| (Ib-54) | 3 | 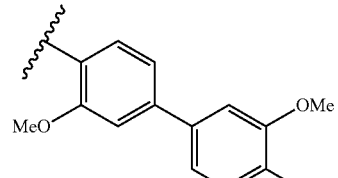 | 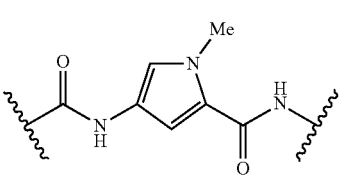 [SMILES: *NC(=O)c1cc(NC(*)=O)cn1C] |
| (Ib-55) | 3 | 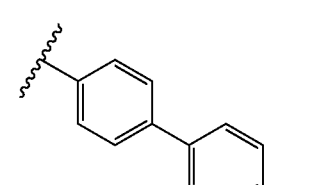 | 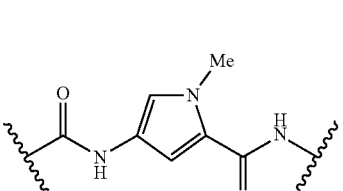 |
| (Ib-56) | 3 | 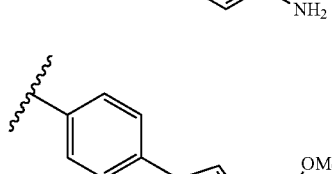 | 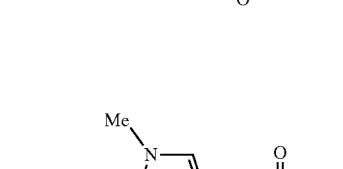 |
| (Ib-57) | 3 | 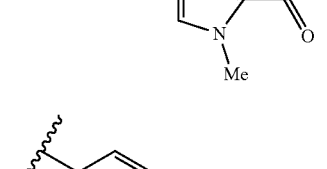 | 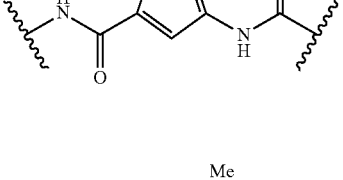 |

TABLE I-continued
| Compound | n | -X²⁰—Ar¹—X²¹- | W |
|---|---|---|---|
| (Ib-58) | 2 | 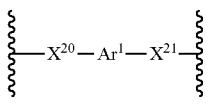 | 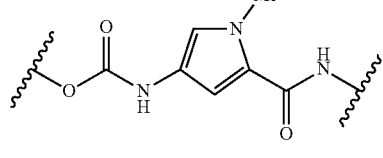 |
| (Ib-59) | 2 | 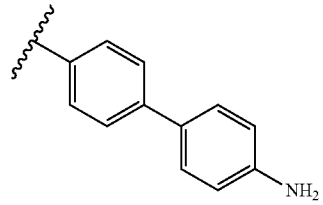 [SMILES: *c1ccc(-c2ccc(N)cc2)cc1] | 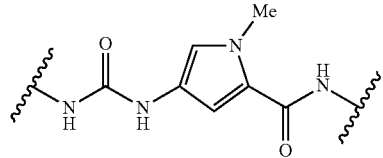 [SMILES: *NC(=O)Nc1cc(C(=O)N*)n(C)c1] |
| (Ib-60) | 3 | 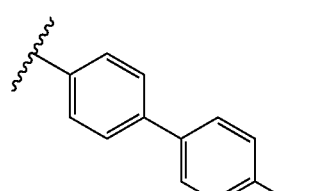 | 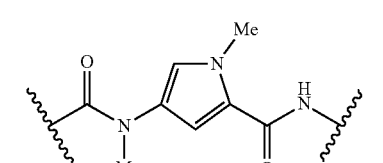 |
| (Ib-61) | 3 | 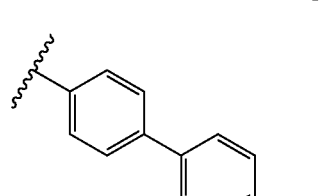 | 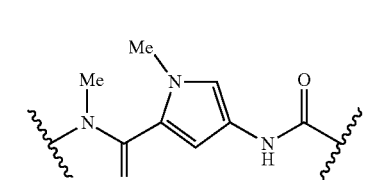 |
| (Ib-62) | 3 | 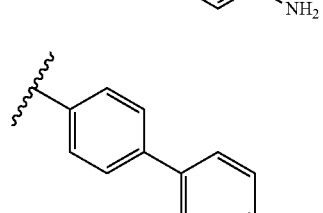 | 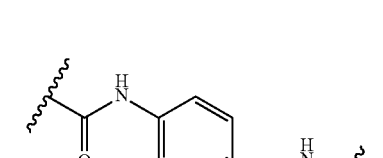 |
| (Ib-63) | 3 | 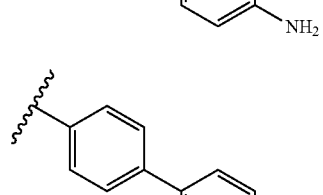 | 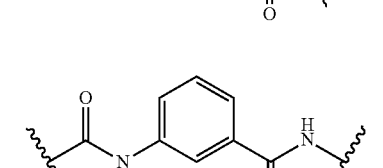 |
| (Ib-64) | 3 | 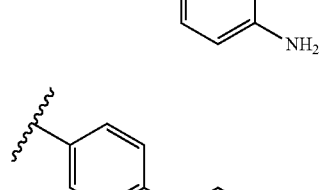 | 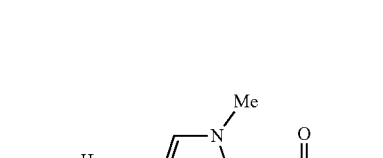 |

TABLE I-continued

| Compound | n | —X²⁰—Ar¹—X²¹— | W |
|---|---|---|---|
| (Ib-65) | 3 | 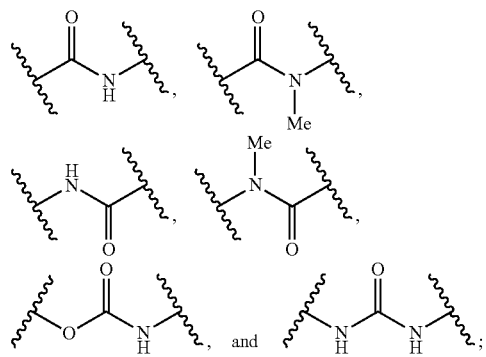 | 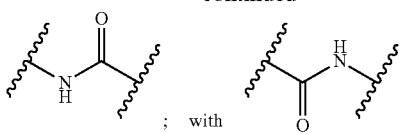 |

In this specification, the following preferences apply, unless the context indicates otherwise.

In formula (I) and the other formulae in which it appears, $R^2$ preferably is Me.

In formula (I) and the other formulae in which they appear, preferably both $R^3$ and $R^4$ are H.

In formula (I) and the other formulae in which they appear, preferably each Y is $CH_2$.

In formula (I) and the other formulae in which it appears, preferably n is 2 or 3, more preferably 3.

In formula (I) and the other formulae in which it appears, $R^{20}$ preferably is H.

In formula (I) and the other formulae in which it appears, and $R^{21}$ preferably is O or NH.

In formula (I) and the other formulae in which it appears, preferred groups $X^{20}$ are

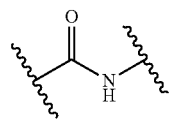

with

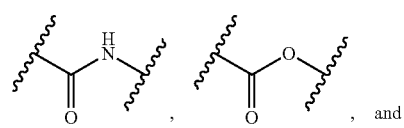

being especially preferred.

In formula (I) and the other formulae in which it appears, preferred groups $X^{21}$ are

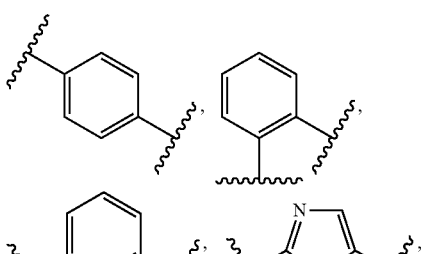; with 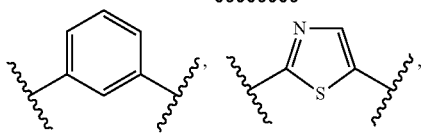 being especially preferred.

Regarding the group $Ar^1$ in formula (I) and in the other formulae where it appears: Suitable heteroaromatic moieties (ii) include pyridine, pyrimidine, pyrazine, pyrrole, furan, thiophene, imidazole, thiazole, oxazole, isoxazole, pyrazole, triazole, and isothiazole. Suitable polycyclic aromatic moieties (iii) include naphthalene, quinolone, isoquinoline, indole, benzimidazole, benzothiophene, benzofuran, benzotriazole, quinoxaline, and 1,6-naphthyridine. $Ar^1$ preferably is

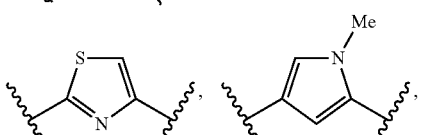

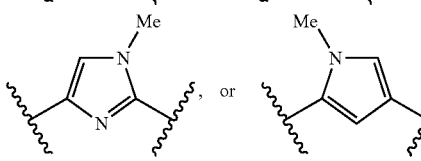

with 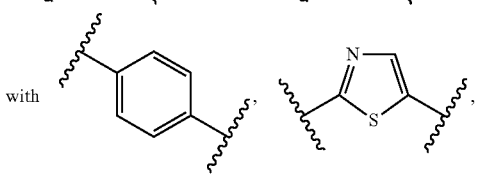

-continued
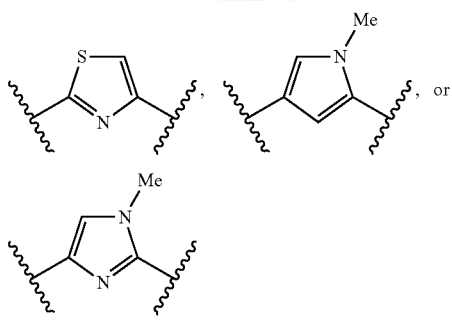
being more preferred;
and with
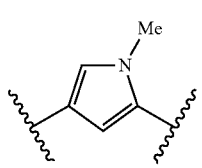 [SMILES: *c1cc(*)n(C)c1]
being especially preferred.
In formula (I) and the other formulae in which it appears, suitable combinations $-X^{20}-Ar^1-X^{21}-$ include
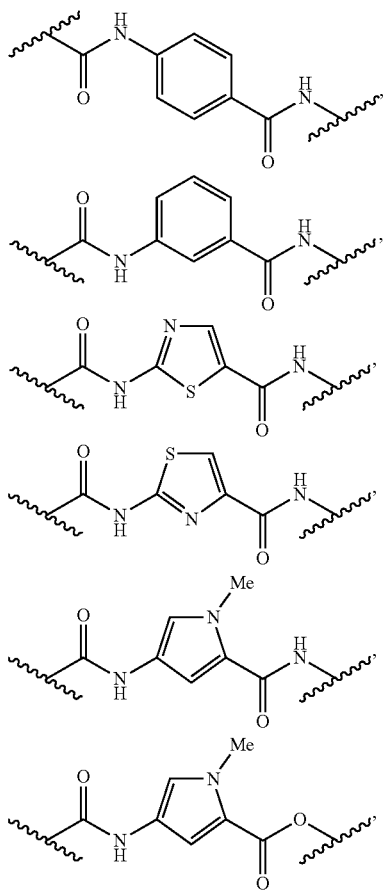
-continued
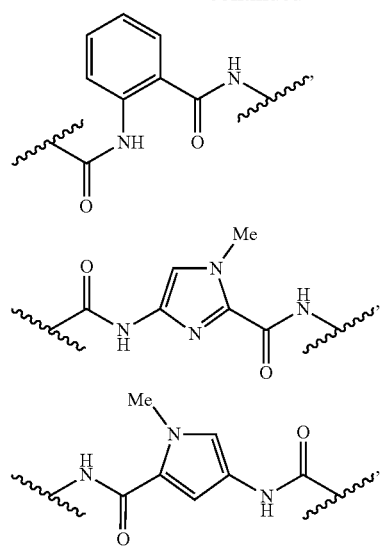
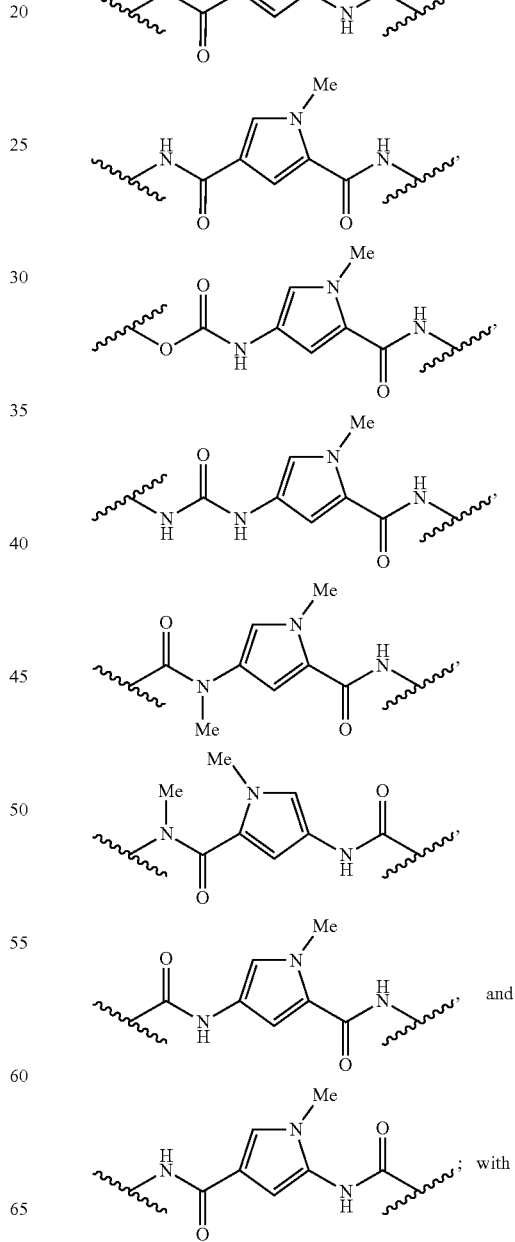

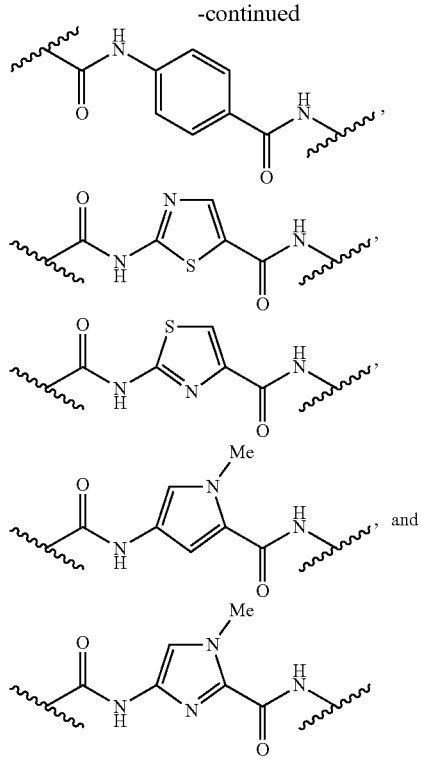
being preferred;
and with
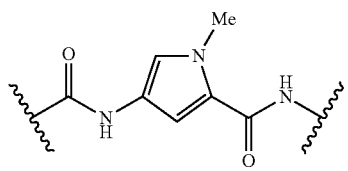 [SMILES: *NC(=O)c1cc(NC(*)=O)cn1C]
being especially preferred.
Suitable groups W include
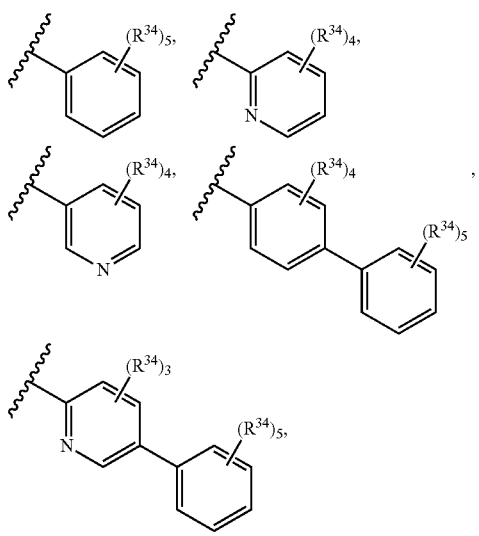
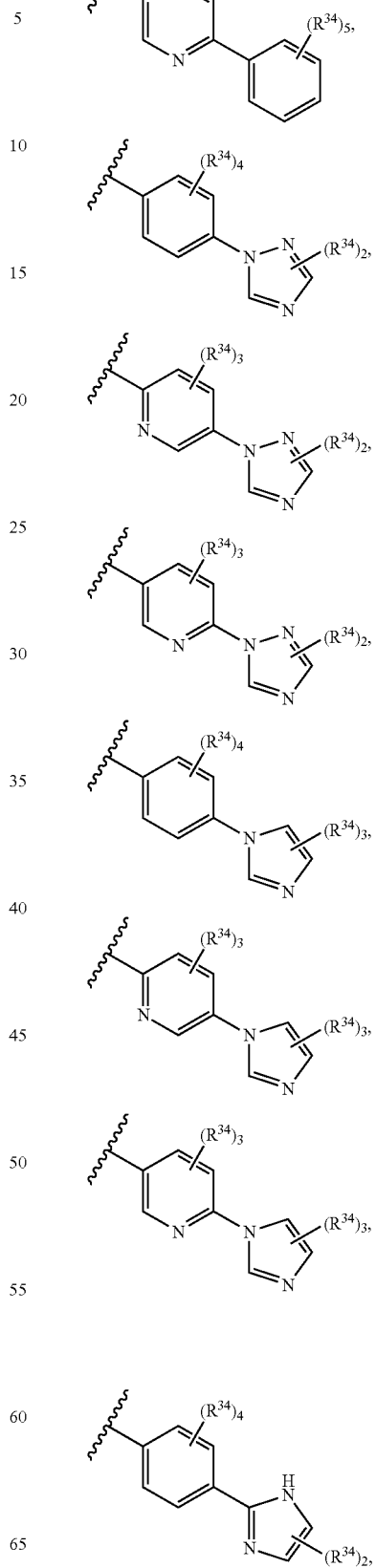

-continued

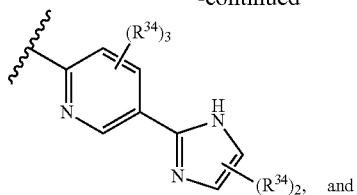

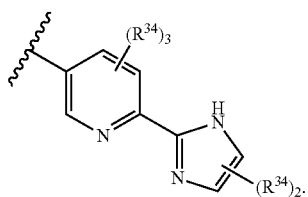

wherein each $R^{34}$ is independently H, $C_1$-$C_3$ alkyl, OH, Cl, F, $CH_2F$, $CHF_2$, $CF_3$, $O(C_1$-$C_3$ alkyl), $O(CH_2)_{2-4}OH$, $O(CH_2)_{0-2}CHF_2$, $C(=O)(C_1$-$C_3$ alkyl), $C(=O)O(C_1$-$C_3$ alkyl), $C(=O)NH_2$, $C(=O)NH(C_1$-$C_3$ alkyl), $C(=O)N(C_1$-$C_3$ alkyl)$_2$, $O(C_2$-$C_4$ alkenyl), $NH_2$, $NH(C_1$-$C_3$ alkyl), $N(C_1$-$C_3$ alkyl)$_2$, $O(CH_2)_{0-2}C_6H_5$, CN, or $NO_2$. Preferably, no more than one $R^{34}$ is other than H in any given aromatic ring.

Preferred groups W are:

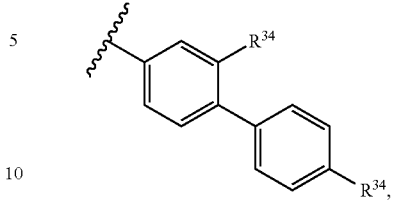

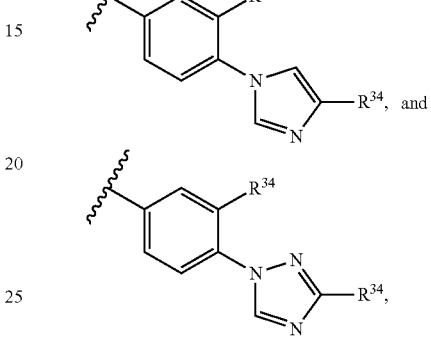

wherein each $R^{34}$ is independently as defined above.

In one aspect, compounds disclosed herein have a structure represented by formula (Ia'):

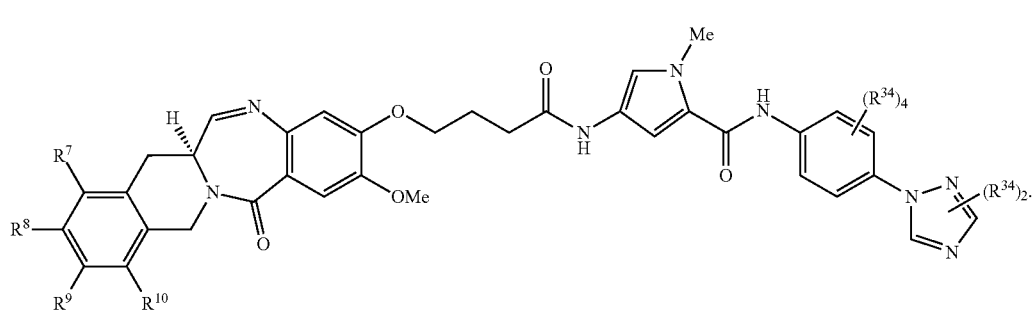

(Ia')

In another aspect, compounds disclosed herein have a structure represented by formula (Ia"):

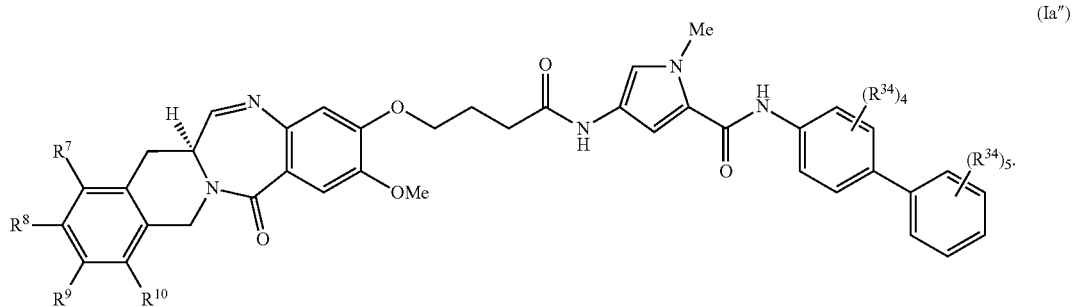

(Ia")

In yet another aspect, compounds disclosed herein have a structure represented by formula (Ia'''):

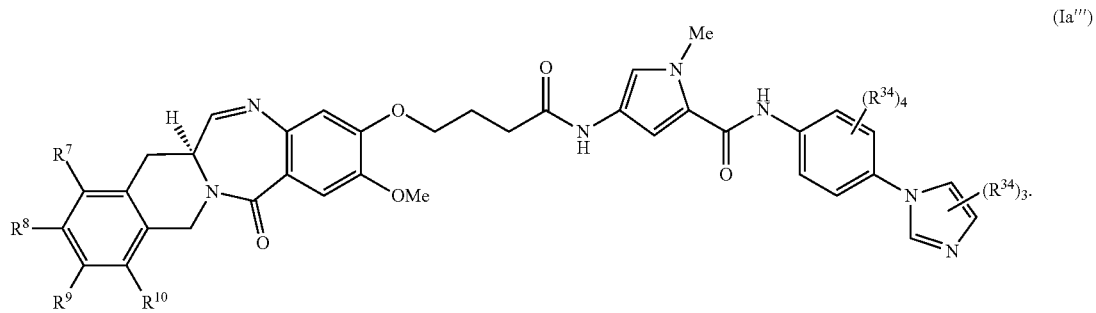

(Ia''')

In formulae (Ia'), (Ia''), and (Ia'''), $R^7$, $R^8$, $R^9$, $R^{10}$, and $R^{34}$ are as defined hereinabove.

An example of a compound according to formula (Ia') is compound (Ib-13) (see Table I hereinabove):

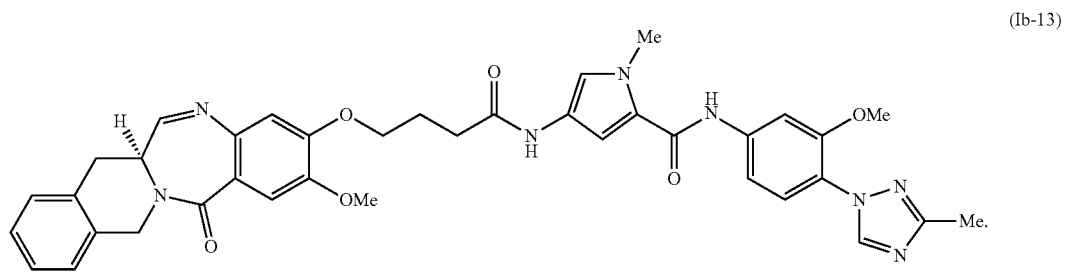 [SMILES: COc1cc2c(cc1OCCCC(=O)Nc1cc(C(=O)Nc3ccc(-n4cnc(C)n4)c(OC)c3)n(C)c1)N=C[C@@H]1Cc3ccccc3CN1C2=O]

(Ib-13)

An example of a compound according to formula (Ia'') is compound (Ib-54) (see Table I hereinabove):

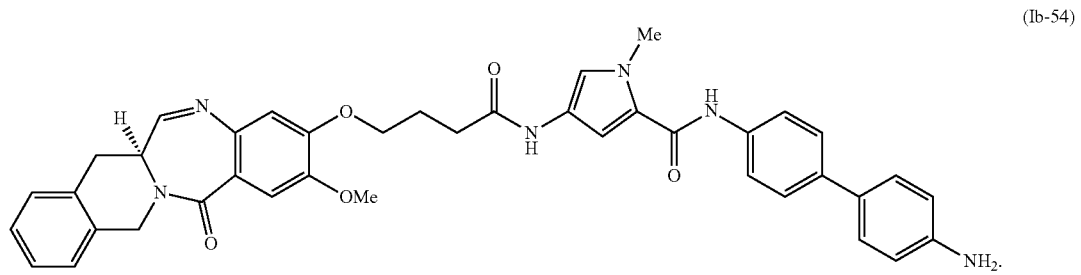 [SMILES: COc1cc2c(cc1OCCCC(=O)Nc1cc(C(=O)Nc3ccc(-c4ccc(N)cc4)cc3)n(C)c1)N=C[C@@H]1Cc3ccccc3CN1C2=O]

(Ib-54)

Examples of compounds according to formula (Ia''') are compounds (Ib-18), (Ib-19), (Ib-20), (Ib-21), and (Ib-22) from Table I.

Conjugates

General

Compounds disclosed herein can be used as therapeutic agents per se, but preferably are used as the drug component in conjugates. More preferably, the targeting moiety in the conjugate is an antibody or antigen binding portion thereof and its antigen is a tumor associated antigen, i.e., one that is expressed by a cancer cell. Preferably, the tumor associated antigen is uniquely expressed or overexpressed by the cancer cell, compared to a normal cell. The tumor associated antigen can be located on the surface of the cancer cell or secreted by the cancer cell into its environs.

In one aspect, there is provided a conjugate comprising compound of this invention and a ligand, represented by formula (II)

$$[D(X^D)_a(C)_c(X^Z)_b]_m Z \quad (II)$$

where Z is a targeting moiety, D is a compound of this invention, and —$(X^D)_a C(X^Z)_b$— are collectively referred to as a "linker moiety" or "linker" because they link Z and D. Within the linker, C is a cleavable group designed to be cleaved at or near the site of intended biological action of D; $X^D$ and $X^Z$ are spacer moieties (or "spacers") that space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

By binding to a target tissue or cell where its antigen or receptor is located, Z directs the conjugate there. Cleavage of group C at the target tissue or cell releases D to exert its cytotoxic effect locally. In some instances, the conjugate is internalized into a target cell by endocytosis and cleavage takes place within the target cell. In this manner, precise delivery of D is achieved at the site of intended action, reducing the dosage needed. Also, D is normally biologically inactive (or significantly less active) in its conjugated state, thereby reducing undesired toxicity against non-target tissue or cells.

As reflected by the subscript m, each Z can conjugate with more than one D, depending on the number of sites Z has available for conjugation and the experimental conditions employed. Those skilled in the art will appreciate that, while each individual Z is conjugated to an integer number of Ds, a preparation of the conjugate may analyze for a non-integer ratio of D to Z, reflecting a statistical average. This ratio is referred to as the substitution ratio ("SR") or the drug-antibody ratio ("DAR").

Targeting Moiety Z

Preferably, targeting moiety Z is an antibody. For convenience and brevity and not by way of limitation, the detailed discussion in this specification about Z and its conjugates is written in the context of its being an antibody, but those skilled in the art will understand that other types of Z can be conjugated, mutatis mutandis. For example, conjugates with folic acid as the targeting moiety can target cells having the folate receptor on their surfaces (Leamon et al., Cancer Res. 2008, 68 (23), 9839). For the same reasons, the detailed discussion in this specification is primarily written in terms of a 1:1 ratio of Z to D (m=1).

Preferably, Z is an antibody against a tumor associated antigen, allowing the selective targeting of cancer cells. Examples of such antigens include: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5Bla, 7D4, 7E4, 13B8, and 18D5); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2 (2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference.

In addition to being an antibody, Z can also be an antibody fragment (such as Fab, Fab', F(ab')$_2$, Fd, or Fv) or antibody mimetic, such as an antibody, a domain antibody (dAb), a nanobody, a unibody, a DARPin, an anticalin, a versabody, a duocalin, a lipocalin, or an avimer.

Any one of several different reactive groups on Z can be a conjugation site, including ε-amino groups in lysine residues, pendant carbohydrate moieties, carboxylic acid groups on aspartic or glutamic acid side chains, cysteine-cysteine disulfide groups, and cysteine thiol groups. For reviews on antibody reactive groups suitable for conjugation, see, e.g., Garnett, *Adv. Drug Delivery Rev.* 2001, 53, 171-216 and Dubowchik and Walker, *Pharmacology & Therapeutics* 1999, 83, 67-123, the disclosures of which are incorporated herein by reference.

Most antibodies have multiple lysine residues, which can be conjugated via their ε-amino groups via amide, urea, thiourea, or carbamate bonds.

In another embodiment, Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference.

In another embodiment, Z can be conjugated via an aspartic or glutamic acid side chain carboxylic acid, for example by conversion to a carbohydrazide, which is then reacted with an aldehyde-bearing linker. See Fisch et al., *Bioconjugate Chemistry* 1992, 3, 147-153.

A thiol (—SH) group in the side chain of a cysteine can be used to form a conjugate by several methods. It can be used to form a disulfide bond between it and a thiol group on the linker. Another method is via its Michael addition to a maleimide group on the linker.

Typically, although antibodies have cysteine residues, they lack free thiol groups because all their cysteines are engaged in intra- or inter-chain disulfide bonds. To generate a free thiol group, a native disulfide group can be reduced. See, e.g., Packard et al., *Biochemistry* 1986, 25, 3548; King et al., *Cancer Res.* 1994, 54, 6176; and Doronina et al., *Nature Biotechnol.* 2003, 21, 778. Alternatively, a cysteine having a free —SH group can be introduced by mutating the antibody, substituting a cysteine for another amino acid or inserting one into the polypeptide chain. See, for example, Eigenbrot et al., U.S. Pat. No. 7,521,541 B2 (2009); Chilkoti et al., *Bioconjugate Chem.* 1994, 5, 504; Urnovitz et al., U.S. Pat. No. 4,698,420 (1987); Stimmel et al., *J. Biol. Chem.* 2000, 275, 30445; Bam et al., U.S. Pat. No. 7,311,902 B2 (2007); Kuan et al., *J. Biol. Chem.* 1994, 269, 7610; Poon et al., *J. Biol. Chem.* 1995, 270, 8571; Junutula et al., *Nature Biotechnology* 2008, 26, 925 and Rajpal et al., U.S. Provisional Application No. 62/270,245, filed Dec. 21, 2015. In yet another approach, a cysteine is added to the C-terminus of the heavy of light chain. See, e.g., Liu et al., U.S. Pat. No. 8,865,875 B2 (2014); Cumber et al., *J. Immunol.* 1992, 149, 120; King et al, *Cancer Res.* 1994, 54, 6176; Li et al., *Bioconjugate Chem.* 2002, 13, 985; Yang et al., *Protein Engineering* 2003, 16, 761; and Olafson et al., *Protein Engineering Design & Selection* 2004, 17, 21. The disclosures of the documents cited in this paragraph are incorporated herein by reference.

Linkers and Their Components

As noted above, the linker comprises up to three elements: a cleavable group C and optional spacers $X^Z$ and $X^D$.

Group C is cleavable under physiological conditions. Preferably it is relatively stable while the conjugate is in circulation in the blood, but is readily cleaved once the conjugate reaches its site of intended action, near, at, or within the target cell. Preferably, the conjugate is internalized by a target cell upon binding of an antibody Z to an antigen displayed on the surface of the target cell. Subsequently, cleavage of C occurs in a vesicular body of the target cell (an early endosome, a late endosome, or, especially, a lysosome).

In one embodiment, C is a pH sensitive group. The pH in blood plasma is slightly above neutral, while the pH inside a lysosome is acidic, circa 5. Thus, an acid-sensitive C will cleave at a rate several orders of magnitude faster inside a lysosome than in blood. Examples of acid-sensitive groups are cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 1981, 102, 1048; and Yang et al., *Proc. Natl Acad. Sci (USA)* 1988, 85, 1189; the disclosures of which are incorporated herein by reference.

In another embodiment, C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. See, e.g., Thorpe et al., *Cancer Res.* 2008, 48, 6396-6403; Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2 (2010); and Sufi et al., U.S. Pat. No. 8,461,117 B2 (2013); the disclosures of which are incorporated herein by reference.

A preferred group C is a peptide that is cleaved selectively by a protease inside the target cell, as opposed to by a protease in the serum. Typically, the peptide comprises from 1 to 20 amino acids, preferably from 1 to 6 amino acids, more preferably from 2 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this specification, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of a cancer, e.g., a protease released by nearby dying cancer cells or a tumor-associated protease secreted by cancer cells. Exemplary extracellular tumor-associated proteases are plasmin, matrix metalloproteases (MMP), thimet oligopeptidase (TOP) and CD10. See, e.g., Trouet et al., U.S. Pat. No. 7,402,556 B2 (2008); Dubois et al., U.S. Pat. No. 7,425,541 B2 (2008); and Bebbington et al., U.S. Pat. No. 6,897,034 B2 (2005).

For conjugates designed to be internalized by a cell, C preferably comprises an amino acid sequence selected for cleavage by an endosomal or lysosomal protease, especially the latter. Non-limiting examples of such proteases include cathepsins B, C, D, H, L and S, especially cathepsin B. Exemplary cathepsin B cleavable peptides include Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit. (Herein, amino acid sequences are written in the N-to-C direction, as in $H_2N$-$AA^2$-$AA^1$-$CO_2H$, unless the context clearly indicates otherwise.) See Dubowchik et al., *Biorg. Med. Chem. Lett.* 1998, 8, 3341; Dubowchik et al., *Bioorg. Med. Chem. Lett.* 1998, 8, 3347; and Dubowchik et al., *Bioconjugate Chem.* 2002, 13, 855; the disclosures of which are incorporated by reference.

Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu. More preferably, it is a two to three amino acid peptide from the foregoing group.

The preparation and design of cleavable groups C consisting of a single amino acid is disclosed in Chen et al., U.S. Pat. No. 8,664,407 B2 (2014), the disclosure of which is incorporated herein by reference.

Group C can be bonded directly to Z or D; i.e. spacers $X^Z$ or $X^D$, as the case may be, can be absent.

When present, spacer $X^Z$ provides spatial separation between C and Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

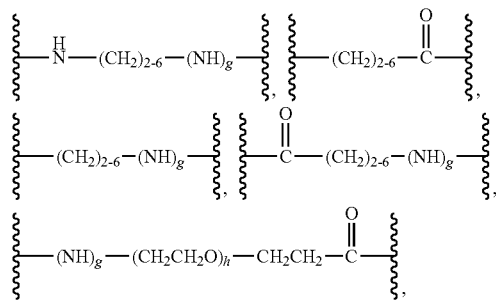

and combinations thereof,
where the subscript g is 0 or 1 and the subscript h is 1 to 24, preferably 2 to 4. These segments can be combined, such as illustrated below:

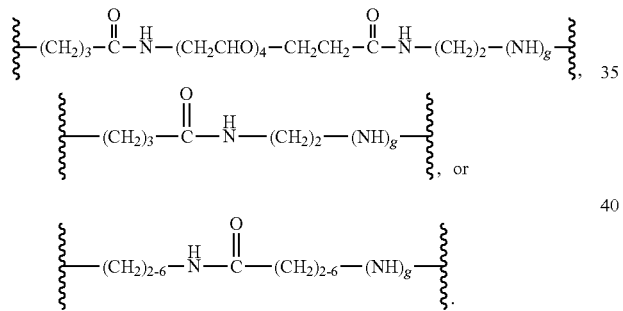

Spacer $X^D$, if present, provides spatial separation between C and D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, analogously to the description above for spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain a poly(ethylene glycol) ("PEG") group. Since the conjugation step typically involves coupling a drug-linker to an antibody in an aqueous medium, a PEG group many enhance the aqueous solubility of the drug-linker. Also, a PEG group may enhance the solubility or reduce aggregation in the resulting ADC. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to C and either Z or D and (2) has a structure such that cleavage from group C initiates a reaction sequence resulting in the self-immolating moiety disbonding itself from Z or D, as the case may be. In other words, reaction at a site distal from Z or D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to D, the biological activity of D may be impaired. The use of a self-immolating moiety is especially desirable where cleavable group C is a polypeptide, in which instance the self-immolating moiety typically is located adjacent thereto, in order to prevent D from sterically or electronically interfering with peptide cleavage.

Exemplary self-immolating moieties (i)-(v) bonded to a hydroxyl or amino group of D are shown below:

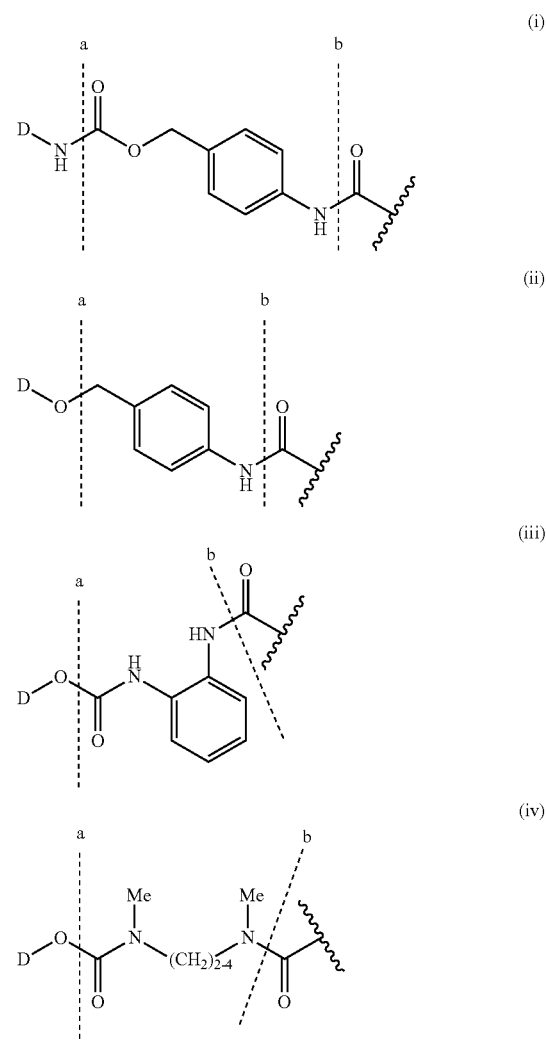

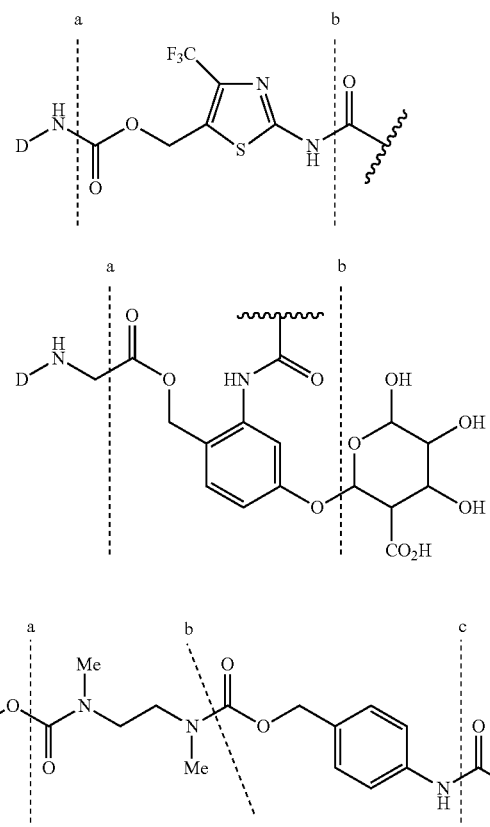

(v)

(vi)

(vii)

The self-immolating moiety is the structure between dotted lines a and b (or dotted lines b and c), with adjacent structural features shown to provide context. Self-immolating moieties (i) and (v) are bonded to a D-NH$_2$ (i.e., conjugation is via an amino group), while self-immolating moieties (ii), (iii), and (iv) are bonded to a D-OH (i.e., conjugation is via a hydroxyl or carboxyl group). Cleavage of the bond at dotted line b by an enzyme—a peptidase in the instance of structures (i)-(v) and a β-glucuronidase in the instance of structure (vi)—initiates a self-immolating reaction sequence that results in the cleavage of the bond at dotted line a and the consequent release of D-OH or D-NH$_2$, as the case may be. By way of illustration, self-immolating mechanisms for structures (i) and (iv) are shown below:

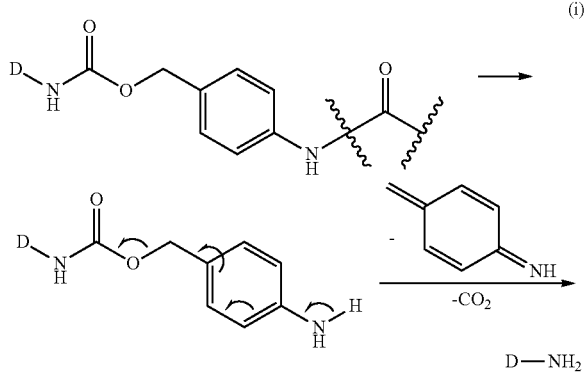

(i)

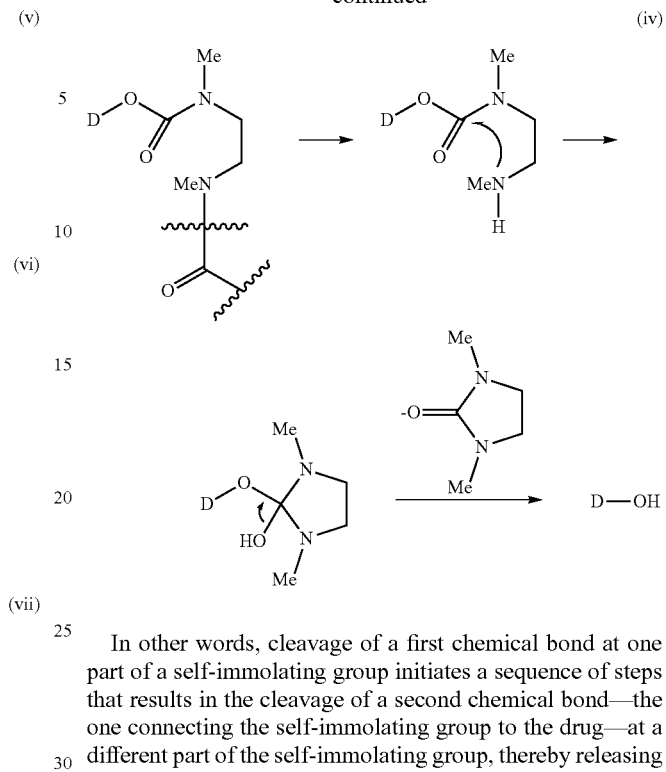

(iv)

In other words, cleavage of a first chemical bond at one part of a self-immolating group initiates a sequence of steps that results in the cleavage of a second chemical bond—the one connecting the self-immolating group to the drug—at a different part of the self-immolating group, thereby releasing the drug.

In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.* 1981, 24, 479; Carl et al., WO 81/01145 (1981); Dubowchik et al., *Pharmacology & Therapeutics* 1999, 83, 67; Firestone et al., U.S. Pat. No. 6,214,345 B1 (2001); Toki et al., *J. Org. Chem.* 2002, 67, 1866; Doronina et al., *Nature Biotechnology* 2003, 21, 778 (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference.

In another embodiment, Z and D are linked by a non-cleavable linker, i.e., C is absent. Metabolism of D eventually reduces the linker to a small appended moiety that does not interfere with the biological activity of D.

Conjugation Techniques

Conjugates of compounds disclosed herein preferably are made by first preparing a compound comprising D and linker $(X^D)_a(C)_c(X^Z)_b$ (where $X^D$, C, $X^Z$, a, b, and c are as defined for formula (II)) to form drug-linker compound represented by formula (III):

$$D\text{-}(X^D)_a(C)_c(X^Z)_b\text{—}R^{31} \qquad (III)$$

where $R^{31}$ is a functional group suitable for reacting with a complementary functional group on Z to form the conjugate. Examples of suitable groups $R^{31}$ include amino, azide, thiol, cyclooctyne,

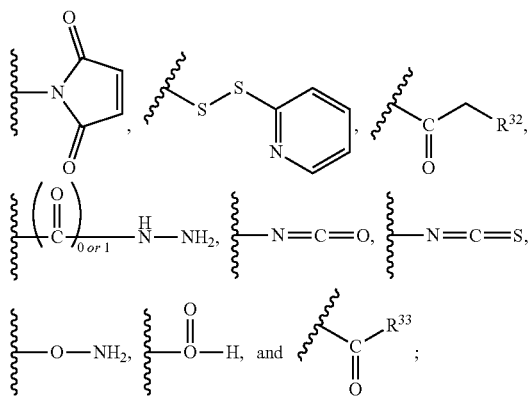

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D-(X^D)_a C(X^Z)_b-R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., U.S. Pat. No. 8,461,117 B2 (2013); and Chen et al., U.S. Pat. No. 8,664,407 B2 (2014); the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido. Especially preferred functional groups —$R^{31}$ are:

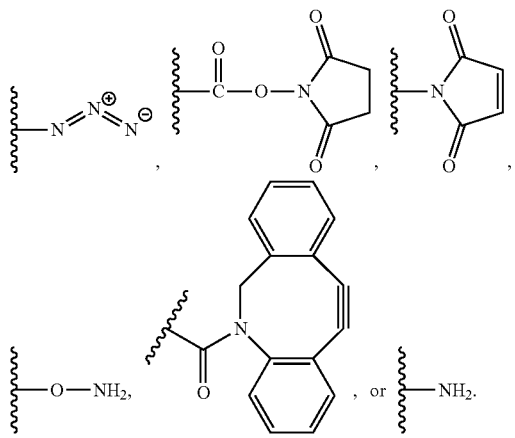

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Where an antibody does not have a cysteine —SH available for conjugation, an E-amino group in the side chain of a lysine residue can be reacted with 2-iminothiolane or N-succinimidyl-3-(2-pyridyldithio)propionate ("SPDP") to introduce a free thiol (—SH) group—creating a cysteine surrogate, as it were. The thiol group can react with a maleimide or other nucleophile acceptor group to effect conjugation. The mechanism if illustrated below with 2-iminothiolane.

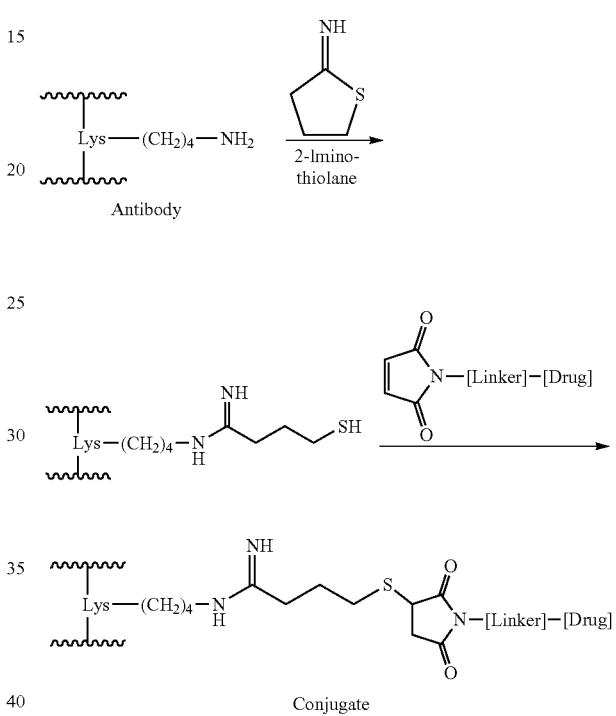

Typically, a thiolation level of two to three thiols per antibody is achieved. For a representative procedure, see Cong et al., U.S. Pat. No. 8,980,824 B2 (2015), the disclosure of which is incorporated herein by reference.

In a reversed arrangement, an antibody Z can be modified with N-succinimidyl 4-(maleimidomethyl)-cyclohexanecarboxylate ("SMCC") or its sulfonated variant sulfo-SMCC, both of which are available from Sigma-Aldrich, to introduce a maleimide group thereto. Then, conjugation can be effected with a drug-linker compound having an —SH group on the linker.

An alternative conjugation method employs copper-free "click chemistry," in which an azide group adds across a strained cyclooctyne to form an 1,2,3-triazole ring. See, e.g., Agard et al., J. Amer. Chem. Soc. 2004, 126, 15046; Best, Biochemistry 2009, 48, 6571, the disclosures of which are incorporated herein by reference. The azide can be located on the antibody and the cyclooctyne on the drug-linker moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

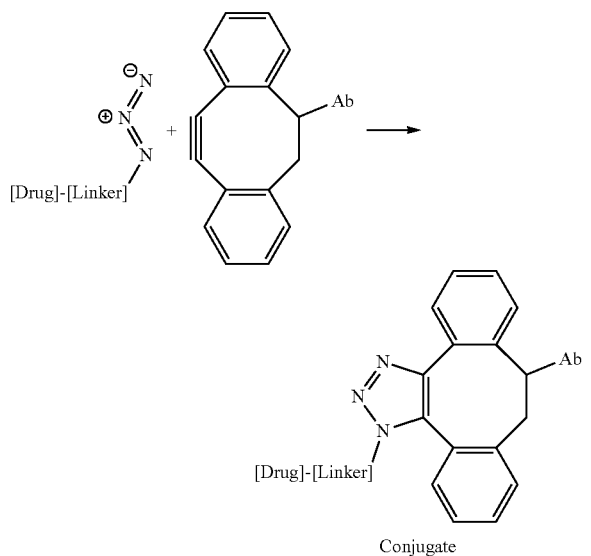

Conjugate

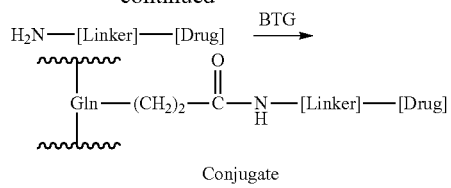

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., Biotechnol. Bioeng. 2009, 102 (2), 400-416. The foregoing disclosures are incorporated herein by reference. Thus, in one embodiment, an antibody that is used for making a conjugate has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase from *Streptomyces mobaraensis* or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

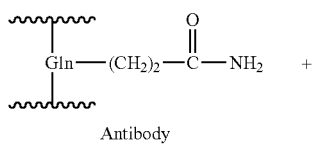

Antibody

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest," 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution not only eliminates glycosylation, but also introduces a second glutamine residue (at position 297) that too is an amine acceptor. Thus, in one embodiment, the antibody is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., WO 2016/144608 A1.

In a complementary approach, the substrate specificity of BTG can be altered by varying its amino acid sequence, such that it becomes capable of reacting with glutamine 295 in an umodified antibody, as taught in Rao-Naik et al., PCT Application PCT/US2016/054585, filed 30 Sep. 2016.

While the most commonly available bacterial transglutaminase is that from *S. mobaraensis*, transglutaminase from other bacteria, having somewhat different substrate specificities, can be considered, such as transglutaminase from *Streptoverticillium ladakanum* (Hu et al., US 2009/0318349 A1 (2009), US 2010/0099610 A1 (2010), and US 2010/0087371 A1 (2010)).

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

Drug-Linker Compounds

Generally, an ADC comprises a linker attached to a functional group on the drug, which linker is attached in turn to the antibody. Reflecting the diversity of conjugation techniques available, the drugs can be elaborated into many different drug-linker compounds suitable for conjugation to an antibody.

There are three different positions ((a), (b), and (c)) for attachment of the linker to compounds disclosed herein, as illustrated below (with variables and optional substituents not shown for simplicity):

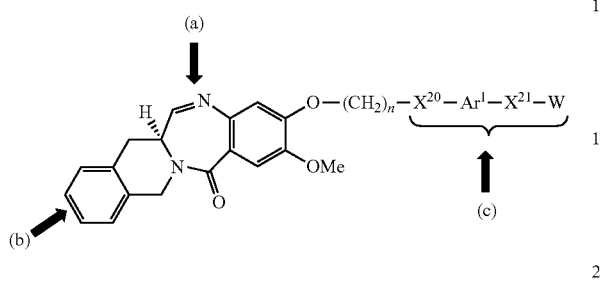

Linker attachment at position (a) entails forming an addition product (A) across the imine double bond, comprising a carbamate group. Cleavage of the linker at the dotted line leads to intermediate (B), whose unstable carbamic acid group decarboxylates to produce a geminal amino alcohol (C). Dehydration of the latter regenerates the benzodiazepine ring system (D).

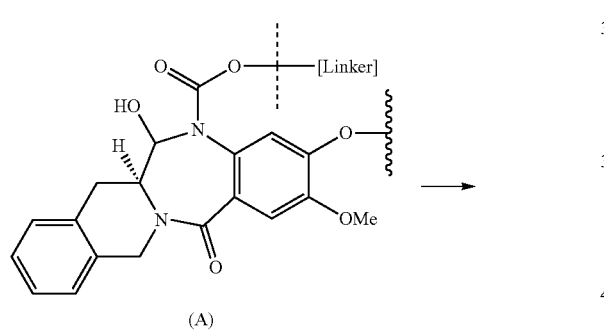

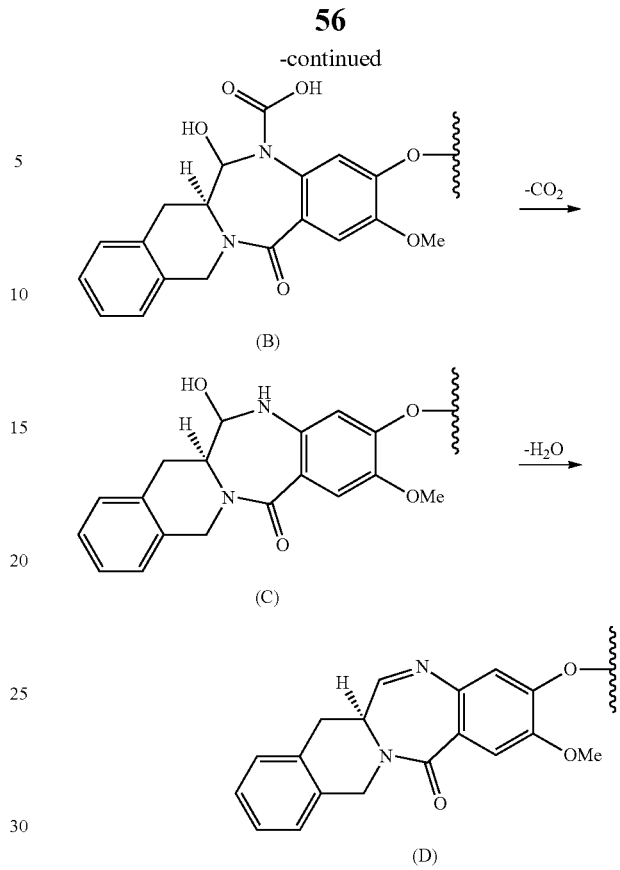

For conjugation at position (b), a suitable functional group such as amino ($NH_2$) or hydroxyl (OH) can be situated at the flanking benzene ring.

For conjugation at position (c), a suitable functional group such as amino ($NH_2$) or hydroxyl (OH) can be situated at $Ar^1$ or W, preferable at W.

Thus, there is provided a drug-linker compound having a structure represented by formula (IIIa), (IIIb), or (IIIc)

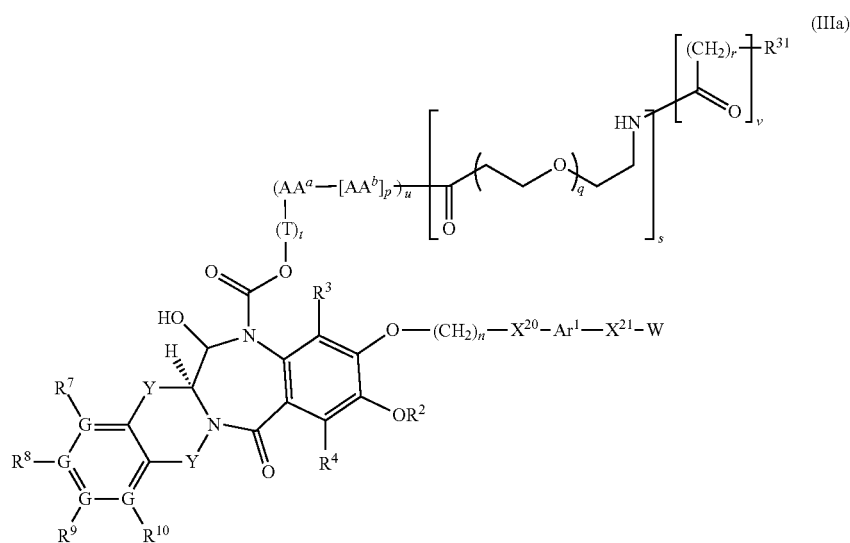

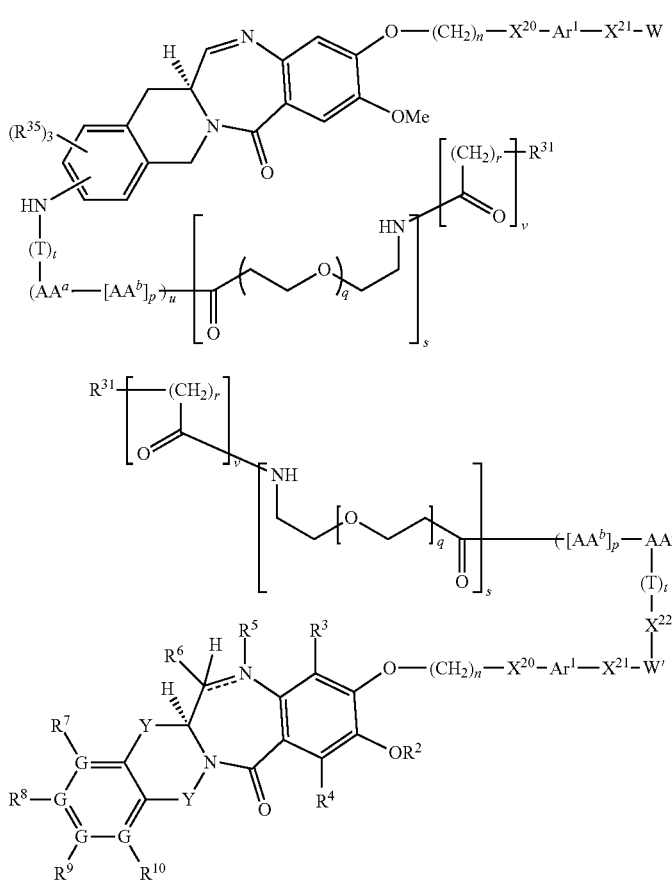

(IIIb)

(IIIc)

wherein

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

u is 0 or 1;

p is 1, 2, 3, or 4;

q is 1, 2, 3, 4, 5, 6, 7, 8, 9, 10, 11, or 12;

r is 1, 2, 3, 4, or 5;

s is 0 or 1;

v is 0 or 1;

$R^{31}$ is H,

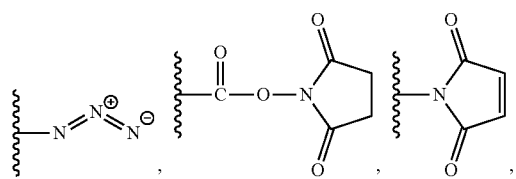

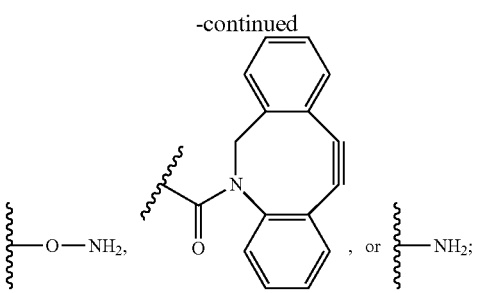

with the provisos that $R^{31}$ can be H only if s is 1 and v is 0 and that v can be 0 only if s is 1 and $R^{31}$ is H;

each G is C or N, with the proviso that no more than two Gs are N;

$R^2$ is H or $C_1$-$C_5$ alkyl;

$R^3$ and $R^4$ are independently H, F, Cl, Br, OH, $C_1$-$C_3$ alkyl, $O(C_1$-$C_3$ alkyl), cyano, $(CH_2)_{0-5}NH_2$, or $NO_2$;

the double line ----- in the diazepine ring system represents a single bond or a double bond;

$R^5$ is H if the double line ----- is a single bond and is absent if the double line ----- is a double bond;

$R^6$ is H, OH, $SO_3Na$, or $SO_3K$ if the double line ----- is a single bond and is absent if the double line ----- is a double bond;

$R^7$, $R^8$, $R^9$, and $R^{10}$ are independently H, $C_1$-$C_5$ alkyl, $C\equiv C(CH_2)_{1-5}X^2$, OH, $O(C_1$-$C_5$ alkyl), cyano, $NO_2$, F, Cl, Br, O(CH$_2$CH$_2$O)$_{1-8}$(C$_{1-3}$ alkyl), (CH$_2$)$_{0-5}$X$^2$, O(CH$_2$)$_{2-5}$X$^2$, 3- to 7-membered cycloalkyl or heterocycloalkyl unsubstituted or substituted with (CH$_2$)$_{0-5}$X$^2$ or O(CH$_2$)$_{2-5}$X$^2$, phenyl unsubstituted or substituted with (CH$_2$)$_{0-5}$X$^2$ or O(CH$_2$)$_{2-5}$X$^2$, 5- to 6-membered heteroaryl unsubstituted or substituted with (CH$_2$)$_{0-5}$X$^2$ or O(CH$_2$)$_{2-5}$X$^2$,

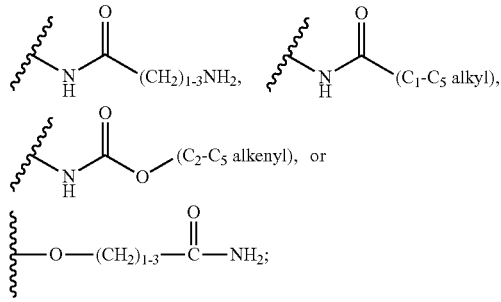

or where a R$^7$, R$^8$, R$^9$, or R$^{10}$ is attached to a G that is N, such R$^7$, R$^8$, R$^9$, or R$^{10}$ is absent;

each X$^2$ is independently H, F, Cl, Br, OH, O(C$_1$-C$_3$ alkyl), O(C$_1$-C$_3$ alkylene), CO$_2$H, N$_3$, CN, NO$_2$, CO$_2$(C$_1$-C$_3$ alkyl), NH$_2$, NH(C$_1$-C$_5$ alkyl), N(C$_1$-C$_5$ alkyl)$_2$, SH, CHO, N(CH$_2$CH$_2$)$_2$N(C$_1$-C$_3$ alkyl), NHNH$_2$, or C(=O)NHNH$_2$;

each Y is independently CH$_2$, C=O, or CHR$^{12}$; wherein each R$^{12}$ is independently F, Cl, Br, or C$_1$-C$_3$ alkyl;

n is 2, 3, 4, 5, or 6;

X$^{20}$ and X$^{21}$ are independently

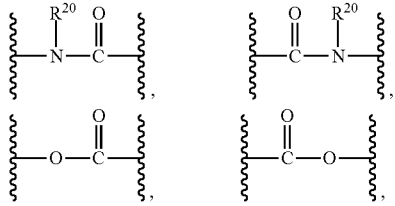

-continued

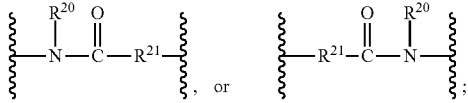

wherein R$^{20}$ is H or C$_1$-C$_3$ alkyl and R$^{21}$ is O, NH, or N(C$_1$-C$_3$ alkyl);

Ar$^1$ is (i) a phenyl moiety, (ii) a 5- or 6-membered heteroaromatic moiety, or (iii) a polycyclic aromatic moiety comprising a phenyl or 6-membered heteroaromatic ring fused to a phenyl ring or a 5- or 6-membered heteroaromatic ring; each phenyl, heteroaromatic, or polycyclic aromatic moiety being optionally substituted with one or more of C$_1$-C$_6$ alkyl, Cl, or F;

W is (a) C$_1$-C$_6$ alkyl or C$_3$-C$_6$ cycloalkyl or (b) an aromatic moiety comprising one to three (i) phenyl or (ii) 5- or 6-membered heteroaromatic rings, which phenyl or 5- or 6-membered heteroaromatic rings are optionally substituted with one or more of C$_1$-C$_3$ alkyl, OH, Cl, F, CH$_2$F, CHF$_2$, CF$_3$, O(C$_1$-C$_3$ alkyl), O(CH$_2$)$_{2-4}$OH, O(CH$_2$)$_{0-2}$CHF$_2$, C(=O)(C$_1$-C$_3$ alkyl), C(=O)O(C$_1$-C$_3$ alkyl), C(=O)NH$_2$, C(=O)NH(C$_1$-C$_3$ alkyl), C(=O)N(C$_1$-C$_3$ alkyl)$_2$, O(C$_2$-C$_4$ alkenyl), NH$_2$, NH(C$_1$-C$_3$ alkyl), N(C$_1$-C$_3$ alkyl)$_2$, O(CH$_2$)$_{0-2}$C$_6$H$_5$, CN, or NO$_2$; wherein, if more than one phenyl or 5- or 6-membered heteroaromatic ring is present, such rings are fused to each other or joined by an aryl-aryl bond;

each R$^{35}$ is independently H, Cl, F, Br, C$_1$-C$_5$ alkyl, O(C$_1$-C$_5$ alkyl), OH, CN, NO$_2$, NH(C=O)(C$_1$-C$_5$ alkyl), N(C$_1$-C$_5$ alkyl)$_2$, or CF$_3$;

X$^{22}$ is O or NH;

W' is an aromatic moiety comprising one to three (i) phenyl or (ii) 5- or 6-membered heteroaromatic rings, which phenyl or 5- or 6-membered heteroaromatic rings are optionally substituted with one or more of C$_1$-C$_3$ alkyl, OH, Cl, F, CH$_2$F, CHF$_2$, CF$_3$, O(C$_1$-C$_3$ alkyl), O(CH$_2$)$_{2-4}$OH, O(CH$_2$)$_{0-2}$CHF$_2$, C(=O)(C$_1$-C$_3$ alkyl), C(=O)O(C$_1$-C$_3$ alkyl), C(=O)NH$_2$, C(=O)NH(C$_1$-C$_3$ alkyl), C(=O)N(C$_1$-C$_3$ alkyl)$_2$, O(C$_2$-C$_4$ alkenyl), NH$_2$, NH(C$_1$-C$_3$ alkyl), N(C$_1$-C$_3$ alkyl)$_2$, O(CH$_2$)$_{0-2}$C$_6$H$_5$, CN, or NO$_2$; wherein, if more than one phenyl or 5- or 6-membered heteroaromatic ring is present, such rings are fused to each other or joined by an aryl-aryl bond;

or a salt thereof.

Formulae (IIIa), (IIIb), and (IIIc) represent type (a), type (b), and type (c) drug-linker compounds, respectively.

A preferred drug-linker compound according to formula (IIIa) has a structure represented by formula (IIIa')

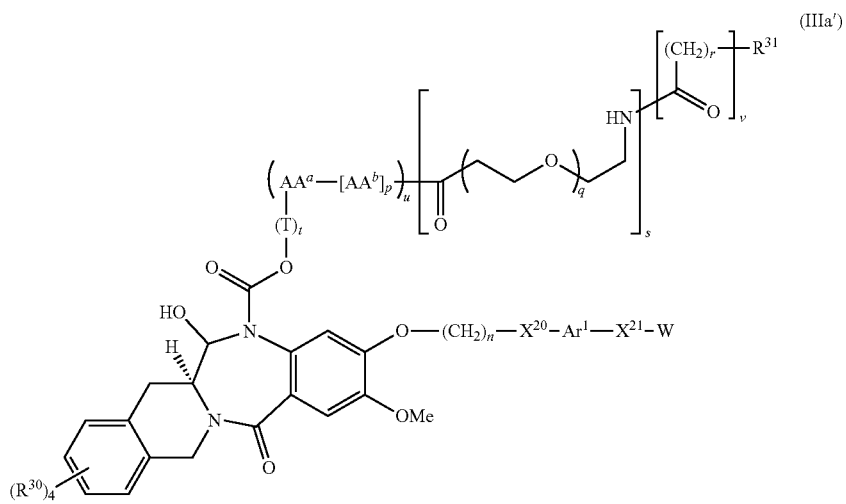

wherein each $R^{30}$ is independently H, Cl, F, Br, $C_1$-$C_5$ alkyl, O($C_1$-$C_5$ alkyl), OH, CN, $NO_2$, NH(C=O)($C_1$-$C_5$ alkyl), N($C_1$-$C_5$ alkyl)$_2$, or $CF_3$.

Preferably, each $R^{30}$ is H in formula (IIIa').

Another preferred drug-linker compounds of type (a) according to formula (IIIa) has a structure represented by formula (IIIa")

The moiety -AA$^a$-[AA$^b$]$_p$- in formula (IIIa) or (IIIa') represents a polypeptide whose length is determined by the value of p (dipeptide if p is 1, tetrapeptide if p is 3, etc.). AA$^a$ is at the carboxy terminus of the polypeptide and its carboxyl group forms a peptide (amide) bond with an amine nitrogen of the drug compound. Conversely, the last AA$^b$ is at the amino terminus of the polypeptide and its α-amino group forms a peptide bond with

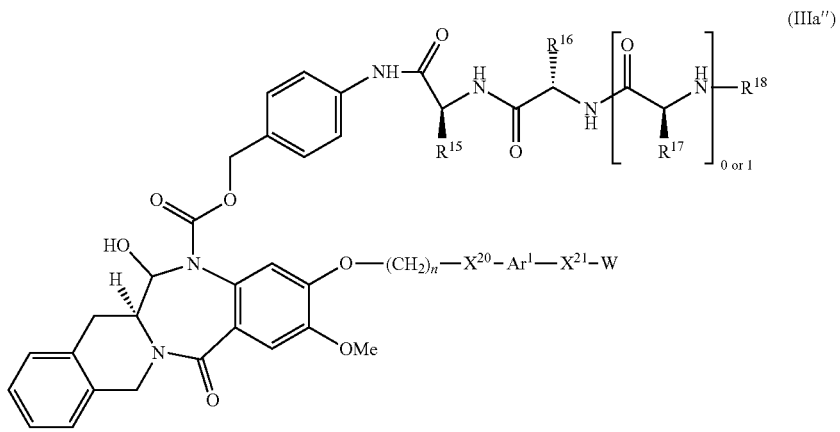

(IIIa")

wherein $R^{15}$, $R^{16}$ and $R^{17}$ are independently H, $CH_3$, $CH(CH_3)_2$, $CH_2CO_2H$, $CH_2CH_2CO_2H$, $CH_2C(=O)NH_2$, $CH_2CH_2C(=O)NH_2$, $(CH_2)_4NH_2$, $(CH_2)_3NHC(=NH)NH_2$ or $(CH_2)_3NHC(=O)NH_2$;

and $R^{18}$ is

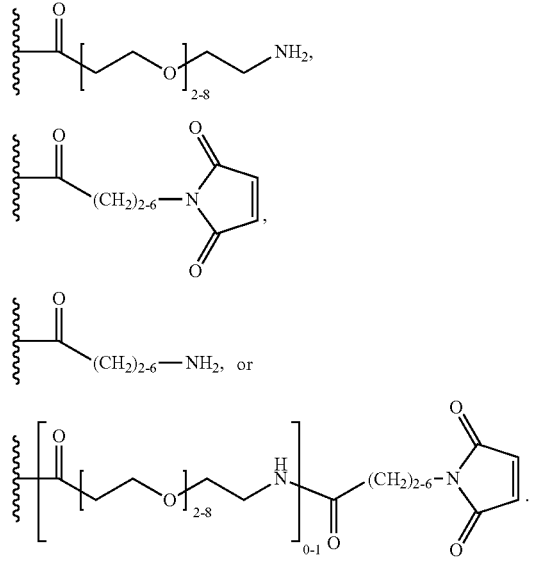

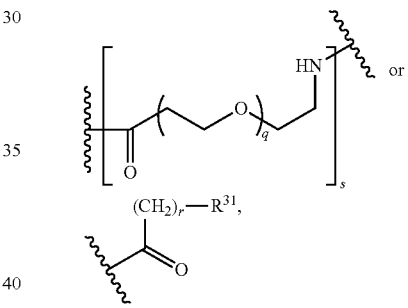

depending on whether s is 1 or 0, respectively. Preferred polypeptides -AA$^a$-[AA$^b$]$_p$- are Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in $H_2$N-Val-Cit-$CO_2$H). More preferably, the polypeptide is Val-Cit, Val-Lys, or Val-Ala. Preferably, a polypeptide -AA$^a$-[AA$^b$]$_p$- is cleavable by an enzyme found inside the target (cancer) cell, for example a cathepsin and especially cathepsin B.

As indicated by the subscript t equals 0 or 1, a self-immolating group T in formula (IIIa) or (IIIa') is optionally present. When present, the self-immolating group T preferably is a p-aminobenzyl oxycarbonyl (PABC) group, whose structure is shown below, with an asterisk (*) denoting the end of the PABC bonded to the imine nitrogen of the benzodiazepine ring and a wavy line (〰) denoting the end bonded to the polypeptide -AA$^a$-[AA$^b$]$_p$-.

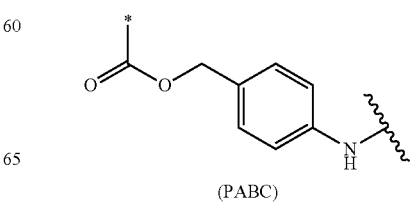

(PABC)

That is, $R^{11}$, $R^{12}$, and $R^{13}$ in formula (IIIa") correspond to the side chain residues of the amino acids glycine, valine, aspartic acid, glutamic acid, asparagine, glutamine, lysine, arginine, and citrulline, respectively.

In one embodiment, u is 1 in formula (IIIa) or (IIIa').

In a preferred embodiment, in formula (IIIa) or (IIIa') the group $R^{31}$ is

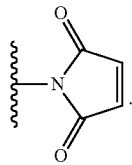

In another preferred embodiment, in formula (IIIa) or (IIIa') the group $R^{31}$ is

or $R^{31}$ is H while v is 0 and s is 1. In each case, the result is a drug-linker compound that has an amino-terminal group, of the structure

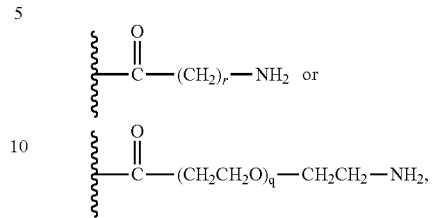

respectively, which is suitable as an amine donor for a transglutaminase-mediated conjugation.

The preferred embodiments for u, moiety $-AA^a-[AA^b]_p-$, the self-immolating group T, and the group $R^{31}$ discussed hereinabove in respect of type (a) drug-linker compounds also apply to type (b) and type (c) drug-linker compounds.

Examples of type (a) drug-linker compounds have structures represented by formulae (IIIa-01) and (IIIa-02):

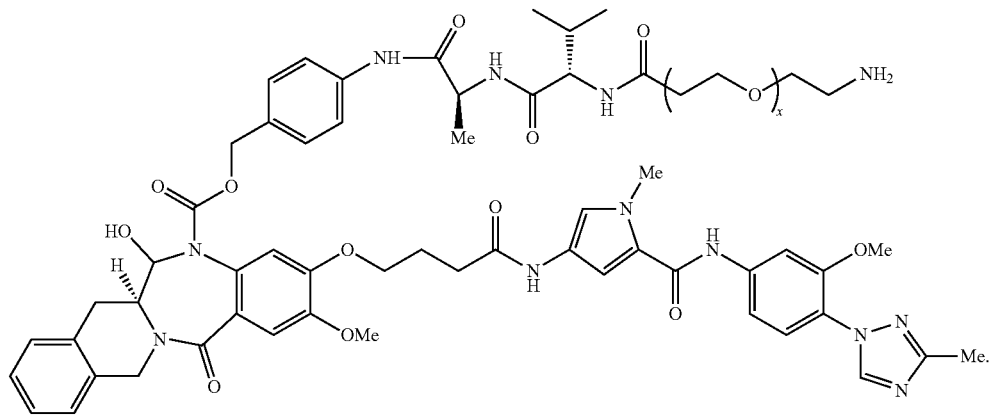

(IIIa-01) x = 4
(IIIa-02) x = 2

A preferred type (c) drug-linker compound according to formula (IIIc) has a structure represented by formula (IIIc'):

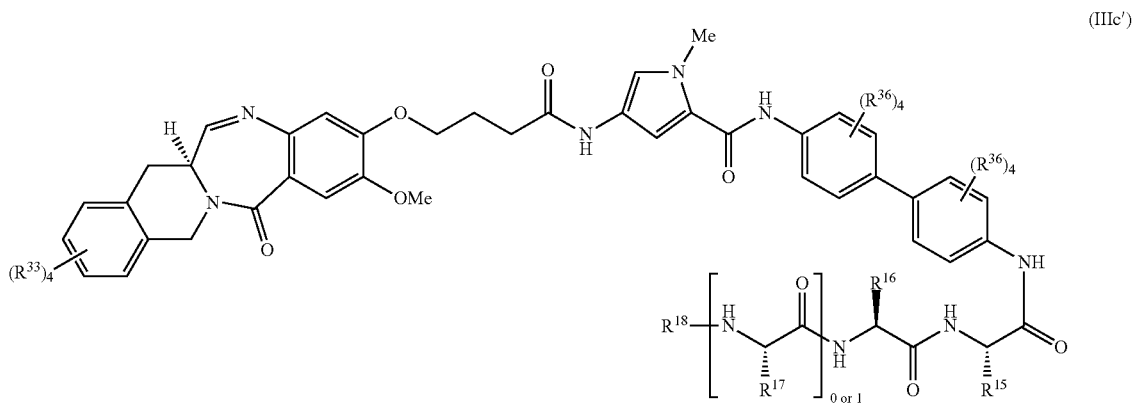

(IIIc')

wherein
R$^{15}$, R$^{16}$, R$^{17}$, and R$^{18}$ are as defined hereinabove in respect of formula (IIIa'');
each R$^{33}$ is independently H, Cl, F, Br, C$_1$-C$_5$ alkyl, O(C$_1$-C$_5$ alkyl), OH, CN, NO$_2$, NH(C=O)(C$_1$-C$_5$ alkyl), N(C$_1$-C$_5$ alkyl)$_2$, or CF$_3$ (with each R$^{33}$ preferably being H); and
each R$^{36}$ is independently H, C$_1$-C$_3$ alkyl, OH, Cl, F, CH$_2$F, CHF$_2$, CF$_3$, O(C$_1$-C$_3$ alkyl), O(CH$_2$)$_{2-4}$OH, O(CH$_2$)$_{0-2}$CHF$_2$, C(=O)(C$_1$-C$_3$ alkyl), C(=O)O(C$_1$-C$_3$ alkyl), C(=O)NH$_2$, C(=O)NH(C$_1$-C$_3$ alkyl), C(=O)N(C$_1$-C$_3$ alkyl)$_2$, O (C$_2$-C$_4$ alkenyl), O(CH$_2$)$_{0-2}$C$_6$H$_5$, CN, or NO$_2$ (with each R$^{36}$ preferably being H).

and

Examples of type (c) drug-linker compound are (IIIc-01) and (IIIc-02):

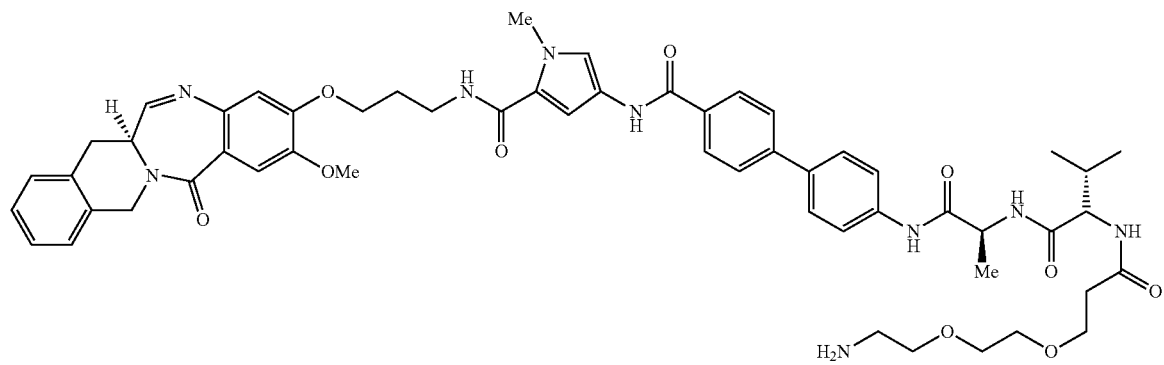

(IIIc-01)

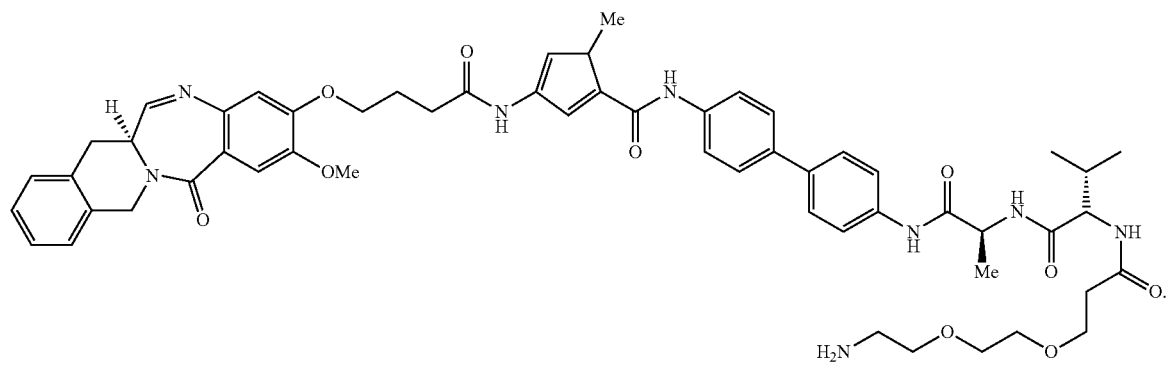

(IIIc-02)

Conjugates
In one aspect, there is provided a conjugate, having a structure represented by formula (IVa), (IVb), or (IVc)
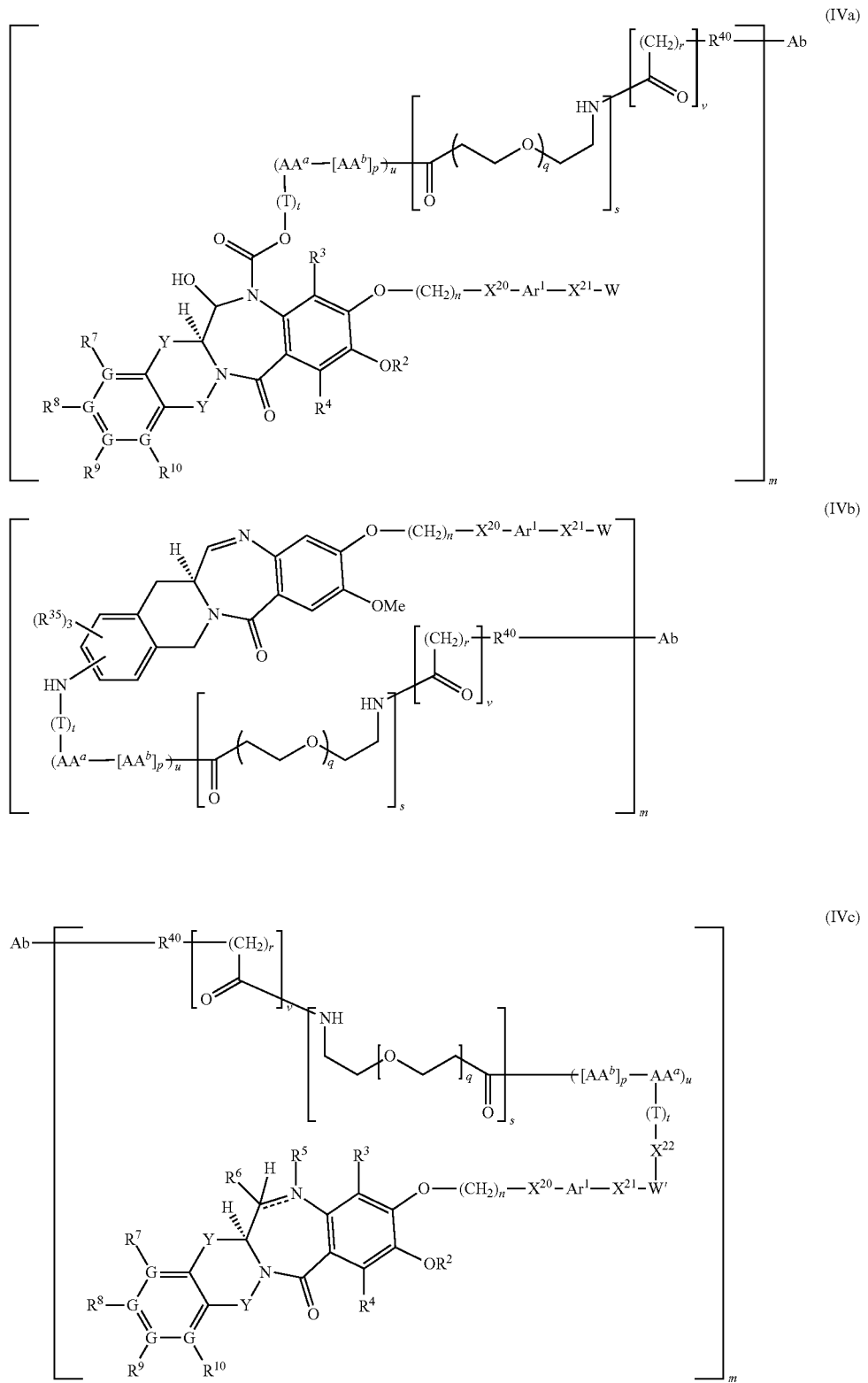

wherein

Ab is an antibody;

m is 1, 2, 3, or 4;

T is a self-immolating group;

t is 0 or 1;

AA$^a$ and each AA$^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

u is 0 or 1;

p is 1, 2, 3, or 4;

q is 1, 2, 3, 4, 5, 6, 7, 8, 9, 10, 11, or 12;

r is 1, 2, 3, 4, or 5;

s is 0 or 1;

$R^{40}$ is a bond,

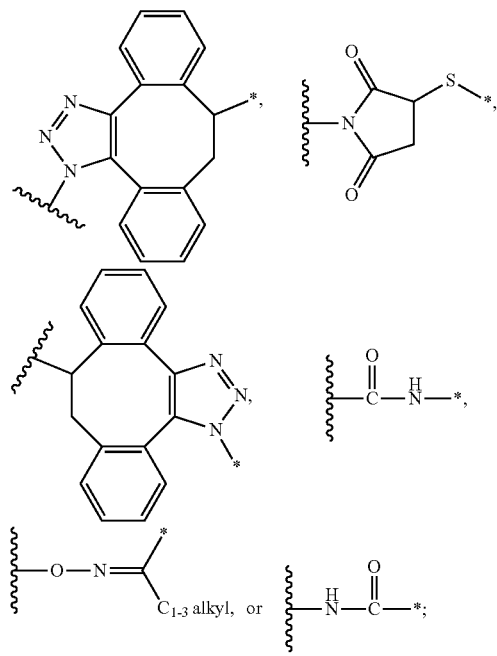

where the open valence of $R^{40}$ that is bonded to Ab is denoted by an asterisk (*) and the open valence of $R^{40}$ that is bonded to $(CH_2)_r$ is denoted by a wavy line ( ~~~ );

v is 0 or 1, with the provisos that v can be 0 only if s is 1 and $R^{40}$ is a bond and that $R^{40}$ can be a bond only if v is 0 and s is 1;

each G is C or N, with the proviso that no more than two Gs are N;

$R^2$ is H or $C_1$-$C_5$ alkyl;

$R^3$ and $R^4$ are independently H, F, Cl, Br, OH, $C_1$-$C_3$ alkyl, $O(C_1$-$C_3$ alkyl), cyano, $(CH_2)_{0-5}NH_2$, or $NO_2$;

the double line ----- in the diazepine ring system represents a single bond or a double bond;

$R^5$ is H if the double line ----- is a single bond and is absent if the double line ----- is a double bond;

$R^6$ is H, OH, $SO_3Na$, or $SO_3K$ if the double line ----- is a single bond and is absent if the double line ----- is a double bond;

$R^7$, $R^8$, $R^9$, and $R^{10}$ are independently H, $C_1$-$C_5$ alkyl, C≡C$(CH_2)_{1-5}X^2$, OH, $O(C_1$-$C_5$ alkyl), cyano, $NO_2$, F, Cl, Br, $O(CH_2CH_2O)_{1-8}(C_1$-$C_3$ alkyl), $(CH_2)_{0-5}X^2$, O$(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, phenyl unsubstituted or substituted with $(CH_2)_{0-5}X^2$ or $O(CH_2)_{2-5}X^2$, 5- to 6-membered heteroaryl unsubstituted or substituted with $(CH_2)_{0-5}X^2$ or $O(CH_2)_{2-5}X^2$,

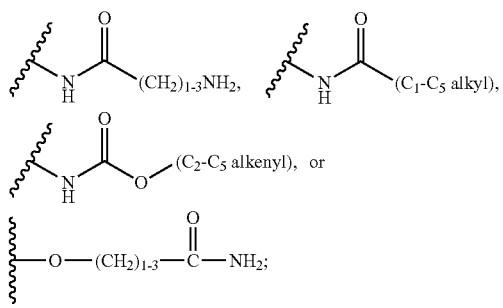

or where a $R^7$, $R^8$, $R^9$, or $R^{10}$ s attached to a G that is N, such $R^7$, $R^8$, $R^9$, or $R^{10}$ is absent;

each $X^2$ is independently H, F, Cl, Br, OH, $O(C_1$-$C_3$ alkyl), $O(C_1$-$C_3$ alkylene), $CO_2H$, $N_3$, CN, $NO_2$, $CO_2(C_1$-$C_3$ alkyl), $NH_2$, $NH(C_1$-$C_5$ alkyl), $N(C_1$-$C_5$ alkyl)$_2$, SH, CHO, $N(CH_2CH_2)_2N(C_1$-$C_3$ alkyl), $NHNH_2$, or C(=O)$NHNH_2$;

each Y is independently $CH_2$, C=O, or $CHR^{12}$; wherein each $R^{12}$ is independently F, Cl, Br, or $C_1$-$C_3$ alkyl;

n is 2, 3, 4, 5, or 6;

$X^{20}$ and $X^{21}$ are independently

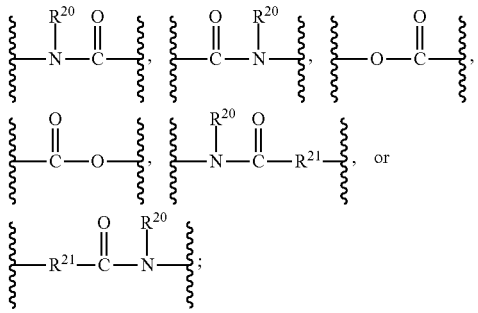

wherein $R^0$ is H or $C_1$-$C_3$ alkyl and $R^{21}$ is O, NH, or $N(C_1$-$C_3$ alkyl;

$Ar^1$ is (i) a phenyl moiety, (ii) a 5- or 6-membered heteroaromatic moiety, or (iii) a polycyclic aromatic moiety comprising a phenyl or 6-membered heteroaromatic ring fused to a phenyl ring or a 5- or 6-membered heteroaromatic ring; each phenyl, heteroaromatic, or polycyclic aromatic moiety being optionally substituted with one or more of $C_1$-$C_6$ alkyl, Cl, or F;

W is (a) $C_1$-$C_6$ alkyl or cycloalkyl or (b) an aromatic moiety comprising one to three (i) phenyl or (ii) 5- or 6-membered heteroaromatic rings, which phenyl or 5- or 6-membered heteroaromatic rings are optionally substituted with one or more of $C_1$-$C_3$ alkyl, OH, Cl, F, $CH_2F$, $CHF_2$, $CF_3$, $O(C_1$-$C_3$ alkyl), $O(CH_2)_{2-4}OH$, $O(CH_2)_{0-2}CHF_2$, C(=O)$(C_1$-$C_3$ alkyl), C(=O)$O(C_1$-$C_3$ alkyl), C(=O)$NH_2$, C(=O)$NH(C_1$-$C_3$ alkyl), C(=O)$N(C_1$-$C_3$ alkyl)$_2$, $O(C_2$-$C_4$ alkenyl), $NH_2$, $NH(C_1$-$C_3$ alkyl), $N(C_1$-$C_3$ alkyl)$_2$, O(CH$_2$)$_{0-2}$C$_6$H$_5$, CN, or NO$_2$; wherein, if more than one phenyl or 5- or 6-membered heteroaromatic ring is present, such rings are fused to each other or joined by an aryl-aryl bond;

each R$^{35}$ is independently H, Cl, F, Br, C$_1$-C$_5$ alkyl, O(C$_1$-C$_5$ alkyl), OH, CN, NO$_2$, NH(C=O)(C$_1$-C$_5$ alkyl), N(C$_1$-C$_5$ alkyl)$_2$, or CF$_3$;

X$^{22}$ is O or NH;

and

W' is an aromatic moiety comprising one to three (i) phenyl or (ii) 5- or 6-membered heteroaromatic rings, which phenyl or 5- or 6-membered heteroaromatic rings are optionally substituted with one or more of C$_1$-C$_3$ alkyl, OH, Cl, F, CH$_2$F, CHF$_2$, CF$_3$, O(C$_1$-C$_3$ alkyl), O(CH$_2$)$_{2-4}$OH, O(CH$_2$)$_{0-2}$CHF$_2$, C(=O)(C$_1$-C$_3$ alkyl), C(=O)O (C$_1$-C$_3$ alkyl), C(=O)NH$_2$, C(=O)NH(C$_1$-C$_3$ alkyl), C(=O)N(C$_1$-C$_3$ alkyl)$_2$, O(C$_2$-C$_4$ alkenyl), NH$_2$, NH(C$_1$-C$_3$ alkyl), N(C$_1$-C$_3$ alkyl)$_2$, O(CH$_2$)$_{0-2}$C$_6$H$_5$, CN, or NO$_2$; wherein, if more than one phenyl or 5- or 6-membered heteroaromatic ring is present, such rings are fused to each other or joined by an aryl-aryl bond.

Formulae (IVa), (IVb), and (IVc) correspond to conjugates derived from type (a), type (b) and type (c) drug-linker compounds, respectively.

EXAMPLES

The practice of this invention can be further understood by reference to the following examples, which are provided by way of illustration and not of limitation.

Abbreviations and Acronyms

The following abbreviations and acronyms are used in this application.
Alloc: allyloxycarbonyl
Boc: t-butoxycarbonyl
DCM: dichloromethane
DIAD: diisopropyl azodicarboxylate
DIPEA: N-ethyl-N-isopropylpropan-2-amine
DMSO: dimethylsulfoxide
DMF: N,N-dimethylformamide
DTDP: dithiodipyridine
DTPA: diethylene triamine pentaacetic acid
Fmoc: 9-fluorenylmethoxycarbonyl
HATU: 2-(3H-[1,2,3]triazolo[4,5-b]pyridin-3-yl)-1,1,3,3-tetramethylisouronium hexafluorophosphate(V)
MsOH: methanesulfonic acid
NMP: N-methylpyrrolidone
RT: room (ambient) temperature, circa 25° C.
TBAF: tetrabutylammonium fluoride
TFA: trifluoroacetic acid
THF: tetrahydrofuran
TBS: t-butyldimethylsilyl
TsO: p-toluenesulfonate
SPhos: 2-dicyclohexylphosphino-2',6'-dimethoxybiphenyl Example 1—Conjugation by Michael Addition This general procedure is based on introduction of free thiol groups into an antibody by reaction of lysine ε-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM DTPA and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at room temperature ("RT," circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with DTDP. Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 M$^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols. The sample is then filtered via a 0.2μ filter The material is buffer exchanged via TFF Viva-Flow 50 Sartorius 30 MWCO PES membrane into 10 mg/mL glycine, 20 mg/mL sorbitol, 15% acetonitrile, pH 5.0 (5×TFF buffer exchange volume), to remove any unreacted drug. The final formulation is carried out by TFF into 20 mg/mL sorbitol, 10 mg/mL glycine, pH 5.0.

Example 2—Transglutaminase-Mediated Conjugation

The following procedure can be used for transglutaminase mediated conjugation of drug-linker compounds wherein the linker has an amine group that can act as an amine donor. The antibody can be one that has a transglutaminase-reactive glutamine, for example one with an N297A or N297Q substitution. Conjugation is carried out by recombinant bacterial transglutaminase with a molar ratio of antibody: enzyme of 5:1. The conjugation is carried out using standard protocols in 50 mM Tris buffer, pH 8.0, incubated overnight at 37° C. The resulting conjugate is purified on a Protein A column, pre-equilibrated with 50 mM Tris, pH 8.0. The conjugate is eluted with 0.1 M sodium citrate buffer, pH 3.5.

The eluted fractions are neutralized with 1M Tris pH 9.0. The conjugated can be formulated in 20 mg/mL Sorbitol, 10 mg/mL Glycine, pH 5.0.

Those skilled in the art will understand that the conditions and methodologies in these two examples are illustrative and non-limiting and that variations thereof or other approaches for conjugation are known in the art and usable in the present invention.

Example 3—Biological Activity of Compounds

Table II shows the cell proliferation inhibition efficacy of compounds disclosed herein against various human cancer cell lines: gastric (stomach) cancer (N87), ovarian cancer (OVCAR3), mesothelioma (H226), and colon cancer (HCT116).

Proliferation inhibition was measured using a 72 hr ATP luminescence assay (Cheng et al., U.S. Pat. No. 8,394,922 B2 (2013)). The antiproliferative effects are reported as $IC_{50}$'s, i.e., the concentration of compound that produces a 50% inhibitory effect on cell proliferation.

TABLE II

| | Cell Line and $IC_{50}$ (nM) | | | |
|---|---|---|---|---|
| Compound | H226 | N87 | HCT116 | OVCAR3 |
| (Ib-01) | 1.2 | 0.65 | 0.73 | 0.38 |
| (Ib-02) | <250 | 93 | <250 | 140 |
| (Ib-03) | 9.4 | 2.4 | 6.9 | 3.1 |
| (Ib-04) | 5.6 | 2.6 | 2.7 | 0.78 |
| (Ib-05) | 0.23 | 0.11 | 0.12 | 0.27 |
| (Ib-06) | <0.004 | 0.009 | 0.008 | 0.031 |
| (Ib-07) | 0.02 | 0.073 | 0.018 | 0.024 |
| (Ib-08) | 0.007 | 0.006 | <0.004 | 0.013 |
| (Ib-09) | 0.05 | 0.035 | 0.039 | 0.12 |
| (Ib-10) | 0.018 | 0.026 | 0.014 | 0.037 |
| (Ib-11) | 0.98 | 0.12 | 0.026 | 0.10 |
| (Ib-12) | 0.059 | 0.027 | 0.023 | 0.074 |
| (Ib-13) | 0.039 | 0.14 | 0.036 | 0.17 |
| (Ib-14) | 0.67 | 0.049 | 0.070 | 0.18 |
| (Ib-15) | <0.004 | <0.004 | 0.002 | <0.004 |
| (Ib-16) | <0.004 | <0.004 | <0.004 | 0.12 |
| (Ib-17) | <0.004 | 0.009 | 0.011 | 0.028 |
| (Ib-18) | 0.11 | 0.052 | 0.055 | 0.20 |
| (Ib-19) | 0.11 | 0.045 | 0.038 | 0.23 |
| (Ib-20) | 0.031 | 0.014 | 0.027 | 0.10 |
| (Ib-21) | 0.19 | 0.091 | 0.057 | 0.35 |
| (Ib-22) | 0.18 | 0.24 | 0.088 | 0.91 |
| (Ib-23) | 0.036 | 0.014 | 0.007 | 0.022 |
| (Ib-24) | 0.053 | 0.074 | 0.008 | 0.16 |
| (Ib-25) | 0.15 | 0.084 | 0.057 | 0.35 |
| (Ib-26) | <0.004 | <0.004 | 0.025 | 0.44 |
| (Ib-27) | 0.067 | 0.021 | 0.020 | 0.15 |
| (Ib-28) | 0.72 | 0.18 | 0.18 | 0.40 |
| (Ib-29) | 0.10 | 0.042 | 0.041 | 0.16 |
| (Ib-30) | 0.66 | 0.37 | 0.10 | 0.76 |
| (Ib-31) | 0.28 | 0.23 | 0.078 | 0.94 |
| (Ib-32) | 3.1 | 0.41 | 0.30 | 1.6 |
| (Ib-33) | <0.004 | <0.004 | <0.004 | 0.052 |
| (Ib-34) | <0.004 | 0.006 | <0.004 | 0.025 |
| (Ib-35) | <0.004 | <0.004 | 0.047 | 0.11 |
| (Ib-36) | 22 | 3.7 | 3.7 | 2.2 |
| (Ib-37) | 1.2 | 1.6 | 1.7 | 5.2 |
| (Ib-38) | 1.1 | 1.1 | 1.1 | 0.66 |
| (Ib-39) | 0.006 | 0.002 | 0.003 | 0.011 |
| (Ib-40) | 0.10 | 0.090 | 0.028 | 0.16 |
| (Ib-41) | 0.083 | 0.038 | 0.022 | 0.053 |
| (Ib-42) | 0.49 | 0.39 | 0.38 | 0.32 |
| (Ib-43) | 0.013 | 0.026 | 0.008 | 0.025 |
| (Ib-44) | 0.085 | 0.055 | 0.045 | 0.053 |
| (Ib-45) | 0.085 | 0.025 | 0.032 | 0.010 |
| (Ib-46) | 0.27 | 0.12 | 0.13 | 0.55 |
| (Ib-47) | 0.13 | 0.022 | 0.019 | 0.13 |
| (Ib-48) | 0.18 | 0.075 | 0.039 | 0.094 |

TABLE II-continued

| | Cell Line and $IC_{50}$ (nM) | | | |
|---|---|---|---|---|
| Compound | H226 | N87 | HCT116 | OVCAR3 |
| (Ib-49) | 0.062 | 0.16 | 0.051 | 0.32 |
| (Ib-50) | 0.12 | 0.21 | 0.052 | 0.22 |
| (Ib-51) | 0.11 | 0.037 | 0.022 | 0.70 |
| (Ib-52) | 0.30 | 0.45 | 0.28 | 0.63 |
| (Ib-53) | 0.13 | 0.092 | 0.098 | 0.22 |
| (Ib-54) | 0.050 | 0.027 | 0.007 | 0.071 |
| (Ib-55) | 0.018 | <0.004 | 0.004 | 0.045 |

The above results demonstrate the versatility of the heterodimers disclosed herein. The part of the dimer represented by

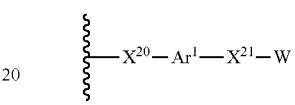

is readily amenable to substantial structural variability, allowing one to adjust the cytotoxic potency of the dimers, with $IC_{50}$ values from the picomolar to the micromolar range, depending on the desired potency for the intended end use.

Example 4—Intermediates 4 and 4a

This example and FIG. 1 relate to the synthesis of intermediates 4 and 4a, usable for the preparation of compounds disclosed herein.

A suspension of phenol 1 (1500 mg, 2.86 mmol, Zhang et al. 2016), methyl 4-bromobutanoate 2 (1000 mg, 5.52 mmol) and $Cs_2CO_3$ (2000 mg, 6.14 mmol) in DMF (5 mL) was stirred at RT for 1 h. The mixture was quenched with 0.1 M citric acid and extracted thrice with EtOAc. The combined organics were washed with brine, dried over $Na_2SO_4$, filtered and evaporated. The mixture was purified by silica gel chromatography, eluting with a gradient from 30-80% EtOAc in hexanes to afford ester 3 (1710 mg, 2.74 mmol, 96% yield). LCMS M+H=625.25.

Ester 3 (1710 mg, 2.74 mmol) was dissolved in MeOH (40 mL). Water (10 mL) was added. To this solution was added LiOH hydrate (655 mg, 27.4 mmol). After stirring for 1 h, the mixture was quenched with 0.1 M citric acid and extracted thrice with EtOAc. The combined organics were washed with brine and dried over $Na_2SO_4$, filtered and evaporated to afford acid 4, used without further purification (1.54 g, 5.52 mmol, 92% yield). LCMS M+H=611.20.

DIAD (1.126 mL, 5.72 mmol) was added to a mixture of compound 2a (0.782 g, 3.81 mmol), compound 1 (1 g, 1.906 mmol) and triphenylphosphine (1.500 g, 5.72 mmol) in THF (7 mL) at 0° C. The reaction mixture was allowed to warm up to RT and was stirred at RT for 1 h. Water was added to quench the reaction. The aqueous solution was extracted with EtOAc and the combined organic layers were washed with brine, dried, filtered, and concentrated. The crude product was purified by flash chromatography eluting from silica gel with a gradient of 0-100% EtOAc in hexanes to afford 0.81 g of compound 3a as a white froth. MS: (+) m/z 712.2 (M+1).

Methylamine in water (40 wt %, 3.25 mL, 37.5 mmol) was added to a mixture of compound 3a (0.81 g, 1.138 mmol) in MeOH (6 mL) at RT. The reaction mixture was stirred at RT for 4 h. The solvent was evaporated. The crude product was purified by flash chromatography eluting from silica gel with a gradient of 0-100% MeOH in DCM to afford 0.11 g of compound 4a as a white solid. MS: (+) m/z 582.2 (M+1).

Compounds 4 and 4a are versatile starting points for the synthesis of diverse heterodimers. They provide a THIQ moiety and a polymethylene tether for connecting the two dimer halves. By attaching these compounds to a moiety

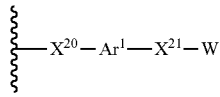

many different dimers can be made.

The length of the polymethylene tether can be varied by using homologs of compounds 2 and 2a, to make homologs of compounds 4 and 4a having varying tether lengths, of the formula (V) or (Va):

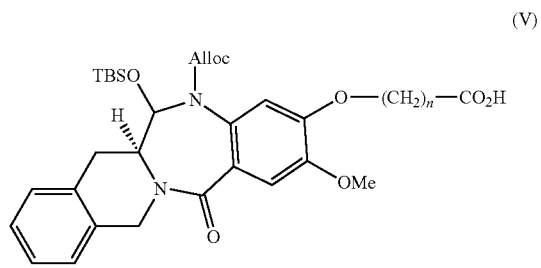

(V)

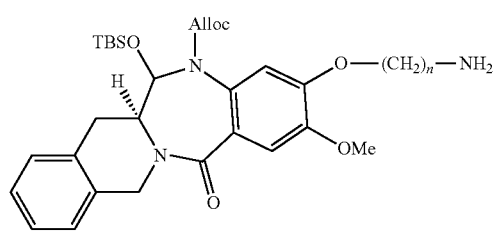

(Va)

where n is 2, 3, 4, 5, or 6

Example 5—Compound (Ib-13)

Figure 2:
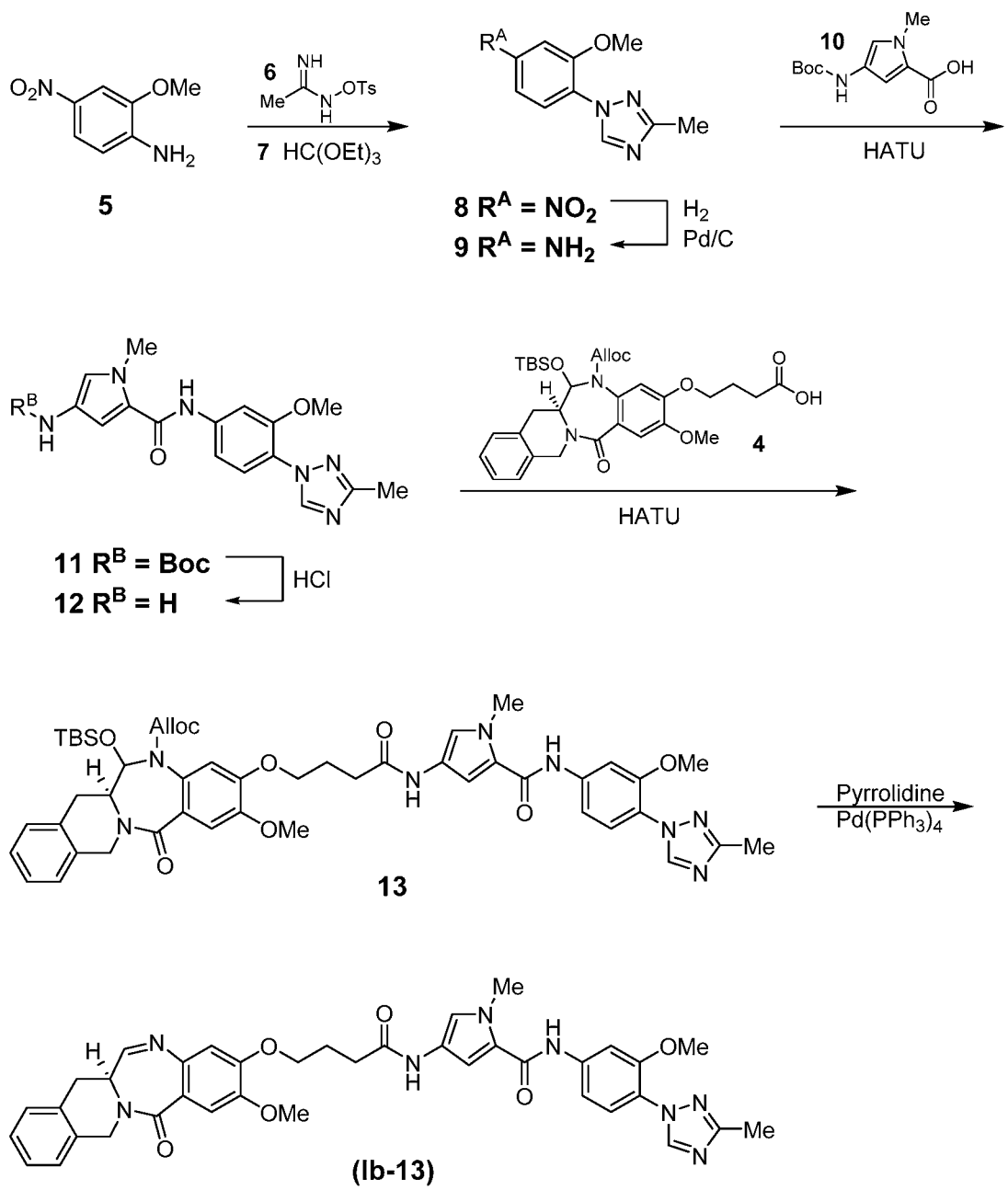
FIG. 2 shows a reaction scheme for the synthesis of a compound disclosed herein.

This example and FIG. 2 relate to the synthesis of compound (Ib-13). The procedure used can be adapted for the preparation of other dimers disclosed herein, as detailed hereinbelow.

N-(tosyloxy)acetimidamide 6 (4.89 g, 21.41 mmol, EP 0795551 A1) and triethoxymethane 7 (4.45 ml, 26.8 mmol) were added to a solution of 2-methoxy-4-nitroaniline 5 (3 g, 17.84 mmol) in THF (30 mL). The mixture was heated at 60° C. overnight, cooled to RT and concentrated. The residue was taken up in DCM washed with 40 mL of a 2:1 mixture of saturated $NaHCO_3$:1 N NaOH and extracted a second time with DCM. The combined organics were washed with brine, dried over $MgSO_4$, filtered and concentrated. The residue was taken up in 50 mL of hot EtOAc and 25 mL of hexane was added. The mixture was heated to boiling, cooled and filtered to give triazole 8 as a red brown solid (2.6 g, 62%). LCMS M+H=235.1.

A dried 25 mL two-necked round-bottom flask equipped with a magnetic stirring bar, an adaptor with an $N_2$ inlet, and a cooled condenser was charged with triazole 8 (0.5 g, 2.135 mmol) in MeOH (20 mL). To this was added Pd/C (0.045 g, 0.427 mmol). The reaction mixture was fitted with a hydrogen balloon and stirred for 4 h. The reaction mixture was filtered through a CELITE™ bed and concentrated under reduced pressure. The residue was dissolved in DCM (10 mL) and silica gel (5 g) was added. The resultant slurry of the compound on silica gel was subjected to flash chromatography using a Teledyne Isco instrument (40 g RediSep silica column, 50% EtOAc in petroleum ether) to afford aniline 9 as a light green solid (0.4 g, 92%). LCMS M+H=205.2.

A mixture of acid 10 (0.5 g, 2.081 mmol) and HATU (0.870 g, 2.289 mmol) in DMF (2.5 mL) was stirred for 10 min at RT. DIPEA (1.090 mL, 6.24 mmol) was added followed by aniline 9 (0.425 g, 2.081 mmol). The reaction mixture was stirred at RT for 3 h, heated at 97° C. for 12 h, diluted with DCM, and purified on silica gel (120 g Isco column) using 0-10% MeOH in EtOAc. The desired fractions were concentrated to give compound 11 as a beige solid (0.69 g, 78%). LCMS M+H=427.05.

Hydrochloric acid (4.04 mL, 16.18 mmol, 4 N in dioxane) was added to a solution of compound 11 (0.69 g, 1.618 mmol) in DCM (4 mL). The reaction mixture was stirred at RT for 24 h. The reaction mixture (suspension) was diluted with ether, filtered, suction dried and dried under vacuum to give amine 12 as a beige solid (0.53 g, 90%). LCMS M+H=327.0.

HATU (0.037 g, 0.098 mmol) was added to a solution of intermediate 4 (0.05 g, 0.082 mmol) in DMF (0.5 mL). The mixture was stirred for 10 min, DIPEA (0.057 mL, 0.327 mmol) was added, followed by amine 12 (0.030 g, 0.082 mmol). Stirring was continued at RT for 16 h. The reaction mixture was diluted with DCM (1 mL) and purified on silica gel (24 g Isco column) using 25-100% EtOAc in hexanes. The desired fractions were concentrated to give protected dimer 13 as an off-white solid (0.056 g, 74%). LCMS M+H=919.30.

Pyrrolidine (0.042M in DCM, 3.63 mL, 0.152 mmol) was added to protected dimer 13 (0.056 g, 0.061 mmol), followed by tetrakis(triphenylphosphine)palladium(O) (6.27 mg, 5.42 μmol). The mixture was stirred for 1 h and concentrated under a stream of nitrogen. The residue was purified on a C18 Biotage column (55 g) using a gradient of 20-100% of eluent B (95% acetonitrile/5% water/0.05% formic acid) in eluent A (5% acetonitrile/95% water/0.05% formic acid) over 20 column volumes. The desired fractions were lyophilized to give compound (Ib-13) as an off-white solid (15 mg, 33%). LCMS M+H=703.40.

Example 6—Additional Compounds Per FIG. 2

Additional compounds according to Table I were prepared, analogously following the procedures of Example 5 and FIG. 2, but using other amines in lieu of amine 9. Such other amines and the compounds so made are listed in Table III below.

TABLE III

| Compound | Amine Used in Lieu of Amine 9 | | Compound LCMS [M + H] |
|---|---|---|---|
| | Structure | Source, Reference or Example | |
| (Ib-06) | 5-amino-2-(3-methyl-1H-1,2,4-triazol-1-yl)pyridine | Gijsen et al., WO 2010/094647 | 674.4 |
| (Ib-07) | 5-amino-2-(4-chloro-1H-imidazol-1-yl)pyridine | Saito et al., WO 2015/115673 | 693.3 |
| (Ib-08) | 4-amino-2-fluoro-1-(3-methyl-1H-1,2,4-triazol-1-yl)benzene | Boy et al., US 2012/0028994 | 673.4 |
| (Ib-09) | 4-amino-2-(difluoromethyl)-1-(3-methyl-1H-1,2,4-triazol-1-yl)benzene | Example 11 | 723.2 |
| (Ib-10) | 4-amino-2-methoxy-1-(3-(difluoromethyl)-1H-1,2,4-triazol-1-yl)benzene | Boy et al., US 2012/0028994 | 739.4 |
| (Ib-11) | 4-amino-2-(2,2-difluoroethoxy)-1-(3-methyl-1H-1,2,4-triazol-1-yl)benzene | Example 17 | 753.4 |
| (Ib-12) | 4-amino-2-(difluoromethoxy)-1-(3-methyl-1H-1,2,4-triazol-1-yl)benzene | Boy et al., WO 2015/153709 | 739.4 |
| (Ib-14) | isopropyl 4'-amino-[1,1'-biphenyl]-3-carboxylate | Marcin et al., WO 2010/083141 | 754.4 |

TABLE III-continued

| Compound | Amine Used in Lieu of Amine 9 Structure | Source, Reference or Example | Compound LCMS [M + H] |
|---|---|---|---|
| (Ib-15) | H₂N–C₆H₄–C₆H₄–OMe | Marcin et al., WO 2010/083141 | 698.5 |
| (Ib-16) | H₂N–C₆H₄–(1,2,4-triazol-1-yl)–Me | Kamenecka et al., WO2009/032861 | 673.4 |
| (Ib-17) | H₂N–C₆H₄–(1,2,4-triazol-1-yl) | Warfield et al., WO 2016/073652 | 659.4 |
| (Ib-18) | H₂N–C₆H₃(OMe)–(imidazol-1-yl)–CHF₂ | Boy et al., US 2012/0028994 | 738.4 |
| (Ib-19) | H₂N–C₆H₃(OMe)–(imidazol-1-yl)–Cl | Boy et al., US 2012/0028994 | 722.4 |
| (Ib-20) | H₂N–C₆H₃(F)–(imidazol-1-yl)–Cl | Example 12 | 710.35 |
| (Ib-21) | H₂N–C₆H₃(OMe)–(imidazol-1-yl)–Me | Boy et al., US 2012/0028994 | 702.4 |
| (Ib-22) | H₂N–C₆H₄–(imidazol-1-yl) | Alfa | 658.4 |

TABLE III-continued

| Compound | Structure | Source, Reference or Example | Compound LCMS [M + H] |
|---|---|---|---|
| (Ib-23) | H₂N—C₆H₄—oxazole | Synquest | 659.4 |
| (Ib-24) | H₂N—(4-pyrazolyl) with N-phenyl | ZelinskyBB | 658.4 |
| (Ib-25) | H₂N—C₆H₄—(1-Me-imidazole-2-CO₂Me) | CAS Reg. No. 864076-06-2 | 730.4 |
| (Ib-26) | H₂N—C₆H₃(O-allyl)—(3-Me-1,2,4-triazol-1-yl); From same reaction for preparation of compound (Ib-27); loss of Alloc group leads to compound (Ib-26) | Boy et al., WO 2012/009309 | 689.4 |
| (Ib-27) | H₂N—C₆H₃(O-allyl)—(3-Me-1,2,4-triazol-1-yl) | Boy et al., WO 2012/009309 | 729.5 |
| (Ib-28) | H₂N—C₆H₂(Me)₂—(1,2,4-triazol-1-yl) | Example 13 | 687.40 |
| (Ib-29) | H₂N—C₆H₃(OMe)—(1,2,4-triazol-1-yl) | CAS Reg. No. 267648-18-0 | 689.40 |
| (Ib-30) | H₂N—C₆H₄—(2-imidazolyl) | GreenChem | 658.4 |

TABLE III-continued

| Compound | Amine Used in Lieu of Amine 9 Structure | Source, Reference or Example | Compound LCMS [M + H] |
|---|---|---|---|
| (Ib-31) | | Raddatz et al., WO 99/40094 (1999) | 687.4 |
| (Ib-32) | | Example 18 | 687.4 |
| (Ib-33) | | Sigma | 682.4 |
| (Ib-34) | (Alloc group removed during synthesis) | Combi-Blocks | 695.4 |
| (Ib-35) | | JW-Pharmalab | 623.4 |
| (Ib-36) | | Combi-Blocks | 699.4 |
| (Ib-37) | | Combi-Blocks | 647.4 |
| (Ib-39) | | Rahman et al., J. Med. Chem. 2013, 56, 2911 | 729.35 |
| (Ib-40) | | Oakwood | 653.35 |

TABLE III-continued

| Compound | Amine Used in Lieu of Amine 9 Structure | Source, Reference or Example | Compound LCMS [M + H] |
| --- | --- | --- | --- |
| (Ib-41) | aniline | Aldrich | 592.35 |
| (Ib-42) | cyclopropylamine | Aldrich | 556.30 |
| (Ib-43) | 4-aminobiphenyl | Aldrich | 668.30 |
| (Ib-44) | 2-aminopyridine | Aldrich | 593.30 |
| (Ib-45) | 6-amino-3-chloropyridine | Aldrich | 627.30 |
| (Ib-46) | 3-aminopyridine | Aldrich | 593.30 |
| (Ib-47) | 5-amino-2-chloropyridine | Aldrich | 627.25 |
| (Ib-50) | 4-(5-(methylcarbamoyl)-1-methyl-1H-pyrrol-3-yl)aniline | Example 14 | 738.40 |
| (Ib-51) | 4-(benzyloxy)aniline | Oakwood | 698.40 |
| (Ib-53) | 3,3'-dimethoxy-4'-(Alloc-amino)-4-aminobiphenyl | Example 15 | 743.05 |

Alloc group removed during course of synthesis

TABLE III-continued

| Compound | Amine Used in Lieu of Amine 9 | | Compound |
| | Structure | Source, Reference or Example | LCMS [M + H] |
| --- | --- | --- | --- |
| (Ib-54) | H₂N—⟨phenyl⟩—⟨phenyl⟩—NHAlloc  Alloc group removed during course of synthesis | Example 16 | 683.40 |

Further compounds from Table I were prepared, analogously following the procedures of Example 5 and FIG. 2, but using other amines in lieu of compound 12. Such other amines and the compounds so made are tabulated in Table IV below.

TABLE IV

| Compound | Other Amine Used in Lieu of Compound 12 | | Compound |
| | Structure | Source, Reference, or Example | LCMS [M + H] |
| --- | --- | --- | --- |
| (Ib-01) | H₂N—⟨C₆H₄⟩—C(O)NH—⟨Ph⟩ | Aldrich | 589.4 |
| (Ib-02) | 2-H₂N—⟨C₆H₄⟩—C(O)NH—⟨Ph⟩ | CAS Reg. No. 4424-17-3 | 589.35 |
| (Ib-03) | 3-H₂N—⟨C₆H₄⟩—C(O)NH—⟨Ph⟩ | CAS Reg. No. 14315-16-3 | 589.3 |
| (Ib-04) | 2-amino-thiazole-5-C(O)NH—Ph | CAS Reg. No. 1184919-01-4 | 596.3 |
| (Ib-05) | 2-amino-thiazole-4-C(O)NH—Ph | CAS Reg. No. 1340272-93-6 | 596.3 |

TABLE IV-continued

| Compound | Structure | Source, Reference, or Example | LCMS [M + H] |
|---|---|---|---|
| (Ib-38) | (4-amino-1-methyl-pyrrole-2-carboxylic acid methyl ester) | Astatech | 531.30 |
| (Ib-48) | (4-amino-1-methyl-N-phenyl-imidazole-2-carboxamide) | Example 19 | 593.35 |
| (Ib-49) | (4-amino-1-methyl-N-[4-(1-methyl-5-(oxazol-2-yl)-pyrrol-3-yl)phenyl]pyrrole-2-carboxamide) | Example 21 | 738.40 |
| (Ib-52) | (4-amino-1-methyl-N-[4-(Alloc-amino)phenyl]pyrrole-2-carboxamide) Alloc group removed during course of synthesis | Example 20 | 607.35 |
| (Ib-55) | (4-amino-1-methyl-N-[4-(1-methyl-5-methoxycarbonyl-pyrrol-3-yl)phenyl]imidazole-2-carboxamide) | CAS Reg. No. 1821339-84-7 | 730.40 |

Example 7—Drug-Linker Compounds (IIIa-01) and (IIIa-02)

Figure 3A:
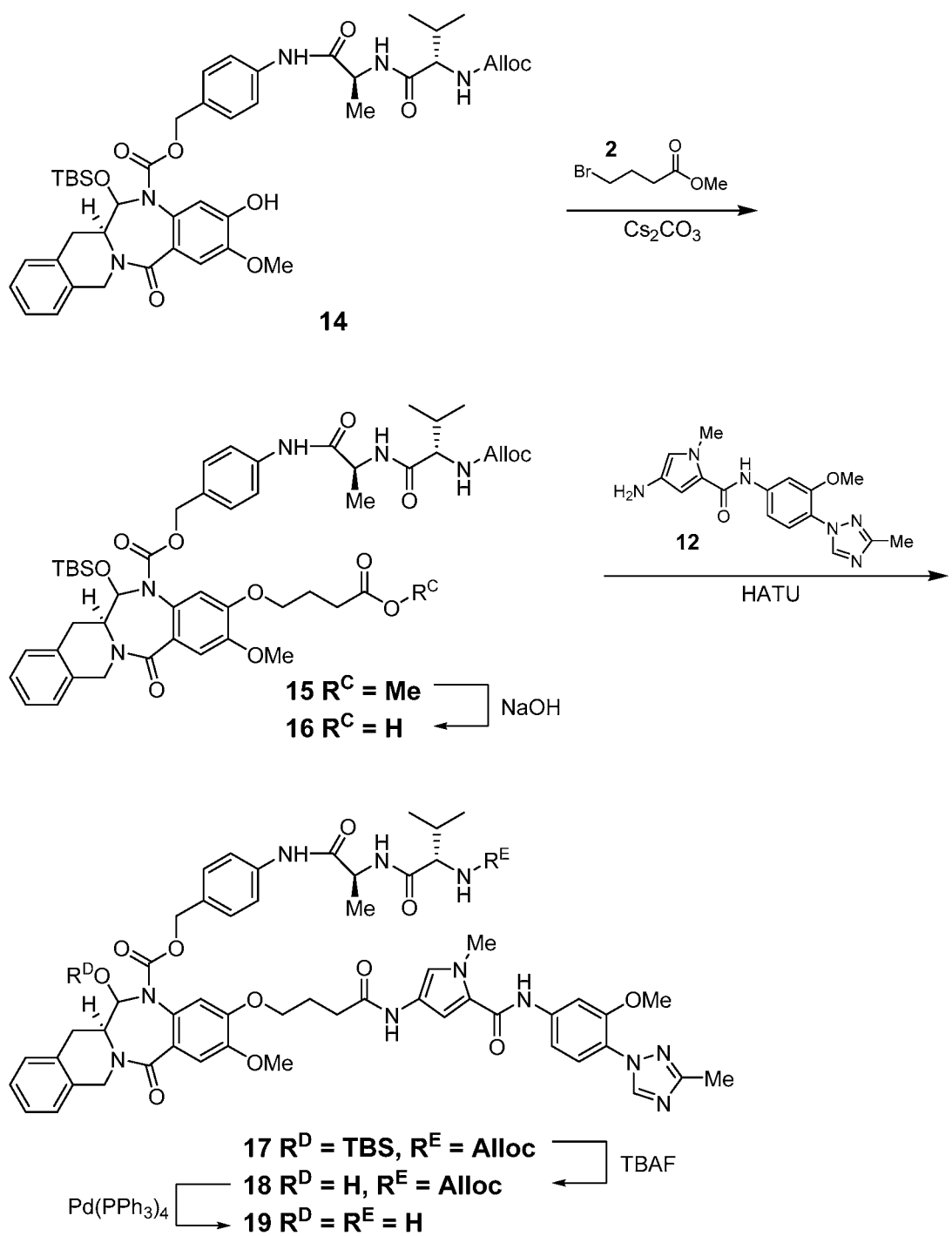
FIGS. 3A and 3B show, in combination, a reaction scheme for the synthesis of a drug-linker compound disclosed herein.
Figure 3B:
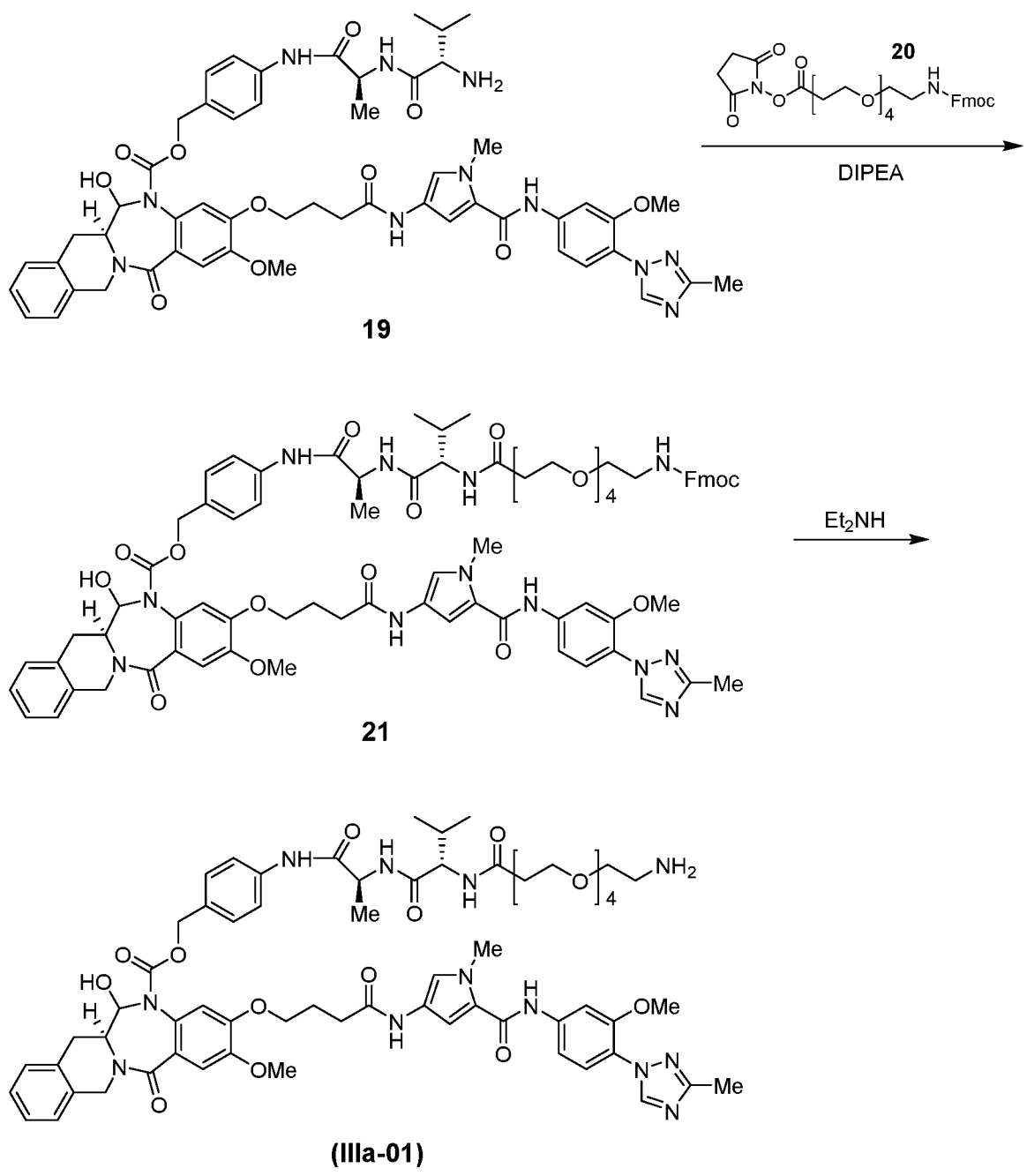

This example and FIGS. 3A-3B relate to the synthesis of drug-linker compounds (IIIa-01) and (IIIa-02).

To a solution of phenol 14 (0.53 g, 0.628 mmol, Zhang et al. 2016)) in DMF (6.28 mL) was added methyl 4-bromobutanoate 2 (0.167 mL, 1.256 mmol) and $Cs_2CO_3$ (0.45 g, 1.381 mmol). This mixture was stirred for 18 h, diluted with EtOAc and washed successively with saturated $NaHCO_3$ and brine. The organic phase was dried over $Na_2SO_4$, filtered and evaporated. The mixture was purified on silica gel using 30-100% EtOAc in hexanes. The desired fractions were concentrated to give ester 15 as a white solid (0.48 g, 81%). LCMS M+H=944.30.

Ester 15 (0.46 g, 0.487 mmol) was dissolved in THF (19.49 mL) and a 1M solution of NaOH (4.87 mL, 4.87 mmol) was added. The solution was aged with stirring for 7 h, and then quenched by addition into 5% citric acid. The mixture was extracted thrice with DCM and dried over $Na_2SO_4$. Filtration and evaporation of the solvent afforded acid 16 as a tan solid (0.46 g, 71%, ~70% purity), used as-is in subsequent reactions. LCMS M+H=930.35.

HATU (0.032 g, 0.084 mmol) was added to a solution of acid 16 (0.065 g, 0.070 mmol) in DMF (1 mL). The mixture was stirred for 10 min, DIPEA (0.049 mL, 0.280 mmol) was added, followed by the addition of compound 12 (0.028 g, 0.077 mmol). Stirring was continued at RT for 16 h. The reaction mixture was diluted with DCM (1 mL) and purified on silica gel (24 g Isco column) using a 25-100% gradient of EtOAc in hexanes, then a 5-10% gradient of MeOH in EtOAc The desired fractions were concentrated to give compound 17 as a beige solid (0.074 g, 85%). LCMS M+H=1238.4.

TBAF (0.119 mL, 0.119 mmol) was added to compound 17 (0.0736 g, 0.059 mmol) in THF. The mixture was stirred for 30 min; diluted with EtOAc (40 mL); washed with water, saturated NaHCO$_3$, and brine; dried over Na$_2$SO$_4$, and concentrated and purified on silica gel (40 g Isco column) using 1-10% methanol in EtOAc. The desired fractions were concentrated to give compound 18 as a pale yellow solid (0.0935 g, 88%). LCMS LCMS M+H=1124.4.

Pyrrolidine (4.95 mL, 0.208 mmol, 0.042 M in DCM) was added to compound 18 (0.0935 g, 0.083 mmol), followed by tetrakis(triphenylphosphine)palladium(O) (8.55 mg, 7.40 µmol). The mixture was stirred for 30 min, diluted with DCM, washed with saturated NH$_4$Cl and brine. The organic layer was dried over Na$_2$SO$_4$ and concentrated to give compound 19 as a yellow solid (0.087 g, 101%, used as is). LCMS M+H=1040.6.

DIPEA (2.012 mL, 0.101 mmol, 0.05M in DMF) was added to a mixture of compounds 20 (0.073 g, 0.125 mmol) and 19 (0.087 g, 0.084 mmol). The mixture was stirred at RT overnight and purified on a C18 Biotage column (55 g) using a 15-100% gradient of eluent B (95% acetonitrile/5% water/0.05% formic acid) in eluent A (5% acetonitrile/95% water/0.05% formic acid) over 20 column volumes. The desired fractions were concentrated to give compound 21 as a yellow oily film (0.031 g, 25%). LCMS M+H=1509.9.

Diethylamine (0.021 mL, 0.205 mmol) was added to a solution of compound 21 (0.031 g, 0.021 mmol) in DMF (2 mL). The mixture was stirred for 30 min and concentrated to remove the diethylamine. The residue was purified on a C18 Biotage column (55 g) using a 15-100% gradient of eluent B (95% acetonitrile/5% water/0.05% formic acid) in eluent A (5% acetonitrile/95% water/0.05% formic acid) over 20 column volumes. The desired fractions were lyophilized to give drug-linker (IIIa-01) as an off-white solid (0.020 g, 78%). LCMS (M+2H)/2=644.9.

Drug-linker (IIIa-02) was analogously made by replacing compound 20 with the corresponding compound having two polyethylene glycol (PEG) units instead of four: MS (m+1) =1200.5. $^1$H NMR (400 MHz, DMSO-d6): δ 10.05-9.76 (m, 3H), 8.69 (s, 1H), 8.19 (d, J=6.8 Hz, 1H), 7.88 (d, J=8.4 Hz, 1H), 7.75 (d, J=2.0 Hz, 1H), 7.61-7.41 (m, 4H), 7.38-7.19 (m, 5H), 7.19-6.98 (m, 4H), 6.70 (s, 1H), 5.15 (d, J=9.7 Hz, 1H), 5.05 (d, J=12.4 Hz, 1H), 4.77 (d, J=12.2 Hz, 1H), 4.68 (d, J=15.4 Hz, 1H), 4.40 (t, J=10.3 Hz, 2H), 4.20 (t, J=7.5 Hz, 1H), 3.99 (d, J=22.9 Hz, 1H), 3.87-3.74 (m, 8H), 3.58 (q, J=6.5 Hz, 2H), 3.46 (s, 5H), 3.32 (t, J=5.7 Hz, 2H), 3.03 (qd, J=15.2, 4.7 Hz, 4H), 2.62 (t, J=5.7 Hz, 2H), 2.49-2.34 (m, 4H), 2.15-1.84 (m, 3H), 1.29 (d, J=7.1 Hz, 3H), 0.84 (dd, J=15.6, 6.7 Hz, 6H).

Example 8—Compound (Ib-56)

Figure 4:
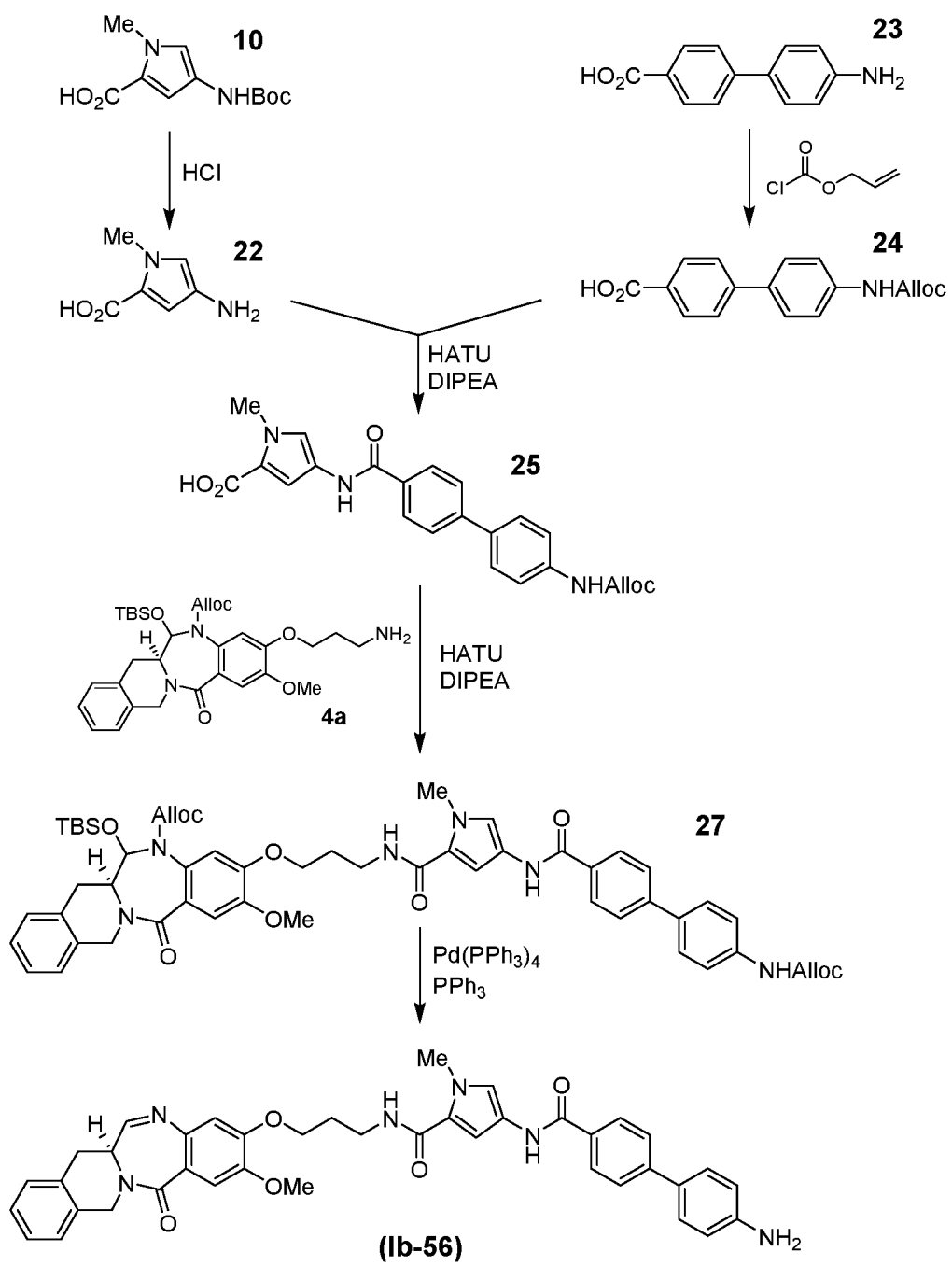
FIG. 4 shows a reaction scheme for the synthesis of another compound disclosed herein.

This example and FIG. 4 relate to the synthesis of compound (Ib-56).

Hydrochloric acid (4 N in dioxane, 4 mL, 16.00 mmol) was added to compound 10 (0.5 g, 2.081 mmol) at 0° C. The reaction mixture was stirred at RT for 1 h. The solvent was evaporated to afford 0.292 g of compound 22 as a white solid. MS: (+) m/z 141.0 (M+1).

Allyl chloroformate (0.199 mL, 1.876 mmol) was added to a mixture of 4'-amino-[1,1'-biphenyl]-4-carboxylic acid 23 (HCl salt, 0.2 g, 0.938 mmol) in 10% Na$_2$CO$_3$ solution (10 mL, 0.938 mmol) and THF (3 mL) at RT. The reaction mixture was stirred at RT for 4 h. The reaction mixture was washed with Et$_2$O, acidified with 1N HCl, and extracted with EtOAc. The combined organic layers were dried, filtered, and concentrated. The crude product was purified by flash chromatography eluting from silica gel with a gradient of 0-50% MeOH in DCM to afford 72.4 mg of compound 24 as a white solid. MS: (+) m/z 298.0 (M+1).

DIPEA (0.047 mL, 0.268 mmol) was added to a mixture of compound 24 (72.4 mg, 0.244 mmol) and HATU (102 mg, 0.268 mmol) in DMF (2 mL) at RT. After the reaction mixture was stirred at RT for 20 min, compound 22 (41.0 mg, 0.292 mmol) in DMF (1 mL) was added. Then the reaction mixture was stirred at RT for 1 h. The reaction mixture was injected onto an ISCO 30 g C18 column and eluted with water/acetonitrile (0.05% formic acid) over 30 min. The product-containing fractions were pooled, filtered through a basic resin (PL-HCO3 MP-Resin 1.8 mmol/g; Agilent Part #PL3540-#603), and lyophilized to afford 29.8 mg of compound 25 as a off-white solid. MS: (+) m/z 420.0 (M+1).

DIPEA (0.014 mL, 0.078 mmol) was added to a mixture of compound 4a (45.5 mg, 0.078 mmol), compound 25 (29.8 mg, 0.071 mmol) and HATU (29.7 mg, 0.078 mmol) in DMF (3 mL) at RT. The reaction mixture was stirred at RT for 2 h. The reaction was quenched by addition of saturated NH$_4$Cl solution. The aqueous solution was extracted with EtOAc. The combined organic layers were dried, filtered, and concentrated. The crude product was purified by flash chromatography, eluting from silica gel with a gradient of 0-30% MeOH in DCM to afford 69.9 mg of compound 27 as a light yellow solid. MS: (+) m/z 983.2 (M+1).

Pd(PPh$_3$)$_4$ (4.05 mg, 3.51 µmol) was added to a mixture of compound 27 (69.0 mg, 0.070 mmol), PPh$_3$ (1.841 mg, 7.02 µmol) and pyrrolidine (0.015 mL, 0.175 mmol) in DCM (4 mL) at 0° C. The reaction mixture was allowed to warm to RT and stirred for 30 min. Purification by flash chromatography eluting from silica gel with a gradient of 0-30% MeOH in DCM afforded 25.0 mg of compound (Ib-56) as a white solid. MS: (+) m/z 683.2 (M+1).

Example 9—Dimer-Linker (IIIc-01)

Figure 5A:
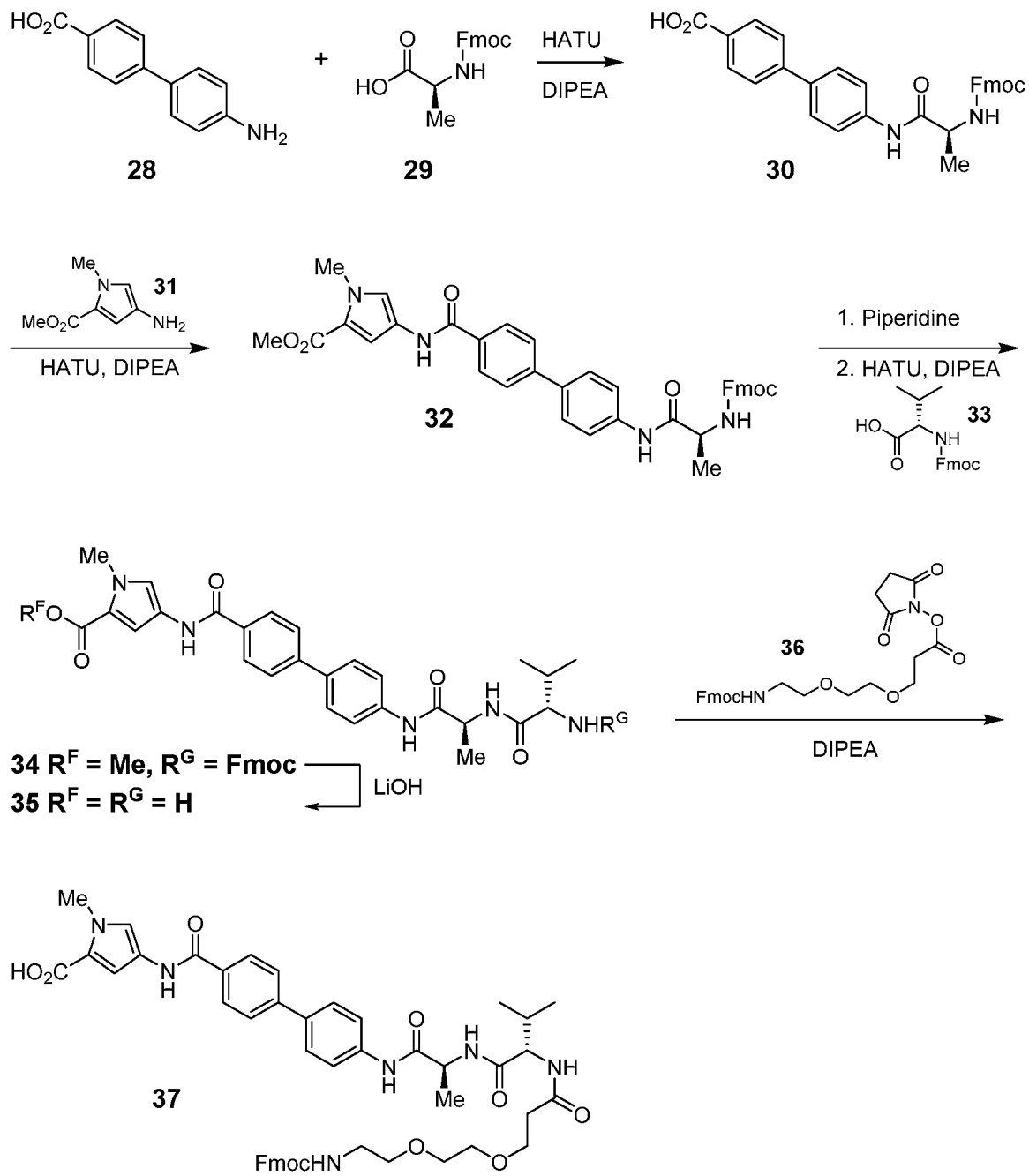
FIGS. 5A and 5B show, in combination, a reaction scheme for the synthesis of another drug-linker compound disclosed herein.
Figure 5B:
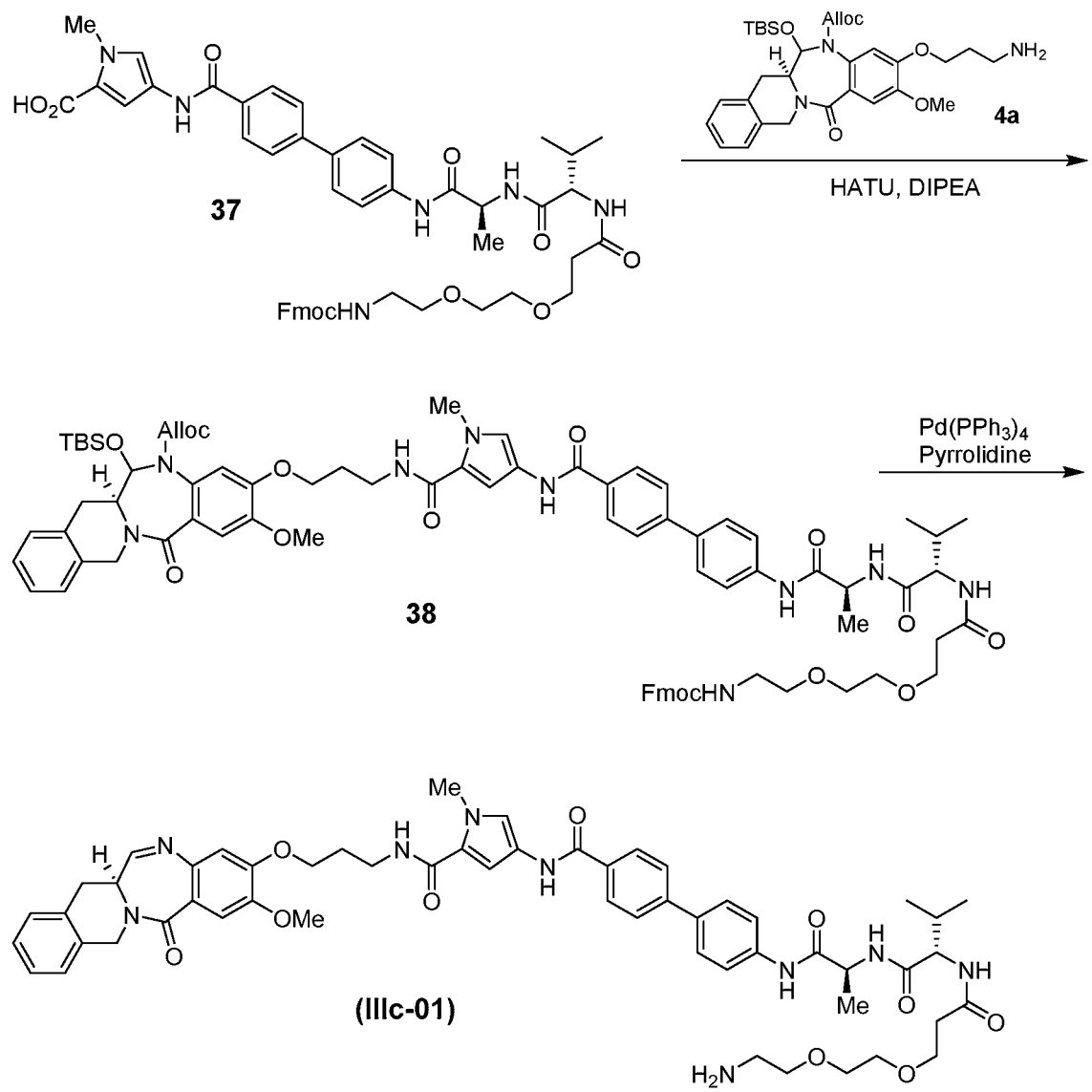

This example and FIGS. 5A-5B relate to the synthesis of dimer-linker (IIIc-01).

DIPEA (0.482 mL, 2.77 mmol) was added to a mixture of Fmoc-protected alanine 29 (0.861 g, 2.77 mmol) and HATU (1.052 g, 2.77 mmol) in DMF (15 mL) at RT. After the reaction mixture was stirred at RT for 1 h, 4'-amino-[1,1'-biphenyl]-4-carboxylic acid 28 (HCl salt, 0.59 g, 2.77 mmol) and DIPEA (0.482 mL, 2.77 mmol) in DMF (5 mL) was added. The reaction mixture was stirred at RT for another one hour and injected on to an ISCO 150 g C18 column and eluted with water/acetonitrile (0.05% formic acid) over 30 min. The product-containing fractions were pooled and lyophilized to afford 0.71 g of compound 30 as a white solid. MS: (+) m/z 507.1 (M+1).

DIPEA (0.620 mL, 3.56 mmol) was added to a mixture of compound 30 (0.82 g, 1.619 mmol), compound 31 (as hydrochloride, 0.299 g, 1.943 mmol) and HATU (0.739 g, 1.943 mmol) in DMF (4 mL) at RT. After the reaction mixture was stirred at RT for 2 h, it was quenched by addition of saturated NH$_4$Cl. The aqueous solution was extracted with EtOAc. The combined organic layers were dried, filtered, and concentrated. The crude product was purified by flash chromatography eluting from silica gel with a gradient of 0-100% EtOAc in hexanes to afford 0.47 g of compound 32 as a white solid. MS: (+) m/z 643.1 (M+1).

Piperidine (0.150 mL, 1.307 mmol) was added to compound 32 (0.42 g, 0.653 mmol) in DMF (5 mL) at RT. After the reaction mixture was stirred at RT for 2 h, the solvent was evaporated to leave a residue.

DIPEA (0.054 g, 0.416 mmol) was added to a mixture of the residue from the previous step (0.175 g, 0.416 mmol), Fmoc-protected valine 33 (0.141 g, 0.416 mmol) and HATU (0.158 g, 0.416 mmol) in DMF (4 mL) at RT. After stirring at RT for 3 h, the reaction was quenched by addition of saturated aqueous $NH_4Cl$. The aqueous solution was extracted with EtOAc. The combined organic layers were dried, filtered, and concentrated. The crude product was purified by flash chromatography eluting from silica gel with a gradient of 0-30% MeOH in DCM to afford 75.8 mg of compound 34 as a white solid. MS: (+) m/z 742.2 (M+1).

LiOH (36.7 mg, 1.533 mmol) in water (2 mL) was added to a mixture of compound 34 (75.8 mg, 0.102 mmol) in THF (4 mL) at RT. The reaction mixture was stirred at RT overnight and then injected onto an ISCO 30 g C18 column and eluted with water/acetonitrile (0.05% formic acid) over 30 min. The product-containing fractions were pooled and lyophilized to afford 15.0 mg compound 35 as a white solid. MS: (+) m/z 504.3 (M−1).

DIPEA (0.048 mL, 0.036 mmol) was added to a mixture of compounds 35 (15 mg, 0.030 mmol) and 36 (17.68 mg, 0.036 mmol) in DMF (3 mL) at RT. The reaction mixture was stirred at RT for 3 h and injected onto an ISCO 30 g C18 column and eluted with water-acetonitrile (0.05% formic acid) over 30 min. The product-containing fractions were pooled and lyophilized to afford 15.0 mg of compound 37 as a white solid. MS: (+) m/z 887.3 (M+1).

DIPEA (3.53 µl, 0.020 mmol) was added to a mixture of compound 37 (15 mg, 0.017 mmol), compound 4a (12.8 mg, 0.022 mmol) and HATU (7.72 mg, 0.020 mmol) in DMF (4 mL) at RT. The reaction mixture was stirred at RT for 4 h and was then injected on to an ISCO 30 g C18 column and eluted with water/acetonitrile (0.05% formic acid) over 30 min. The product-containing fractions were pooled and lyophilized to afford 10.0 mg of compound 38 as a white solid. MS: (+) m/z 1450.5 (M+1).

Pd(PPh$_3$)$_4$ (0.398 mg, 0.345 µmol) was added to a mixture of compound 38 (10 mg, 6.89 µmol) and pyrrolidine (2.014 µl, 0.024 mmol) in DCM (2 mL) at 0° C. The reaction mixture was allowed to warm to RT and stirred at RT for 30 min. The reaction mixture was injected on to an ISCO 30 g C18 column and eluted with water/acetonitrile (0.05% formic acid) over 30 min. The product-containing fractions were pooled and lyophilized to afford 2.5 mg of compound (IIIc-01) as a white solid. MS: (+) m/z 1012.3 (M+1).

Example 10—Dimer-Linker Compound (IIIc-02)

Figure 6A:
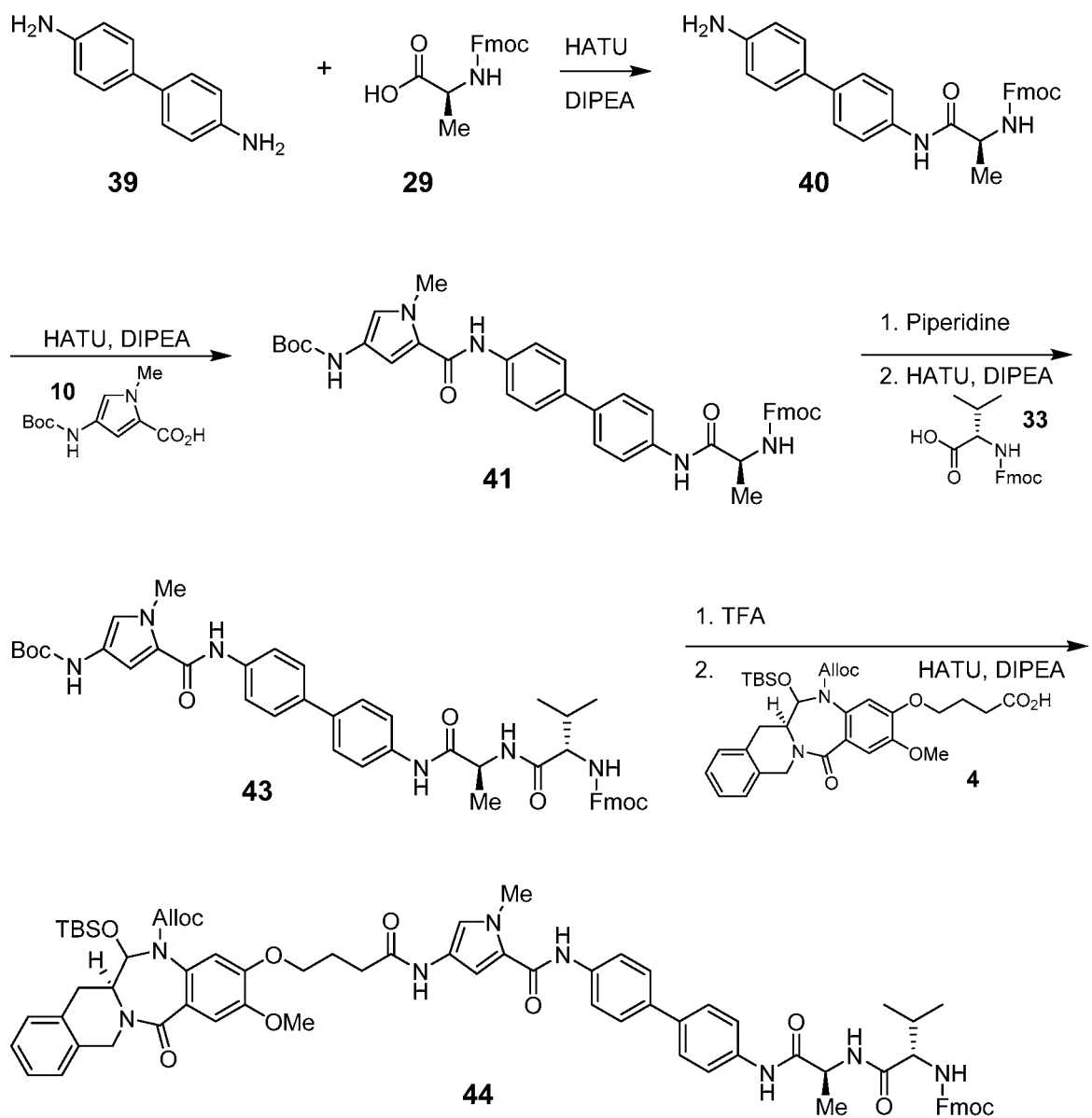
FIGS. 6A and 6B show, in combination, a reaction scheme for the synthesis of yet another drug-linker compound disclosed herein.
Figure 6B:
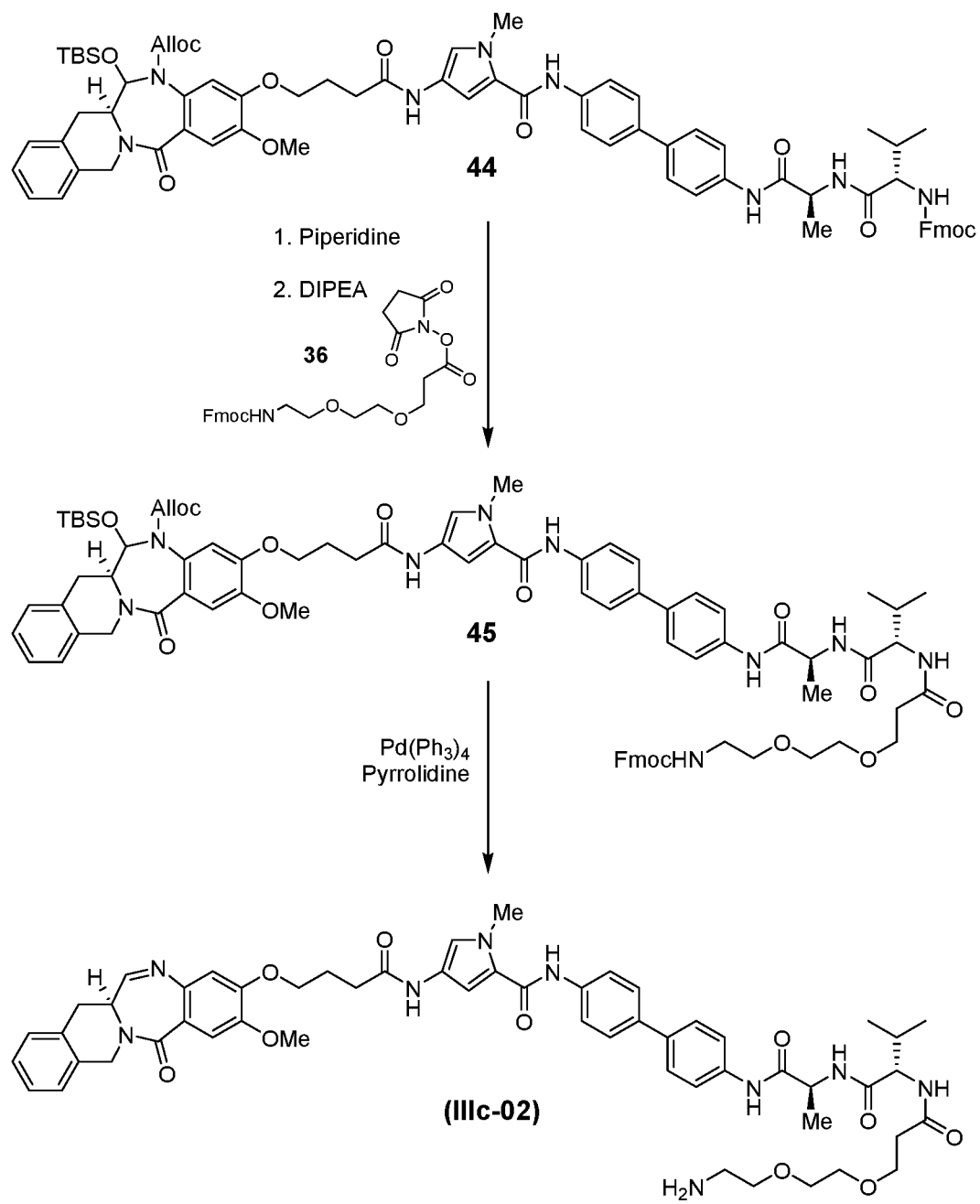

This example and FIGS. 6A-6B relate to the preparation of dimer-linker (IIIc-02). (The orientation of the central pyrrole moiety is reversed, compared to dimer-linker (IIIc-01).)

DIPEA (0.615 mL, 3.53 mmol) was added to a mixture of Fmoc-protected alanine 29 (1 g, 3.21 mmol), benzidine 39 (0.592 g, 3.21 mmol) and HATU (1.221 g, 3.21 mmol) in DMF (15 mL) at RT. The reaction mixture was stirred at RT for 3 h. Water was added to quench the reaction. The off-white solid 40 (0.63 g) was collected by filtration, and then washed with DCM and MeOH. MS: (+) m/z 478.2 (M+1).

DIPEA (0.253 mL, 1.451 mmol) was added to a mixture of compound 40 (0.63 g, 1.319 mmol), pyrrole carboxylic acid 10 (0.317 g, 1.319 mmol) and HATU (0.502 g, 1.319 mmol) in DMF (6 mL) at RT. The reaction mixture was stirred at RT for 3 h. Water was added to quench the reaction. The solid was collected by filtration. DCM was added to dissolve the product, and the impurities were filtered off The crude product was purified by flash chromatography eluting from silica gel with a gradient of 0-100% EtOAc in hexanes to afford 0.21 g of compound 41 as a white solid. MS: (+) m/z 698.6 (M−1).

Piperidine (0.044 mL, 0.450 mmol) was added to a mixture of compound 41 (0.21 g, 0.300 mmol) in DMF (4 mL) at RT. The reaction mixture was stirred at RT for 1 h. The solvent was evaporated to leave a residue.

DIPEA (0.063 mL, 0.359 mmol) was added to a mixture of the above residue (0.143 g, 0.299 mmol) and Fmoc-protected valine 33 (0.157 g, 0.359 mmol) in DMF (4 mL) at RT. The reaction mixture was stirred at RT for 3 h. Water was added to quench the reaction. The white solid (93.0 mg) was collected by filtration, and washed with DCM and MeOH to afford compound 43. MS: (+) m/z 799.3 (M+1).

TFA (1 mL, 0.117 mmol) was added to a solution of compound 43 (93.4 mg, 0.117 mmol) in DCM (2 mL) at RT. The reaction mixture was stirred at RT for 40 min. The solvent was evaporated to leave a residue.

DIPEA (0.022 mL, 0.129 mmol) was added to a mixture of the preceding residue (82 mg, 0.117 mmol), compound 4 (79 mg, 0.129 mmol) and HATU (49.1 mg, 0.129 mmol) in DMF (3 mL) at RT. The reaction mixture was stirred at RT for 3 h. Water was added to quench the reaction. The white solid 44 (114 mg) was collected by filtration, and washed with DCM and MeOH. MS: (+) m/z 1291.5 (M+1).

Piperidine (0.017 mL, 0.177 mmol) was added to a mixture of compound 44 (0.114 g, 0.088 mmol) in DMF (2 mL) at RT. The reaction mixture was stirred at RT for 2 h. The solvent was evaporated to leave a residue.

DIPEA (0.018 mL, 0.105 mmol) was added to a mixture of the above residue (94 mg, 0.088 mmol) and compound 36 (52.4 mg, 0.105 mmol) in DMF (3 mL) at RT. The reaction mixture was stirred at RT for 3 h. Water was added to quench the reaction. The white solid 45 (61.5 mg) was collected by filtration, and washed with DCM and MeOH. MS: (+) m/z 1450.5 (M+1).

Pyrrolidine (0.012 mL, 0.148 mmol) was added to a mixture of compound 45 and Pd(PPh$_3$)$_4$ (2.449 mg, 2.120 µmol) in DCM (3 mL) at 0° C. The reaction mixture was allowed to warm to RT and was stirred at RT for 30 min. The reaction mixture was injected on to an ISCO 30 g C18 column and eluted with water/acetonitrile (0.05% formic acid) over 30 min. The product-containing fractions were pooled and lyophilized to afford 12.7 mg of dimer-linker (IIIc-02) as a white solid. MS: (+) m/z 1012.3 (M+1).

Example 11—Precursor for Compound (Ib-09)

This example describes the preparation of 3-(difluoromethyl)-4-(3-methyl-1H-1,2,4-triazol-1-yl)aniline, which was used instead of compound 9 to prepare compound (Ib-09), analogously following the procedure of Example 5 and FIG. 2.

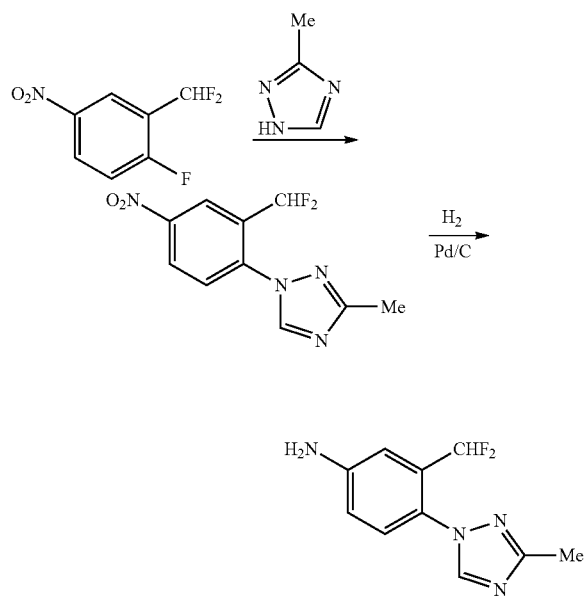

To a magnetically stirred solution of 2-(difluoromethyl)-1-fluoro-4-nitrobenzene (2 g, 10.47 mmol) in DMSO (10 mL) at 0° C. were added $K_2CO_3$ (1.446 g, 10.47 mmol) and 3-methyl-1H-1,2,4-triazole (0.870 g, 10.47 mmol). The reaction mixture was allowed to warm to RT and stirred overnight, poured into ice and extracted with EtOAc (50 mL, twice). The combined organic layers were washed with brine, dried over $Na_2SO_4$, and concentrated under reduced pressure. The residue was purified on Biotage using a 0-20% gradient of EtOAc in petroleum ether. Two sets of fractions with desired product mass were isolated, one of which was confirmed to be the desired nitro triazole product by x-ray crystal analysis. $^1$H NMR (400 MHz, CHLOROFORM-d) δ 400 MHz: 8.74-8.73 (1H, d, J=2.1 Hz), 8.51-8.47 (1H, m), 8.39 (1H, s), 7.70-7.67 (1H, d, J=8.4), 7.39-7.02 (1H, t, J=54), 2.53 (3H, s). LCMS M+H=255.2.

A dried 250 mL two-necked, round-bottom flask equipped with a magnetic stirring bar, an adaptor with an $N_2$ inlet, and a cooled condenser was charged with the nitro triazole product from the preceding step (0.1 g, 0.393 mmol) in MeOH (50 mL). To this added Pd/C (8.37 mg, 0.079 mmol). The reaction mixture was stirred at RT under hydrogen pressure for 6 h. The reaction mixture was filtered through a CELITE™ bed and concentrated under reduced pressure. The residue was dissolved in DCM (10 mL) over silica (5 g). The resultant slurry of the compound on silica (4 g RediSep silica column, 50% EtOAc in petroleum ether) to get the desired compound as a light green solid (0.07 g, 79%). $^1$H NMR (400 MHz, CHLOROFORM-d) δ 8.11 (1H, s), 7.17-7.14 (1H, d, J=8.4 Hz), 7.02-7.01 (1H, d, J=2.0 Hz), 6.80-6.78 (1H, m), 6.78-6.51 (1H, t, J=51 Hz), 4.02 (2H, bs), 2.47 (3H, s). LCMS M+H=225.2.

Example 12—Precursor for Compound (Ib-20)

This example describes the preparation of 4-(4-chloro-1H-imidazol-1-yl)-3-fluoroaniline, which was used instead of compound 9 to prepare compound (Ib-20), analogously following the procedure of Example 5 and FIG. 2.

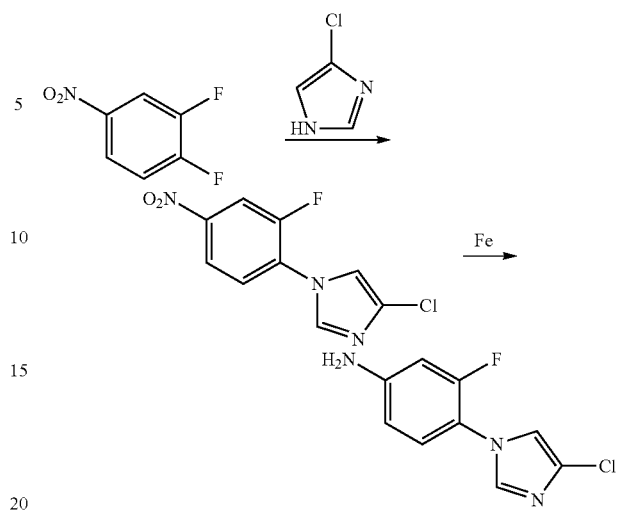

A magnetically stirred mixture of 4-chloro-1H-imidazole (15.0 g, 146 mmol), 1,2-difluoro-4-nitrobenzene (30 g, 189 mmol), and $K_2CO_3$ (20.22 g, 146 mmol) in DMSO (50 mL) was heated at 80° C. for 4 h. The resulting dark black solution was allowed to cool to RT. The reaction contents was poured into 800 mL water and vigorously stirred for 15 min. An orange precipitate immediately crashed out and was collected to give 4-chloro-1-(2-fluoro-4-nitro-phenyl)-1H-imidazole (34.6 g, 98%). $^1$H NMR (500 MHz, CHLOROFORM-d) δ 8.23-8.16 (m, 2H), 7.81-7.78 (m, 1H), 7.61-7.56 (m, 1H), 7.26-7.25 (m, 1H). LCMS M+H=242.07.

Iron powder (4.62 g, 83 mmol) was added to a 250 mL round bottom flask charged with a mixture of the previous product (10 g, 41.4 mmol), HOAc (40 mL, 699 mmol), and EtOH (100 mL). A water cooled reflux condenser was attached to the flask and the the heterogeneous mixture was heated to 100° C. with vigorous stirring for 30 min and cooled to RT. The crude reaction product was filtered over CELITE™ and washed with EtOAc. The organic layer was chilled in an ice bath and neutralized with 5 M NaOH. The resulting solution was poured into a separatory funnel and extracted with EtOAc. The combined organic layers were washed with brine, dried over $Na_2SO_4$, filtered, and concentrated in vacuo to afford a solid. The crude product was analyzed by LCMS and the major peak had an ion consistent with desired product 4-(4-chloro-1H-imidazol-1-yl)-3-fluoroaniline (5.5 g, 68%, used as is). LCMS M+H=212.1.

Example 13—Precursor for Compound (Ib-28)

This example describes the preparation of 3,5-dimethyl-4-(1H-1,2,4-triazol-1-yl)aniline, which was used instead of compound 9 to prepare compound (Ib-28), analogously following the procedure of Example 5 and FIG. 2.

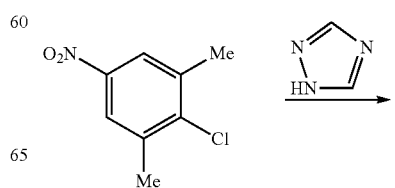

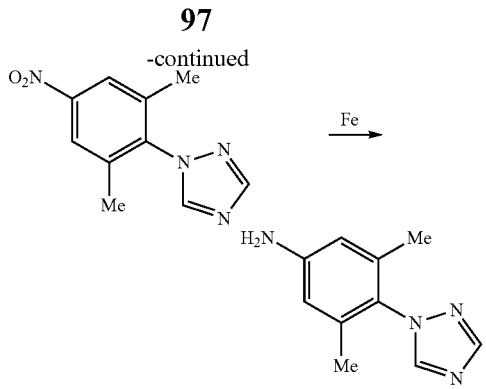

A mixture of 2-chloro-1,3-dimethyl-5-nitrobenzene (1 g, 5.39 mmol), 1H-1,2,4-triazole (0.372 g, 5.39 mmol) and Cs$_2$CO$_3$ (1.931 g, 5.93 mmol) in DMSO (10 mL) was stirred at 90° C. for 16 h then cooled to RT (LC-MS showed minor product formation). The reaction mixture was poured into water, stirred overnight, and filtered. The dark brown filter cake was washed with water and suction-dried, and further dried on the vacuum pump to give 1-(2-methoxy-4-nitrophenyl)-1H-1,2,4-triazole (1.04 g, 88%, used as is). LCMS M+H=219.05.

The product from the preceding step (1 g, 4.58 mmol) was taken up in EtOH/water (2:1, 12 mL), NH$_4$Cl (1.961 g, 36.7 mmol) and iron (1.024 g, 18.33 mmol) were added successively. The mixture was heated at 70° C. for 1 h and cooled to RT. The mixture was then treated with aqueous NH$_4$OH (10 mL) and EtOAc (100 mL). The mixture was stirred for 10 min then filtered through CELITE™. The filter cake was washed successively with water and EtOAc. The filtrate layers were partitioned. The organic phases were dried over MgSO$_4$, filtered and concentrated to give 3,5-dimethyl-4-(1H-1,2,4-triazol-1-yl)aniline as a golden yellow solid (0.85 g, 99%). LCMS M+H=189.04.

Example 14—Precursor for Compound (Ib-50)

This example describes the preparation of 4-(4-aminophenyl)-N,1-dimethyl-1H-imidazole-2-carboxamide, which was used instead of compound 9 to prepare compound (Ib-50), analogously following the procedure of Example 5 and FIG. 2.

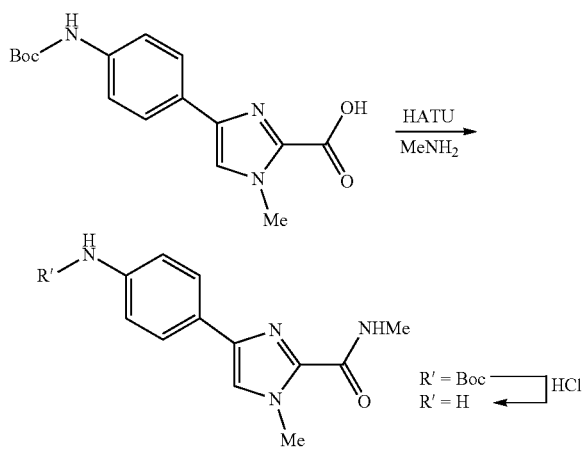

To a solution of 4-(4-(((tert-butoxycarbonyl)amino)phenyl)-1-methyl-1H-imidazole-2-carboxylic acid (0.068 g, 0.215 mmol, 1 equiv) and DIPEA (0.15 mL, 0.860 mmol, 4 equiv) in DCM (2.2 mL) was added HATU (0.114 g, 0.301 mmol, 1.4 equiv). After 2 min, methylamine hydrochloride (0.029 g, 0.430 mmol, 2 equiv) was added. After 1 h, the reaction mixture was purified directly by silica gel flash column chromatography (0-100% EtOAc/hex) to provide the corresponding methyl amide (0.060 g, 85%) as a white solid. $^1$H NMR (400 MHz, CDCl$_3$) 7.46-7.31 (m, 4H), 6.97 (s, 1H), 6.74 (s, 1H), 6.46 (br. s., 1H), 5.92 (br. s., 1H), 3.98 (s, 3H), 2.97 (d, J=4.8 Hz, 3H), 1.54 (s, 9H); LCMS M+H=330.10.

To a solution of the methyl amide (0.060 g, 0.182 mmol, 1 equiv) in DCM (1 mL) and MeOH (1 mL) was added 4 N HCl in dioxane (3 mL). After 3 h, the reaction was concentrated in vacuo to provide 4-(4-aminophenyl)-N,1-dimethyl-1H-imidazole-2-carboxamide. LCMS M+H=230.05.

Example 15—Precursor for Compound (Ib-53)

This example describes the preparation of allyl (4'-amino-3,3'-dimethoxy-[1,1'-biphenyl]-4-yl)carbamate, which was used instead of compound 9 to prepare compound (Ib-53), analogously following the procedure of Example 5 and FIG. 2.

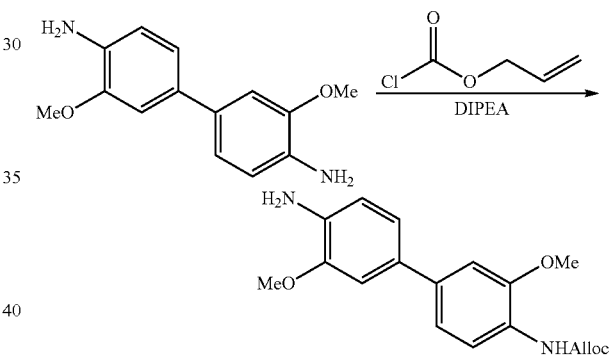

To a solution of 3,3'-dimethoxy-[1,1'-biphenyl]-4,4'-diamine (2.3 g, 9.42 mmol, 1 equiv) and DIPEA (4.9 mL, 28.2 mmol, 3 equiv) in THF (94 mL) was added allyl chloroformate (1.14 mL, 9.42 mmol, 1 equiv). After 1 h, the reaction was diluted with EtOAc and washed with brine (×2). The EtOAc layer was dried (Na$_2$SO$_4$) and concentrated in vacuo. The crude product was purified by flash column silica gel chromatography (10-100% EtOAc/hexane gradient) to give product (1.78 g, 58%) as a viscous tan oil. $^1$H NMR (400 MHz, CDCl$_3$) δ 8.12 (br. s., 1H), 7.32-7.28 (m, 1H), 7.14 (dd, J=8.4, 1.4 Hz, 1H), 7.06-6.98 (m, 3H), 6.78 (d, J=7.8 Hz, 1H), 6.10-5.91 (m, 1H), 5.40 (dd, J=17.2, 1.4 Hz, 1H), 5.32-5.24 (m, 1H), 4.70 (d, J=5.5 Hz, 2H), 3.94 (s, 6H), 3.86 (br. s., 2H); LCMS M+H=329.00.

Example 16—Precursor for Compound (Ib-54)

This example describes the preparation of allyl (4'-amino-[1,1'-biphenyl]-4-yl)carbamate, which was used instead of compound 9 to prepare compound (Ib-54), analogously following the procedure of Example 5 and FIG. 2.

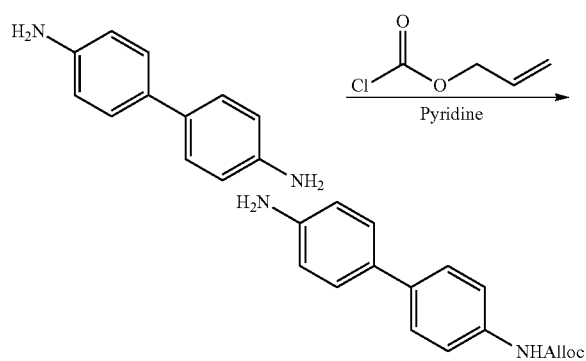

To a solution of benzidine (2 g, 10.9 mmol, 2 eq.) and pyridine (0.53 mL, 5.51 mmol, 1.2 equiv) in THF was added allyl chloroformate (0.58 mL, 5.43 mmol, 1 equiv). Immediate formation of an off-white precipitate was observed. After stirring for 18 h, the reaction mixture was diluted with EtOAc and washed with 10% aqueous $K_2CO_3$ and then brine. The EtOAc layer was dried ($Na_2SO_4$) and concentrated in vacuo. The crude product was purified by flash column silica gel chromatography (10-100% EtOAc/hexane gradient) to give product (0.78 g, 54%) as a pale orange solid. $^1$H NMR (400 MHz, $CDCl_3$) δ 7.51-7.46 (m, 2H), 7.44-7.37 (m, 4H), 6.76 (d, J=8.5 Hz, 2H), 6.65 (br. s., 1H), 6.09-5.89 (m, 1H), 5.39 (d, J=17.3 Hz, 1H), 5.29 (d, J=10.3 Hz, 1H), 4.70 (d, J=5.8 Hz, 2H), 3.74 (br. s., 2H); LCMS M+H 269.0.

Example 17—Precursor for Compound (M-11)

This example describes the preparation of 3-(2,2-difluoroethoxy)-4-(3-methyl-1H-1,2,4-triazol-1-yl)aniline, which used instead of compound 9 to prepare compound (Ib-11), analogously following the procedure of Example 5 and FIG. 2.

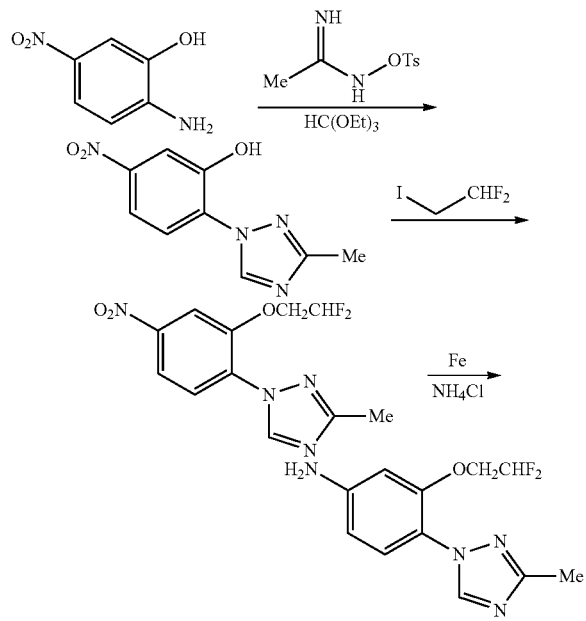

2-Aminoprop-1-en-1-yl 4-methylbenzenesulfonate (0.265 g, 1.168 mmol), NMP (1.946 ml), 2-amino-5-nitrophenol (0.15 g, 0.973 mmol), triethyl orthoformate (0.178 ml, 1.071 mmol) and ethanesulfonic acid (10.72 mg, 0.097 mmol) were added to a 25 mL round-bottomed flask. The dark yellow solution was stirred 40° C. under argon for 20 h. The reaction was diluted with water (16 mL). A thick yellow precipitate formed. The pH was adjusted to about 7 with saturated $NaHCO_3$. The suspension was stirred at RT for 1 h. The suspension was filtered and the flask and solids were washed with water (2×8 mL). The tan solid (0.186 g, 86%) that remained was vacuum dried for 17 h. $MH^+$=220.9.

A mixture of 2-(3-methyl-1H-1,2,4-triazol-1-yl)-5-nitrophenol (1 g, 4.54 mmol), 1,1-difluoro-2-iodoethane (0.872 g, 4.54 mmol) was dissolved in DMF (5 mL). To that was added $K_2CO_3$ (0.753 g, 5.45 mmol). The reaction mixture was refluxed at 80° C. overnight. Then the reaction mixture was concentrated under reduced pressure. Then the crude mixture was quenched with ice cold water (15 ml) to get precipitate which was filtered and dried overnight to get 1-(2-(2,2-difluoroethoxy)-4-nitrophenyl)-3-methyl-1H-1,2,4-triazole (1 g, 77%) as a brown solid. $MH^+$=285.6.

A dried 500 mL two-necked round-bottom flask (equipped with a magnetic stirring bar, a cooled condenser, and an adaptor with an $N_2$ inlet) was charged with the product from the preceding step (1 g, 3.52 mmol) dissolved in ethanol (30 mL) and water (15 mL) under nitrogen atmosphere. To the flask were added $NH_4Cl$ (0.941 g, 17.59 mmol) and iron (0.982 g, 17.59 mmol). The reaction mixture was heated at 80° C. overnight. Then the reaction mixture was cooled to RT, filtered through CELITE™ and concentrated under reduced pressure to obtain 3-(2,2-difluoroethoxy)-4-(3-methyl-1H-1,2,4-triazol-1-yl)aniline (0.8 g, 89%) as brown solid. $^1$H NMR (400 MHz, DMSO-$d_6$) δ ppm 8.34-8.55 (s, 1H) 7.22 (br. s., 1H) 6.16-6.54 (m, 3H) 5.61 (br. s., 2H) 4.11-4.40 (m, 2H) 2.31 (s, 3H). $MH^+$=255.2.

Example 18—Precursor for Compound (Ib-32)

This example describes the preparation of 4H-benzo[b][1,2,4]triazolo[4,3-d][1,4]oxazin-8-amine, which used instead of compound 9 to prepare compound (Ib-32), analogously following the procedure of Example 5 and FIG. 2.

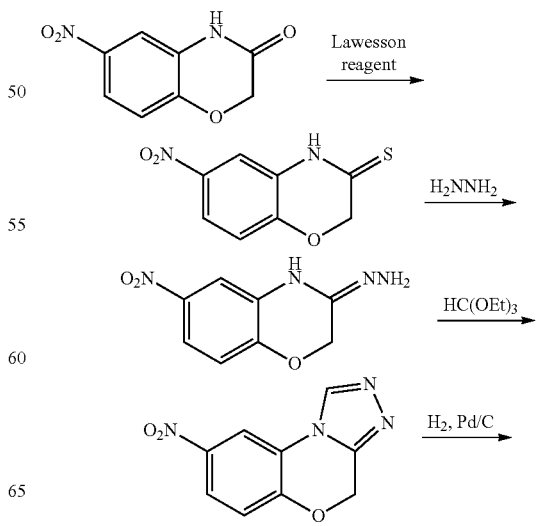

101
-continued

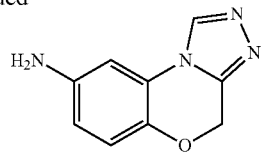

Lawesson's reagent (6.5 g, 15.75 mmol) was added to a brown suspension of 6-nitro-2H-benzo[b][1,4]oxazin-3 (4H)-one (6.15 g, 31.68 mmol) in THF (160 mL) and the heterogenous mixture was stirred at RT for 18 h. The resultant clear golden yellow solution was diluted with water (1300 mL), and the yellow suspension was filtered. The filter cake was washed with water, taken up in ETOAc, washed with brine, then concentrated. The residue was purified on silica using 1-5% EtOAc in DCM. The desired fractions were concentrated to give a yellow solid (5.45 g, 82%). MH$^+$=211.3.

Hydrazine monohydrate (0.46 mL, 9.28 mmol) was added to a pale yellow solution of 6-nitro-2H-benzo[b][1,4] oxazine-3(4H)-thione (1.5 g, 7.14 mmol) in ethanol (100 mL) and the resultant bright yellow suspension was stirred at RT overnight and concentrated. The residue was taken up in water and the suspension was filtered, the filter cake was washed with water and suction-dried to give a bright yellow solid (1.3 g, 87%). MH$^+$=209.4.

A mixture of (E)-3-hydrazono-6-nitro-3,4-dihydro-2H-benzo[b][1,4]oxazine (0.5 g, 2.4 mmol) and triethyl orthoformate (8.15 mL, 48 mmol) was heated to 150° C. for 3 h and concentrated. The bright yellow residue was taken up in methanol (18 mL), filtered, filter cake washed with methanol and suction-dried to give a yellow solid (0.46 g, 88%). MH$^+$=219.2.

A suspension of 8-nitro-4H-benzo[b][1,2,4]triazolo[4,3-d][1,4]oxazine (0.46 g,) in THF/MeOH (1:1, 100 mL) was subjected to hydrogenation at 1 atm using 10% Pd/C (0.1 g) for 18 h. The reaction mixture was filtered through CELITE™ and concentrated. The residue was purified on silica using 2-7% MeOH in DCM. The desired fractions were concentrated to give a pale yellow solid (0.29 g, 73%). MH$^+$=189.3.

Example 19—Precursor for Compound (Ib-48)

This example describes the preparation of 4-amino-1-methyl-N-phenyl-1H-imidazole-2-carboxamide, which used instead of compound 12 to prepare compound (Ib-48), analogously following the procedure of Example 5 and FIG. 2.

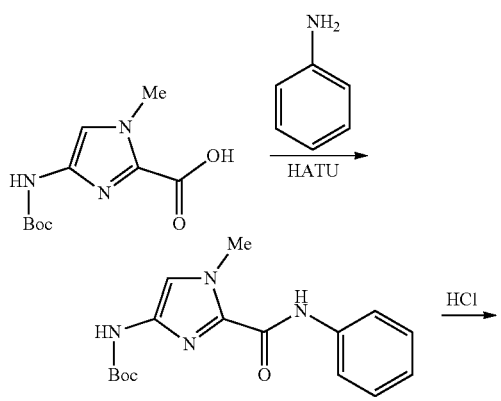

102
-continued

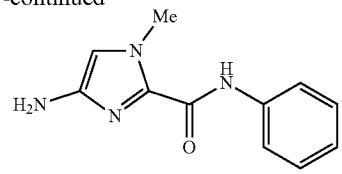

4-((tert-Butoxycarbonyl)amino)-1-methyl-1H-imidazole-2-carboxylic acid was coupled with aniline in an HATU-mediated reaction, followed by removal of the Boc protecting group with HCl, generally following the conditions described hereinabove, to yield 4-amino-1-methyl-N-phenyl-1H-imidazole-2-carboxamide.

Example 20—Precursor for Compound (Ib-52)

This example describes the preparation of allyl (4-(4-amino-1-methyl-1H-pyrrole-2-carboxamido)phenyl)carbamate, which was used instead of compound 12 to prepare compound (Ib-52), analogously following the procedure of Example 5 and FIG. 2.

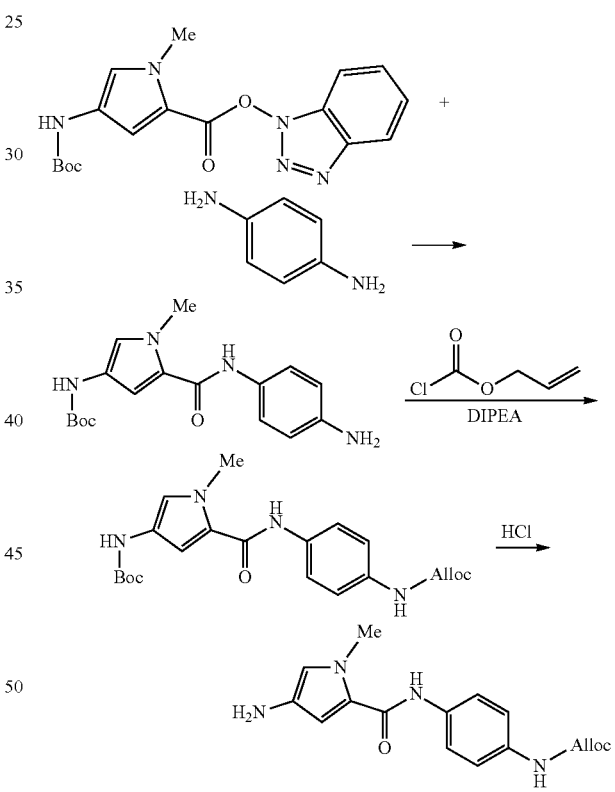

A solution of benzene-1,4-diamine (0.90 g, 8.32 mmol, 1.1 equiv) and 1H-benzo[d][1,2,3]triazol-1-yl4-((tert-butoxycarbonyl)amino)-1-methyl-1H-pyrrole-2-carboxylate (2.68 g, 7.49 mmol, 1 equiv) in DMF (21 mL) was heated at 60° C. for 2 h. Upon cooling to RT, the reaction was diluted with EtOAc and washed with water and then brine. The EtOAc layer was dried (Na$_2$SO$_4$) and concentrated in vacuo. The crude product was purified by flash column silica gel chromatography (60-100% EtOAc/hexane gradient) to give the adduct (3.17 g, 100%) as a viscous brown oil. $^1$H NMR (400 MHz, CDCl$_3$) δ 7.79 (d, J=2.3 Hz, 1H), 7.49-7.39 (m, 2H), 7.30 (d, J=8.5 Hz, 2H), 6.84 (br. s., 1H), 6.68

(d, J=8.5 Hz, 2H), 6.58 (br. s., 1H), 6.23 (br. s., 1H), 3.90 (s, 3H), 1.52 (s, 9H); LCMS M+H=331.05.

To a solution of the adduct (0.59 g, 1.79 mmol, 1 equiv) and DIPEA (0.75 mL, 4.29 mmol, 2.4 equiv) in DCM (9 mL) was added allyl chloroformate (0.23 mL, 2.14 mmol, 1.2 equiv). After stirring 2 h, the reaction was diluted with EtOAc and washed with water and then brine. The EtOAc layer was dried (Na$_2$SO$_4$) and concentrated in vacuo. The crude product was purified by flash column silica gel chromatography (20-100% EtOAc/hexane) to give the Alloc protected compound (0.13 g, 18%) as a poorly soluble tan solid. LCMS M+H=415.05.

To a solution of the Alloc-protected compound (0.13 g, 0.314 mmol, 1 equiv) in DCM (1 mL) and MeOH (1 mL) was added 4 N HCl in dioxane (2 mL). After 2 h, the reaction as concentrated in vacuo to provide the HCl salt of allyl (4-(4-amino-1-methyl-1H-pyrrole-2-carboxamido)phenyl) carbamate (0.13 g, 100%) as a tan solid LCMS M+H=315.10.

Example 21—Precursor for Compound (Ib-49)

This example describes the preparation of 4-amino-1-methyl-N-(4-(1-methyl-5-(oxazol-2-yl)-1H-pyrrol-3-yl)phenyl)-1H-pyrrole-2-carboxamide, which was used instead of compound 12 to prepare compound (Ib-49), analogously following the procedure of Example 5 and FIG. 2 was diluted with EtOAc. The EtOAc solution was washed with water and then brine. The EtOAc layer was dried (Na$_2$SO$_4$) and concentrated in vacuo.

The crude amide product was then treated with MsOH (1.2 mL) and P$_2$O$_5$ (0.12 g) and heated at 140° C. for 3 h. Upon cooling to RT, the dark brown mixture was added to 1 N NaOH and extracted with DCM (×3). The combined DCM layers were dried (Na$_2$SO$_4$) and concentrated in vacuo to yield the crude oxazole product.

The crude oxazole was taken up in DMF (2 mL) and 1H-benzo[d][1,2,3]triazol-1-yl 4-((tert-butoxycarbonyl)amino)-1-methyl-1H-pyrrole-2-carboxylate (0.29 g, 0.822 mmol, 2 equiv) was added. After stirring 18 h, the DMF solution was diluted with EtOAc and washed with water and brine. The EtOAc layer was washed with water then brine. The EtOAc layer was dried (Na$_2$SO$_4$) and concentrated in vacuo. The crude product was purified by flash column silical gel chromatography (30-100% EtOAc/hexane gradient) to provide the Boc-protected quasi-final product (0.149 g, 79%) as a tan solid. $^1$H NMR (400 MHz, CDCl$_3$) δ 9.10 (br. s., 1H), 7.65 (br. s., 1H), 7.62 (d, J=8.5 Hz, 2H), 7.49 (d, J=8.5 Hz, 2H), 7.18 (s, 1H), 6.92 (t, J=6.3 Hz, 1H), 6.87 (br. s., 1H), 6.76 (d, J=7.0 Hz, 1H), 6.70 (br. s., 1H), 6.28 (br. s., 1H), 4.24 (s, 3H), 3.95 (s, 3H), 1.53 (s, 9H); LCMS M+H=462.15.

To a slurry of the Boc-protected product (0.15 g, 0.323 mmol, 1 equiv) in MeOH (1 mL) and DCM (1 mL) was

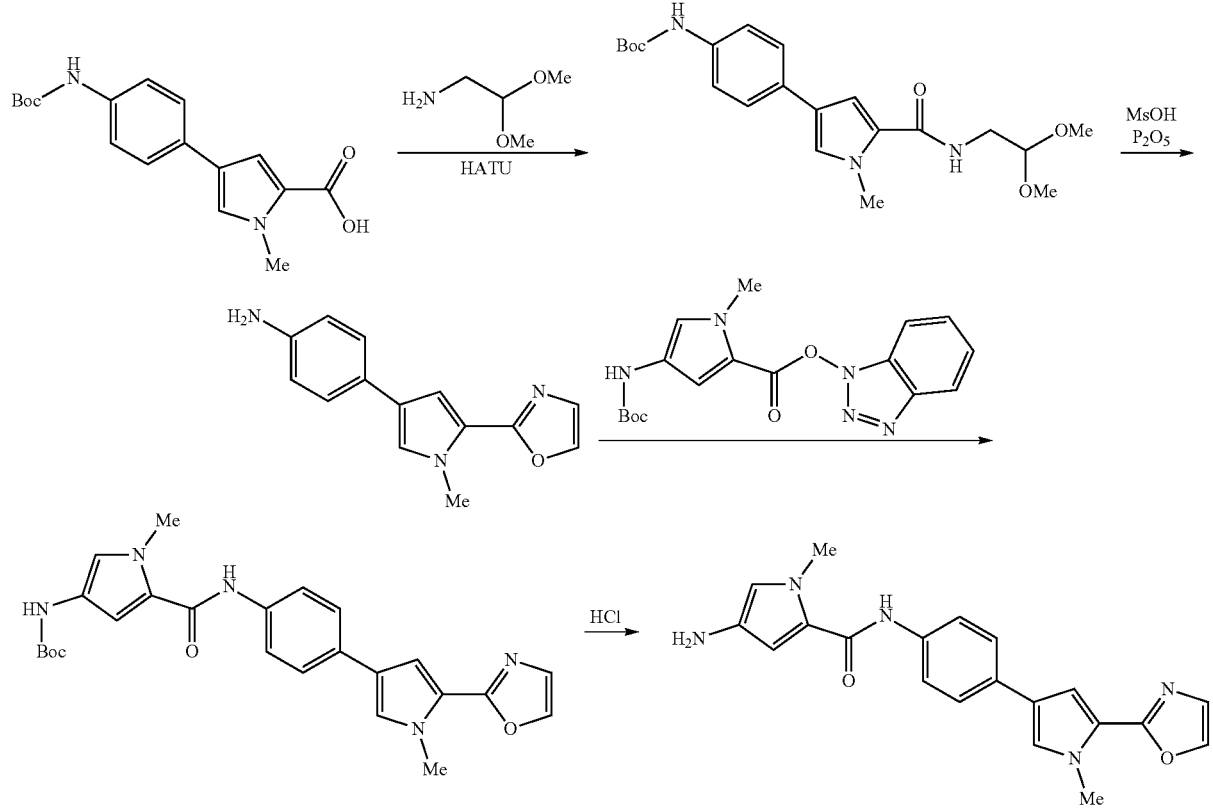

To a solution of 4-(4-((tert-butoxycarbonyl)amino)phenyl)-1-methyl-1H-pyrrole-2-carboxylic acid (0.13 g, 0.411 mmol, 1 equiv) and 2,2-dimethoxyethanamine (0.13 g, 1.23 mmol, 3 equiv) in DMF (4.1 mL) was added HATU (0.22 g, 0.575 mmol, 1.4 equiv). After stirring for 2 h, the reaction added 4 N HCl in dioxane (4 mL). After 1 h, concentrate in vacuo to provide the HCl salt of 4-amino-1-methyl-N-(4-(1-methyl-5-(oxazol-2-yl)-1H-pyrrol-3-yl)phenyl)-1H-pyrrole-2-carboxamide (0.142 g) as a cream colored solid. $^1$H NMR (400 MHz, DMSO-d6) d 10.99 (d, J=5.3 Hz, 1H), 9.99

(s, 1H), 9.90 (br. s., 3H), 7.76 (d, J=8.3 Hz, 2H), 7.59 (s, 1H), 7.51 (d, J=8.5 Hz, 2H), 7.17 (s, 1H), 7.10 (s, 1H), 6.92 (t, J=6.4 Hz, 1H), 6.66 (d, J=6.8 Hz, 1H), 4.10 (s, 3H), 3.91 (s, 3H); LCMS M+H=362.00.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.
Ahmed et al., US 2012/0095213 A1 (2012).
Baraldi et al., *Bioorg. Med. Chem. Lett.* 1998, 8, 3019.
Baraldi et al., *J. Med. Chem.* 1999, 42, 5131.
Bose et al., *J. Am. Chem. Soc.* 1992, 114(12), 4939.
Damayanthi et al., *J. Org. Chem.* 1999, 64, 290.
Junutula et al., US 2016/0271142 A1 (2016).
Kumar and Lown, *Oncology Res.* 2002, 13, 221.
Kumar and Lown, *Org. Biomol. Chem.* 2003, 1, 3327.
Kumar et al., *Heterocycl. Commun.* 2002, 8 (1), 19.
Kumar et al., *Eur. J. Med. Chem.* 2005, 40(7), 641.
McDonald et al., US 2016/0199510 A1 (2016).
Rahman et al., *J. Med. Chem.* 2013, 56, 2911.
Reddy et al., *Anti-Cancer Drug Design* 2000, 15, 225.
Schrama et al., *Nature Rev. Drug Disc.* 2006, 5, 147-159.
Tercel et al., *J. Med. Chem.* 2003, 46(11), 2132.
Thurston et al., WO 93/18045 A1 (1993).
Thurston et al., WO 2016/198869 A1.
Wells et al., *J. Med. Chem.* 2006, 49(18), 5442.
Zhang et al., US 2016/0200742 A1 (2016)

What is claimed is:

1. A compound having a structure according to formula (Ib-54)

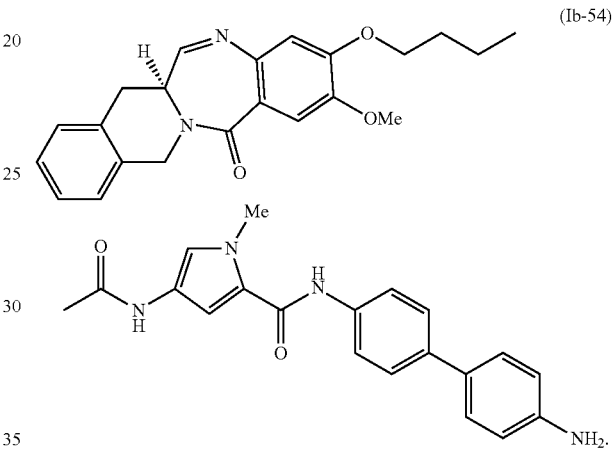

* * * * *